US008530633B2

(12) United States Patent
Frommer et al.

(10) Patent No.: US 8,530,633 B2
(45) Date of Patent: Sep. 10, 2013

(54) DEVELOPMENT OF SENSITIVE FRET SENSORS AND METHODS OF USING THE SAME

(75) Inventors: Wolf B. Frommer, Washington, DC (US); Sakiko Okumoto, Washington, DC (US); Loren Looger, Washington, DC (US); Marcus Fehr, Washington, DC (US)

(73) Assignee: Carnegie Institution of Washington, Washington, DC (US)

( * ) Notice: Subject to any disclaimer, the term of this patent is extended or adjusted under 35 U.S.C. 154(b) by 940 days.

(21) Appl. No.: 11/665,339

(22) PCT Filed: Oct. 14, 2005

(86) PCT No.: PCT/US2005/036957
§ 371 (c)(1),
(2), (4) Date: Sep. 29, 2009

(87) PCT Pub. No.: WO2006/044612
PCT Pub. Date: Apr. 27, 2006

(65) Prior Publication Data
US 2010/0037329 A1 Feb. 11, 2010

Related U.S. Application Data

(60) Provisional application No. 60/618,179, filed on Oct. 14, 2004, provisional application No. 60/643,576, filed on Jan. 14, 2005, provisional application No. 60/654,447, filed on Feb. 22, 2005, provisional application No. 60/658,141, filed on Mar. 4, 2005.

(51) Int. Cl.
*C12N 15/11* (2006.01)
*C12N 15/85* (2006.01)
*C07H 21/04* (2006.01)
*A61K 35/00* (2006.01)

(52) U.S. Cl.
USPC .......... 536/23.1; 536/23.4; 424/93.1; 435/325

(58) Field of Classification Search
USPC ............... 536/23.1, 23.4; 424/93.1; 435/325
See application file for complete search history.

(56) References Cited

U.S. PATENT DOCUMENTS

| | | | |
|---|---|---|---|
| 5,795,729 | A | 8/1998 | Lee |
| 5,981,200 | A | 11/1999 | Tsien |
| 5,998,204 | A | 12/1999 | Tsien |
| 6,197,534 | B1 | 3/2001 | Lakowicz |
| 6,277,627 | B1 | 8/2001 | Hellinga |
| 6,376,257 | B1 | 4/2002 | Persechini |
| 6,465,199 | B1 | 10/2002 | Craig |
| 6,469,154 | B1 | 10/2002 | Tsien |
| 2002/0058273 | A1 | 5/2002 | Shipwash |
| 2003/0134346 | A1 | 7/2003 | Amiss |
| 2004/0029129 | A1 | 2/2004 | Wang |
| 2004/0118681 | A1 | 6/2004 | Hellinga |
| 2005/0112685 | A1 | 5/2005 | Amiss |
| 2005/0196768 | A1 | 9/2005 | Campbell |

FOREIGN PATENT DOCUMENTS

| | | |
|---|---|---|
| WO | WO 00/49183 | 8/2000 |
| WO | WO 01/18237 | 3/2001 |
| WO | WO 03/025220 | 3/2003 |
| WO | WO 2006//044611 | 4/2006 |
| WO | WO 2006/096213 | 9/2006 |
| WO | WO 2006/096214 | 9/2006 |
| WO | WO 2007/046786 | 4/2007 |

OTHER PUBLICATIONS

Marvin et al. (PNAS, 1997, 94: 4366-71).*
Benson et al. "Design of bioelectronic interfaces by exploiting hinge-bending motions in proteins." Science 293: 1641-1644, 2001.
Blicharska et al. "Fluorescence quenching of Trp Repressor-Operator interaction." Journal of Protein Chemistry 18: 823-830, 1999.
Chen et al. "Protein localization in living cells and issues using FRET and FLIM." Differentiation 71: 528-541, 2003.
D'Auria et al. "Enzyme fluorescence as a sensing tool: new perspectives in biotechnology." Curr. Opin. in Biotechnol. 12: 99-104, 2001.
De et al. "Novel biosensors for the detection of estrogen receptor ligands." Journal of Steroid Biochemistry and Molecular Biology 96: 235-244, 2005.
De Lorimier et al. "Construction of a fluorescent biosensor family." Protein Science 11: 2662, 2663, and 2670, 2002.
Deuschle et al. "Construction and optimization of a family of genetically encoded metabolite sensors by semirational protein engineering." Protein Science 14: 2304-2314, 2005.
Dwyer et al. "Periplamsic binding proteins: a versatile superfamily for protein engineering." Current Opinion in Structural Biology vol. 14, No. 4, 2004.
Fehr et al. "Visualization of maltose uptake in living yeast cells by fluorescent nanosensors." PNAS 99: 9846-9851, 2002.
Gaits et al. "Shedding light on cell signaling: Interpretation of FRET biosensors," Science's STKE: signal transduction knowledge environment: 165 (PE3): 1-5, 2003.
Gu et al. "A novel analytical method for in vivo phosphate tracking." FEBS Lett. 580: 5885-5893, 2006.
Gunsalus et al. "Nucleotide sequence and expression of *Escherichia coli trpR*, the structural gene for the *trp* aporepressor." PNAS 77: 7117-7121, 1980.

(Continued)

*Primary Examiner* — Gerald Leffers, Jr.
*Assistant Examiner* — Magdalene Sgagias
(74) *Attorney, Agent, or Firm* — Morgan, Lewis & Bockius LLP

(57) ABSTRACT

Intramolecular biosensors are disclosed, including PBP-based biosensors, comprising a ligand binding domain fused to donor and fluorescent moieties that permit detection and measurement of Fluorescence Resonance Energy Transfer upon binding ligand. At least one of the donor and fluorescent moieties may be internally fused to the biosensor such that both ends of the internally fused fluorophore are fixed. In addition, methods of improving the sensitivity of terminally fused biosensors are provided. The biosensors of the invention are useful for the detection and quantification of ligands in vivo and in culture.

12 Claims, 19 Drawing Sheets

(56) References Cited

OTHER PUBLICATIONS

Jenne et al. "Real-time characterization of ribozymes by fluorescence resonance energy transfer (FRET)." Angewandte Chemie 38: 1300-1303, 1999.
Mitra et al. "Fluorescence resonance energy transfer between blue-emitting and red-shifted excitation derivatives of the green fluorescent protein." Gene 173: 13-17, 1996.
Miyawaki et al. "Fluorescent indicators for Ca2+ based on green fluorescent proteins and clamodulin." Nature 388: 882-887, 1997.
Muyan et al. "Fusion estrogen receptor proteins: toward the development of receptor-based agonists and antagonists." Molecular and Cellular Endocrinology 182: 249-263.
Nagai et al. "A variant of yellow fluorescent protein with fast and efficient maturation for cell-biological application." Nature Biotechnology vol. 20, No. 1, 2002.
Okumoto et al. "Detection of glutamate release from neurons by genetically encoded surface-displayed FRET nanosensors." PNAS 102: 8740-8745, 2005.
Okumoto et al. "Genetically encoded sensors for ions and metabolites." Soil Sci. Plant Nutr. 50: 947-953, 2004.
Salins et al. "Phosphate binding protein as the biorecognition element in a biosensor for phosphate." Sensors and Actuators B 97: 81-89, 2004.
Schafer et al. "X-ray structures of the maltose-maltodextrin-binding protein of the thermophilic bacterium *Alicyclobacillus acidocaldarius* provide insight into acid stability of proteins." J. Mol. Biol. 335: 261-274. 2004.
Sigmund "Viewpoint: are studies in genetically altered mice out of control?" Arterioscler. Thromb. Vasc. Biol. 20: 1425-1429, 2000.
Tolosa et al. "Glucose sensor for low-cost lifetime-based sensing using a genetically engineered protein." Analytical Biochemistry 267: 114-120, 1999.
Tsien "Building and breeding molecules to spy on cells and tumors." FEBS Lett. 579: 927-932, 2005.
Widersten et al. "Optimized heterologous expression of the polymorphic human glutathione transferase M1-1 based on silent mutations in the corresponding cDNA." Protein Expression and Purification 7: 367-371, 1996.
Wood et al. PRI-80 Database, Accession No. AI2966, Jul. 9, 2004, The Genome of the Natural Genetic Engineer *Agrobacterium tumefaciens* C58, Yoo et al. Science 294: 2317-2323, 2001.
Xu et al. "Kinetic and thermodynamic studies of purine repressor binding to corepressor and operator DNA." Journal of Biological Chemistry 273: 8058-8064, 1998.
Zhang et al. "Genetically encoded reporters of protein kinase A activity reveal impact of substrate tethering." PNAS 98: 14997-15002, 2001.
Ge et al. "Dual-labeled glucose binding protein for ratiometric measurements of glucose." Anal. Chem. 76: 1403-01410, 2004.
Hossain et al. "Fluorescence resonance energy transfer in a novel cyclodextrin-peptide conjugate for detecting steroid molecules." Bioorganic & Medicinal Chem. Lett. 13: 4305-4308, 2003.
Anderluh et al. "Concerted folding and binding of a flexible colicin domain to its periplasmic receptor To11A." J. Biol. Chem. 278: 21860-21868, 2003.
Fehr et al. "In vivo imaging of the dynamics of glucose uptake in the cytosol of COS-7 cells by fluorescent nanosensors." J. Biol. Chem. 278: 19127-19133, 2003.
Hires et al. "Optical measurement of synaptic glutamate spillover and reuptake by linker optimized glutamate-sensitive fluorescent reporters." PNAS 105: 4411-4416, 2008.

\* cited by examiner

A

B

FIGURE 11B   FLIP-mglBF16A-Y12S-CFP-D13R-YFP

FIGURE 11D   FLIP-YFP-mglBF16A-T262S-CFP-N263R

FIGURE 11F   FLIP-YFP-mglBF16A-T12S-CFP-D13R

FIGURE 11H   FLIP-mglBF15A-G275S-CFP-K276R-YFP

FIGURE 13

FIGURE 14

DEVELOPMENT OF SENSITIVE FRET SENSORS AND METHODS OF USING THE SAME

CROSS REFERENCE TO RELATED APPLICATIONS

The present application is a U.S. National Phase Application of International Application No. PCT/US2005/036957, filed Oct. 14, 2005, which claims the benefit of U.S. Provisional application 60/618,179, filed Oct. 14, 2004, U.S. Provisional application 60/643,576, filed Jan. 14, 2005, U.S. Provisional application 60/654,447, filed Feb. 22, 2005, and U.S. Provisional application 60/658,141, filed Mar. 4, 2005, which are herein incorporated by reference in their entireties.

This application is also related to provisional application Ser. No. 60/658,142, provisional application Ser. No. 60/657,702, PCT application no. PCT/US2005/036955 PCT application no. PCT/US2005/036953, and PCT application no. PCT/US2005/036951, which are herein incorporated by reference in their entireties.

STATEMENT REGARDING FEDERALLY SPONSORED RESEARCH OR DEVELOPMENT

This invention was funded through two grants, including an NIH subcontract from Duke University (Subcontract No. SPSID 126632) and a Human Frontier Science Program grant (Contract No. RGP0041/2004C). This invention was also funded by DOE Grant No. DE-FG02-04ER15542 and by NIH Grant No. 1 R33 DK070272. Accordingly the U.S. Government has certain rights to this invention.

FIELD OF INVENTION

The invention relates generally to the field of molecular biology and metabolomics. More specifically, the invention relates to biosensors and methods for measuring and detecting ligand binding using intramolecular fluorescence resonance energy transfer (FRET).

BACKGROUND OF INVENTION

All publications and patent applications herein are incorporated by reference to the same extent as if each individual publication or patent application was specifically and individually indicated to be incorporated by reference.

The publications discussed herein are provided solely for their disclosure prior to the filing date of the present application. Nothing herein is to be construed as an admission that the present invention is not entitled to antedate such publication by virtue of prior invention.

The field of metabolomics centers on the metabolic and biochemical events associated with a cellular or biological system. Metabolomics seeks to depict the steady-state physiological state of a cell or organism as well as dynamic responses of a cell or organism to genetic and environmental modulation. Metabolomic tools permit the detection of disease states, the monitoring of disease progression and patient response to therapy, the classification of patients based on biochemical profiles and the identification of targets for drug design.

An ideal metabolomic tool reveals the concentration of a particular molecular species of interest in a physiological environment. It allows one to visualize how its concentration varies across an organ, tissue or cell. It permits the detection of metabolite levels and the changes in metabolite levels in response to environmental stimuli, and allows these changes to be monitored in real time. Using various such tools should permit multiple analytes to be measured simultaneously, even analytes of different structural and functional classes.

No currently available technology addresses all these issues in a satisfactory manner. Non-aqueous fractionation is static, invasive, has no cellular resolution and is sensitive to artifacts, while spectroscopic methods such as NMRi (nuclear magnetic resonance imaging) and PET (positron emission tomography) provide dynamic data, but poor spatial resolution. The development of genetically encoded molecular sensors, which transduce an interaction of the target molecule with a recognition element into a macroscopic observable format, via allosteric regulation of one or more signaling elements, may facilitate some of the goals.

The most common reporter element employed in molecular sensors is a sterically separated donor-acceptor FRET pair of fluorescent proteins (GFP spectral variants or otherwise) (Fehr et al., 2002, Proc. Natl. Acad. Sci USA 99: 9846-51), although single fluorescent proteins (Doi and Yanagawa, 1999, FEBS Lett. 453: 305-7), enzymes (Guntas and Ostermeier, 2004, J. Mol. Biol. 336: 263-73) and bioluminescent molecules (Xu et al., 1999, Proc. Natl. Acad. Sci. USA 96: 151-56) have been used as well. FRET (fluorescence resonance energy transfer) refers to a quantum mechanical effect between a given pair of chromophores, consisting of a fluorescence donor and respective acceptor. Prerequisites for FRET are proximity of donor and acceptor, and overlap between the donor emission spectrum and the acceptor excitation spectrum. When the donor and acceptor are in close enough vicinity, the emission of the excited donor decreases while emission of the sensitized acceptor increases (see Fehr et al., 2004, Current Opinion in Plant Biology 7: 345-51, herein incorporated by reference in its entirety).

There are two general types of FRET used by biosensors: intermolecular and intramolecular (Truong and Ikura, 2001, Current Opinion in Structural Biology 11: 573-78, herein incorporated by reference). Intermolecular FRET occurs when the fluorescent donor and acceptor molecules are on different macromolecules. This form of FRET is difficult to quantitate because the stoichiometry of acceptors to donors can vary with transfection efficiencies and expression levels. Nevertheless, several examples of intermolecular FRET have been reported (for a review, see Truong and Ikura, 2001; and Wouters et al., 2001, TRENDS in Cell Biol. 11(5): 203-11).

Intramolecular FRET occurs when both the donor and acceptor molecules are fused to the same molecule. In this type of sensor, the binding domains must undergo conformational changes that are large enough to translate metabolite binding into a change in FRET. Ideally, sensor families should share similar three-dimensional structures but have different substrate specificities that cover a wide spectrum of substrates. Furthermore, ultra-high-affinity binding in the nanomolar range would facilitate the engineering of mutant "nanosensors" for different physiological detection ranges by site-directed mutagenesis.

Some molecular sensors additionally employ a conformational actuator (most commonly a peptide which binds to one conformational state of the recognition element), to magnify the allosteric effect upon and resulting output of the reporter element (i.e., Miyakawa et al., 1997, Nature 388: 882-87). The applicability of the method in the absence of a conformational actuator, and its generalizability to a variety of analytes, has recently been demonstrated using bacterial periplasmic binding proteins (PBPs) (Fehr et al., 2002; Fehr et al., 2003, J. Biol. Chem. 278: 19127-33; and Lager et al., 2003, FEBS Lett. 553: 85-9).

Members of the bacterial PBP superfamily recognize hundreds of substrates with high affinity (atto- to low micromolar) and specificity (Tam and Saier, 1993, Microbiol. Rev. 57: 320-46). PBPs have been shown by a variety of experimental techniques to undergo a significant conformational change upon ligand binding. Fusion of individual sugar-binding PBPs with a pair of GFP variants has produced sensors for maltose, ribose and glucose (Fehr et al., 2002; Fehr et al., 2003; and Lager et al., 2003). Moreover, PBPs bind substrates with affinities in the nanomolar range (Fehr et al., 2004). Thus, PBPs satisfy many of the criteria important for an ideal biosensor. The sensors have been used to measure sugar uptake and homeostasis in living animal cells, and sub-cellular analyte levels have been determined using nuclear-targeted versions (Fehr et al., 2004, J. Fluoresc. 14: 603-9).

Intramolecular biosensors are typically designed by fusing donor and acceptor fluorescent molecules to the amino and carboxy terminal portions of the sensor domain, respectively, which undergo a venus flytrap-like closure of two lobes upon substrate binding (see, e.g., Fehr et al, 2002; Fehr et al., 2003; Lager et al., 2003; and Truong and Ikura, 2001). Bacterial PBPs comprise two globular domains and are convenient scaffolds for designing FRET sensors (Fehr et al., 2003). The binding site is located in the cleft between the domains, and upon binding, the two domains engulf the substrate and undergo a hinge-twist motion (Quiocho and Ledvina, 1996, Mol. Microbiol. 20: 17-25).

PBPs can be divided into two types based on different topological arrangements of the central β-sheets and position of the termini (Fukami-Kobayashi et al., 1999, J. Mol. Biol. 286: 279-290). Maltose binding protein (MBP) is a type II binding protein, with termini being located at the distal ends of the lobes relative to the hinge region. A comparison of the crystal structures of bound and unbound states shows that the hinge-twist motion brings the termini closer together. As would be expected in the case of maltose sensor, the decrease in distance upon maltose binding leads to increased FRET between attached chromophores (Fehr et al., 2002).

In GGBP (D-GalactoseD-Glucose Binding Protein) (a type I PBP), termini are located at the proximal ends of the two lobes (Fehr et al., 2004). Thus, because of the different chromophore positions, the substrate-induced hinge-twist motion is predicted to move the attached chromophores further apart, causing a decrease in FRET. Nevertheless, type I PBPs such as GGBP have also been used to construct efficient FRET biosensors containing terminally fused donor and acceptor fluorophores (Fehr et al., 2003).

The present inventors have now surprisingly found that fusion of fluorescent domains to internal positions of a ligand binding protein, even within the same lobe of a PBP sensor, facilitates the design of an efficient biosensor that demonstrates a similar ligand affinity and a substantially larger delta ratio than its terminally fused counterpart. This is counterintuitive in view of the general model for intramolecular FRET sensors, wherein the donor and acceptor molecules are fused to separate termini on separate lobes of the protein in order to maximize the change in orientation and/or distance of the donor and acceptor chromophores upon ligand binding.

The improved signal from these sensors can be ascribed to increased rigidity and thus reduced rotational averaging. The invention thus leads to an alternative approach, also disclosed herein, to improve sensors by using more rigidly conjugated reporters. To increase the rigidity and reduce rotational averaging, we deleted portions of the fusion proteins corresponding to residues not belonging to the core structure of the three contributing partners, i.e. omitting linker sequences at the fusion sites and deleting N- or C-terminal portions of either of the three modules. Consistent with the observations made for sensors using fusion of fluorescent domains to internal positions of a ligand binding protein, enhanced terminally fused sensors also showed much increased FRET ratio changes.

SUMMARY OF THE INVENTION

The present invention therefore provides improved intramolecular biosensors and nanosensors for detecting and measuring changes in analyte concentrations, particularly transporter biosensors and biosensors constructed using bacterial periplasmic binding proteins (PBPs). In particular, the invention provides intramolecular biosensors containing at least one internally fused fluorophore moiety, as well as FRET fusion constructs encoding fluorophores with increased rigidity.

For instance, the invention provides an isolated nucleic acid encoding a ligand binding fluorescent indicator comprising a ligand binding protein moiety wherein the ligand binding protein moiety is genetically fused to a donor fluorophore moiety and an acceptor fluorophore moiety, wherein fluorescence resonance energy transfer (FRET) between the donor moiety and the acceptor moiety is altered when the donor moiety is excited and the ligand binds to the ligand binding protein moiety, and wherein at least one of either said donor fluorophore moiety or said acceptor fluorophore moiety is fused to said ligand binding protein moiety at an internal site of said ligand binding protein moiety. In one embodiment, among others, the donor and acceptor fluorophore moieties are fluorescent proteins.

The invention also provides methods of improving the sensitivity of intramolecular biosensors, including terminally and internally fused biosensors. For instance, such methods may comprise the steps of (a) providing an intramolecular FRET biosensor comprising a ligand binding protein moiety, and donor and acceptor fluorescent protein moieties fused to said ligand binding protein moiety, respectively, wherein fluorescence resonance energy transfer (FRET) between the donor moiety and the acceptor moiety is altered when the donor moiety is excited and said ligand binds to the ligand binding protein moiety; and (b) altering or modifying the fusion domain between the fluorophore and ligand binding moieties, wherein said alteration results in an intramolecular FRET biosensor with improved sensitivity as compared to said biosensor without said alteration. The alteration may be an amino acid deletion, insertion or mutation that increases the rigidity of the fluorophore linkage. The invention also encompasses nucleic acid constructs produced by such methods.

Vectors, including expression vectors, and host cells comprising the inventive nucleic acids are also provided, as well as biosensor proteins encoded by the nucleic acids. Such nucleic acids, vectors, host cells and proteins may be used in methods of detecting changes in analyte levels, and in methods of identifying compounds that modulate ligand binding.

BRIEF DESCRIPTION OF THE DRAWINGS

FIG. 13. Diagram showing the various deletions constructed in the coding sequence of FLIPglu 600µ and the corresponding delta ratios obtained.

FIG. 14. Construction of the FLII[12]Pglu-600µ and FLII[275]Pglu-4.6m deletion sensors. The N-terminal ECFP core is boxed blue. The dispensable C-terminal sequences of ECFP are underlined in blue. The flexible linker containing a KpnI restriction enzyme recognition site is shown in black. The mglB core is boxed red, while the dispensable C-terminal residues of mglB are underlined red. The EYFP core is boxed yellow, while the dispensable N-terminal residues are underlined yellow. Construct names are labeled on the left.

DETAILED DESCRIPTION OF INVENTION

Figure 1:
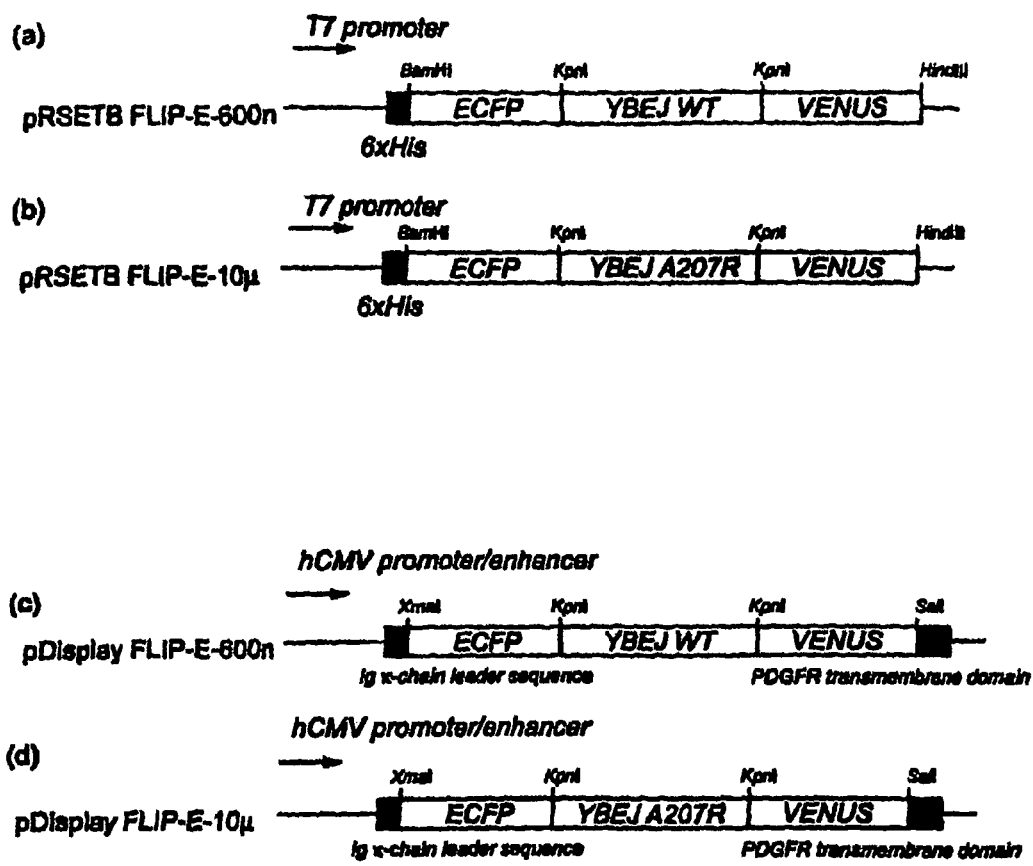
FIG. 1. YbeJ FLIP-E nanosensor constructs used for expression in *E. coli* (A and B) and neuronal cell culture (C and D) containing terminally fused fluorophores.

The following description includes information that may be useful in understanding the present invention. It is not an admission that any of the information provided herein is prior art or relevant to the presently claimed inventions, or that any publication specifically or implicitly referenced is prior art.

Other objects, advantages and features of the present invention become apparent to one skilled in the art upon reviewing the specification and the drawings provided herein. Thus, further objects and advantages of the present invention will be clear from the description that follows.

Internally Fused Intramolecular Biosensors

As described above, the present inventors have surprisingly found that fusion of fluorescent domains to internal positions of a ligand binding protein, even within the same lobe of a PBP sensor, facilitates the design of an efficient biosensor that demonstrates a similar ligand affinity and a substantially larger delta ratio than its terminally fused counterpart. This is counterintuitive in view of the general model for intramolecular FRET sensors, wherein the donor and acceptor molecules are typically fused to the termini on separate lobes of the protein in order to maximize the change in orientation and/or distance of the donor and acceptor chromophores upon ligand binding.

Without being bound to any particular theory, the present inventors believe that the data supports the prediction that rotational movements play a key role in FRET. The dipoles must be oriented in a certain position to each other for efficient resonance energy transfer. However, with terminally fused donor and acceptor moieties, one commonly assumes that the peptide bonds in the linker between the three moieties are freely rotating, thus randomizing this parameter, within a cone of steric compatibility. By inserting the fluorescent moiety into an internal position of the PBP, free or limited free rotation of the fluorophore around the peptide axis in the linker sequences is prevented, or greatly reduced. Thus, in an internal fusion, the fluorescent moiety is rigidly inserted at both ends, thereby reducing free rotation and possibly explaining the higher observed delta ratio. Alternatively, more rigidly fused chromophores enable enhanced allosteric coupling between the conformational change of the binding protein and the motion of the chromophore.

Thus, the biosensors of the present invention exhibit surprisingly enhanced activities over their terminally fused counterparts. Moreover, in some cases, internally fused donor and acceptor molecules permits the measurement of FRET increases upon ligand binding using sensors that typically operate by decreased FRET upon ligand binding, such as GGBP sensors. Thus, the direction of FRET alteration may be changed by using internally fused donor and/or acceptor moieties as compared to terminally fused counterparts.

The present invention encompasses isolated nucleic acids which encode ligand binding fluorescent indicator. An isolated nucleic acid according to the present invention encodes an indicator comprising a ligand binding protein moiety, a donor fluorophore moiety fused to the ligand binding protein moiety, and an acceptor fluorophore moiety fused to the ligand binding protein moiety, wherein fluorescence resonance energy transfer (FRET) between the donor moiety and the acceptor moiety is altered when the donor moiety is excited and said ligand binds to the ligand binding protein moiety, and wherein at least one of either or both of said donor fluorophore moiety and/or said acceptor fluorophore moiety are fused to said ligand binding protein moiety at an internal site of said ligand binding protein moiety.

Either the donor fluorophore moiety or the acceptor fluorophore moiety or both may be fused to an internal site of said ligand binding protein moiety. Preferably, the donor and acceptor moieties are not fused in tandem, although the donor and acceptor moieties may be contained on the same protein domain or lobe. A domain is a portion of a protein that performs a particular function and is typically at least about 40 to about 50 amino acids in length. There may be several protein domains contained in a single protein. A "ligand binding protein moiety" according to the present invention can be a complete, naturally occurring protein sequence, or at least the ligand binding portion or portions thereof. In preferred embodiments, among others, a ligand binding moiety of the invention is at least about 40 to about 50 amino acids in length, or at least about 50 to about 100 amino acids in length, or more than about 100 amino acids in length.

Methods of Improving Sensitivity of Fret Biosensors

As described above, the invention also provides methods of improving the sensitivity of intramolecular biosensors, including terminally and internally fused biosensors. For instance, such methods may comprise the steps of (a) providing an intramolecular FRET biosensor comprising a ligand binding protein moiety, and donor and acceptor fluorescent protein moieties fused to the two termini of said ligand binding protein moiety, respectively, wherein fluorescence resonance energy transfer (FRET) between the donor moiety and the acceptor moiety is altered when the donor moiety is excited and said ligand binds to the ligand binding protein moiety; and (b) altering or modifying the fusion domain between the fluorophore and ligand binding moieties, wherein said alteration results in an intramolecular FRET biosensor with improved sensitivity as compared to said biosensor without said alteration. The alteration may be a deletion, insertion or mutation of one or more amino acids from the linker, fluorophore or ligand binding domains that increases the rigidity of the fluorophore linkage.

The disclosed methods of improving FRET biosensor sensitivity stem from the present inventors' observations regarding internally fused FRET sensors. Having learned that the reduced rotational averaging in the intramolecular insertion of a fluorophores is a general strategy to generate sensors with high ratio changes, we hypothesized that one may obtain similar results by reducing the rotational freedom of the linkage between the analyte binding domain and the fluorophores. To test the hypothesis, we systematically removed sequences that connect the core protein structure of the binding domain and the fluorophore, i.e. by removing linker sequences and/or by deleting amino acids from the ends of the analyte binding moiety and/or the fluorophores. We found that the closer coupling achieved by such deletions also leads to higher ratio changes. This concept is exemplified herein for glucose binding constructs, but is applicable to any FRET-based biosensor.

Preferably, deletions are made by deleting at least one, or at least two, or at least three, or at least four, or at least five, or at least eight, or at least ten, or at least fifteen nucleotides in a nucleic acid construct encoding said intramolecular FRET biosensor that are located in the regions encoding the linker, or fluorophore, or ligand binding domains. Deletions in different regions may be combined in a single construct to create more than one region demonstrating increased rigidity. Amino acids may also be added or mutated to increase rigidity of the biosensor and improve sensitivity. For instance, by introducing a kink by adding a proline residue or other suitable amino acid. Improved sensitivity is measured by the ratio change in FRET fluorescence upon ligand binding, and preferably increases by at least a factor of 2 as a result of said deletion.

The invention also encompasses nucleic acid constructs produced by such methods, as well as vectors and cells containing the nucleic acids as described herein. The FRET biosensors encoded by the nucleic acid constructs are also included.

Ligand Binding Moieties

Preferred ligand binding protein moieties according to the present invention, among others, are transporter proteins and ligand binding sequences thereof, for instance transporters selected from the group consisting of channels, uniporters, coporters and antiporters. Also preferred are periplasmic binding proteins (PBP), such as any of the bacterial PBPs included in Table 1 below. As described above, bacterial PBPs comprise two globular domains or lobes and are convenient scaffolds for designing FRET sensors (Fehr et al., 2003). The binding site is located in the cleft between the domains, and upon binding, the two domains engulf the substrate and undergo a hinge-twist motion (Quiocho and Ledvina, 1996, Mol. Microbiol. 20: 17-25). In type I PBPs, such as GGBP (D-GalactoseD-Glucose Binding Protein), the termini are located at the proximal ends of the two lobes that move apart upon ligand binding (Fehr et al., 2004). In type II PBPs, such as Maltose Binding Protein (MBP), the termini are located at the distal ends of the lobes relative to the hinge region and come closer together upon ligand binding. Thus, depending on the type of PBP and/or the position of the internally fused donor or acceptor moiety, FRET may increase or decrease upon ligand binding and both instances are included in the present invention.

TABLE 1

Bacterial Periplasmic Binding Proteins

| Gene name | Substrate | Species | 3D | Reference |
|---|---|---|---|---|
| AccA | agrocinopine | *Agrobacterium* sp. | —/— | J. Bacteriol. (1997) 179, 7559-7572 |
| AgpE | alpha-glucosides (sucrose, maltose, trehalose) | *Rhizobium meliloti* | —/— | J. Bacteriol. (1999) 181, 4176-4184 |
| AlgQ2 | alginate | *Sphingomonas* sp. | —/c | J. Biol. Chem. (2003) 278, 6552-6559 |
| AlsB | allose | *E. coli* | —/c | J. Bacteriol. (1997) 179, 7631-7637 |
|  |  |  |  | J. Mol. Biol. (1999) 286, 1519-1531 |
| AraF | arabinose | *E. coli* | —/c | J. Mol. Biol. (1987) 197, 37-46 |
|  |  |  |  | J. Biol. Chem. (1981) 256, 13213-13217 |

TABLE 1-continued

Bacterial Periplasmic Binding Proteins

| Gene name | Substrate | Species | 3D | Reference |
|---|---|---|---|---|
| AraS | arabinose/fructose/xylose | *Sulfolobus solfataricus* | —/— | Mol. Microbiol. (2001) 39, 1494-1503 |
| ArgT | lysine/arginine/ornithine | *Salmonella typhimurium* | o/c | Proc. Natl. Acad. Sci. USA (1981) 78, 6038-6042 |
| | | | | J. Biol. Chem. (1993) 268, 11348-11355 |
| ArtI | arginine | *E. coli* | | Mol. Microbiol. (1995) 17, 675-686 |
| ArtJ | arginine | *E. coli* | | Mol. Microbiol. (1995) 17, 675-686 |
| b1310 | (putative, multiple sugar) | *E. coli* | —/— | NCBI accession A64880 |
| b1487 | (putative, oligopeptide binding) | *E. coli* | —/— | NCBI accession B64902 |
| b1516 | (sugar binding protein homolog) | *E. coli* | —/— | NCBI accession G64905 |
| BtuF | vitamin B12 | *E. coli* | —/— | J. Bacteriol. (1986) 167, 928-934 |
| CAC1474 | proline/glycine/betaine | *Clostridium acetobutylicum* | —/— | NCBI accession AAK79442 |
| cbt | dicarboxylate (succinate, malate, fumarat) | *E. coli* | —/— | J. Supramol. Struct. (1977) 7, 463-80 |
| | | | | J. Biol. Chem. (1978) 253, 7826-7831 |
| | | | | J. Biol. Chem. (1975) 250, 1600-1602 |
| CbtA | cellobiose | *Sulfoblobus solfataricus* | —/— | Mol. Microbiol. (2001) 39, 1494-1503 |
| ChvE | sugar | *Agrobacterium tumefaciens* | —/— | J. Bacteriol. (1990) 172, 1814-1822 |
| CysP | thiosulfate | *E. coli* | —/— | J. Bacteriol. (1990) 172, 3358-3366 |
| DctP | C4-dicarboxylate | *Rhodobacter capsulatus* | —/— | Mol. Microbiol. (1991) 5, 3055-3062 |
| DppA | dipeptides | *E. coli* | o/c | Biochemistry (1995) 34, 16585-16595 |
| FbpA | iron | *Neisseria gonorrhoeae* | —/c | J. Bacteriol. (1996) 178, 2145-2149 |
| FecB | Fe(III)-dicitrate | *E. coli* | | J. Bacteriol. (1989) 171, 2626-2633 |
| FepB | enterobactin-Fe | *E. coli* | —/— | J. Bacteriol. (1989) 171, 5443-5451 |
| | | | | Microbiology (1995) 141, 1647-1654 |
| FhuD | ferrichydroxamate | *E. coli* | —/c | Mol. Gen. Genet. (1987) 209, 49-55 |
| | | | | Nat. Struct. Biol. (2000) 7, 287-291 |
| | | | | Mol. Gen. Genet. (1987) 209, 49-55 |
| FliY | cystine | *E. coli* | —/— | J. Bacteriol. (1996) 178, 24-34 |
| | | | | NCBI accession P39174 |
| GlcS | glucose/galactose/mannose | *Sulfolobus solfataricus* | —/— | Mol. Microbiol. (2001) 39, 1494-1503 |
| GlnH (protein: GLNBP) | glutamine | *E. coli* | o/— | Mol. Gen. Genet. (1986) 205, 260-9 |
| | | | | J. Mol. Biol. (1996) 262, 225-242 |
| | | | | J. Mol. Biol. (1998) 278, 219-229 |
| GntX | gluconate | *E. coli* | —/— | J. Basic. Microbiol. (1998) 38, 395-404 |
| HemT | haemin | *Yersinia enterocolitica* | —/— | Mol. Microbiol. (1994) 13, 719-732 |
| HisJ (protein: HBP) | histidine | *E. coli* | —/c | Biochemistry (1994) 33, 4769-4779 |
| HitA | iron | *Haemophilus influenzae* | o/c | Nat. Struct. Biol. (1997) 4, 919-924 |
| | | | | Infect. Immun. (1994) 62, 4515-25 |
| | | | | J. Biol. Chem. (195) 270, 25142-25149 |
| LivJ | leucine/valine/isoleucine | *E. coli* | —/c | J. Biol. Chem. (1985) 260, 8257-8261 |
| | | | | J. Mol. Biol. (1989) 206, 171-191 |
| LivK (protein: LBP) | leucine | *E. coli* | —/c | J. Biol. Chem. (1985) 260, 8257-8261 |
| | | | | J. Mol. Biol. (1989) 206, 193-207 |
| MalE (protein: MBP) | maltodextrine/maltose | *E. coli* | o/c | Structure (1997) 5, 997-1015 |
| | | | | J. Bio. I Chem. (1984) 259, 10606-13 |
| MglB (protein: GGBP) | glucose/galactose | *E. coli* | —/c | J. Mol. Biol. (1979) 133, 181-184 |
| | | | | Mol. Gen. Genet. (1991) 229, 453-459 |
| ModA | molybdate | *E. coli* | —/c | Nat. Struct. Biol. (1997) 4, 703-707 |
| | | | | Microbiol. Res. (1995) 150, 347-361 |
| MppA | L-alanyl-gamma-D-glutamyl-meso-diaminopimelate | *E. coli* | | J. Bacteriol. (1998) 180, 1215-1223 |
| NasF | nitrate/nitrite | *Klebsiella oxytoca* | —/— | J. Bacteriol. (1998) 180, 1311-1322 |
| NikA | nickel | *E. coli* | —/— | Mol. Microbiol. (1993) 9, 1181-1191 |
| opBC | choline | *Bacillus subtilis* | —/— | Mol. Microbiol. (1999) 32, 203-216 |
| OppA | oligopeptide | *Salmonella typhimurium* | o/c | Biochemistry (1997) 36, 9747-9758 |
| | | | | Eur. J. Biochem. (1986) 158, 561-567 |
| PhnD | alkylphosphonate | *E. coli* | —/— | J. Biol. Chem. (1990) 265, 4461-4471 |
| PhoS (Psts) | phosphate | *E. coli* | —/c | J. Bacteriol. (1984) 157, 772-778 |
| | | | | Nat. Struct. Biol. (1997) 4, 519-522 |
| PotD | putrescine/spermidine | *E. coli* | —/c | J. Biol. Chem. (1996) 271, 9519-9525 |
| PotF | polyamines | *E. coli* | —/c | J. Biol. Chem. (1998) 273, 17604-17609 |
| ProX | betaine | *E. coli* | | J. Biol. Chem. (1987) 262, 11841-11846 |
| rbsB | ribose | *E. coli* | o/c | J. Biol. Chem. (1983) 258, 12952-6 |
| | | | | J. Mol. Biol. (1998) 279, 651-664 |
| | | | | J. Mol. Biol. (1992) 225, 155-175 |
| SapA | peptides | *Salmonella typhimurium* | —/— | EMBO J. (1993) 12, 4053-4062 |
| Sbp | sulfate | *Salmonella typhimurium* | —/c | J. Biol. Chem. (1980) 255, 4614-4618 |
| | | | | Nature (1985) 314, 257-260 |
| TauA | taurin | *E. coli* | —/— | J. Bacteriol. (1996) 178, 5438-5446 |
| TbpA | thiamin | *E. coli* | —/— | J. Biol. Chem. (1998) 273, 8946-8950 |

TABLE 1-continued

Bacterial Periplasmic Binding Proteins

| Gene name | Substrate | Species | 3D | Reference |
|---|---|---|---|---|
| TctC | tricarboxylate | Salmonella typhimurium | —/— | |
| ThuE | trehalose/maltose/sucrose | Sinorhizobium meliloti | —/— | J. Bacteriol. (2002) 184, 2978-2986 |
| TreS | trehalose | Sulfolobus solfataricus | —/— | Mol. Microbiol. (2001) 39, 1494-1503 |
| tTroA | zinc | Treponema pallidum | —/c | Gene (1997) 197, 47-64 |
| | | | | Nat. Struct. Biol. (1999) 6, 628-633 |
| UgpB | sn-glycerol-3-phosphate | E. coli | —/— | Mol. Microbiol. (1988) 2, 767-775 |
| XylF | xylose | E. coli | —/— | Receptors Channels (1995) 3, 117-128 |
| YaeC | unknown | E. coli | —/— | J Bacteriol (1992) 174, 8016-22 |
| | | | | NCBI accession P28635 |
| YbeJ(GltI) | glutamate/aspartate (putative, superfamily: lysine-arginine-ornithine-binding protein) | E. coli | —/— | NCBI accession E64800 |
| YdcS (b1440) | (putative, spermidine) | E. coli | —/— | NCBI accession P76108 |
| YehZ | unknown | E. coli | —/— | NCBI accession AE000302 |
| YejA | (putative, homology to periplasmic oligopeptide-binding protein - Helicobacter pylori) | E. coli | —/— | NCBI accession AAA16375 |
| YgiS (b3020) | oligopeptides | E. coli | —/— | NCBI accession Q46863 |
| YhbN | unknown | E. coli | —/— | NCBI accession P38685 |
| YhdW | (putative, amino acids) | E. coli | —/— | NCBI accession AAC76300 |
| YliB (b0830) | (putative, peptides) | E. coli | —/— | NCBI accession P75797 |
| YphF | (putative sugars) | E. coli | —/— | NCBI accession P77269 |
| Ytrf | acetoin | B. subtilis | —/— | J. Bacteriol. (2000) 182, 5454-5461 |
| ZnuA | zinc | Synechocystis | —/— | J. Mol. Biol. (2003) 333, 1061-1069 |

Bacterial PBPs have the ability to bind a variety of different molecules and nutrients, including sugars, amino acids, vitamins, minerals, ions, metals and peptides, as shown in Table 1. Thus, PBP-based ligand binding sensors may be designed to permit detection and quantitation of any of these molecules according to the methods of the present invention. Naturally occurring species variants of the PBPs listed in Table 1 may also be used, in addition to artificially engineered variants comprising site-specific mutations, deletions or insertions that maintain measurable ligand binding function. Variant nucleic acid sequences suitable for use in the nucleic acid constructs of the present invention will preferably have at least 70, 75, 80, 85, 90, 95, or 99% similarity or identity to the native gene sequence for a given PBP.

Suitable variant nucleic acid sequences may also hybridize to the gene for a PBP under highly stringent hybridization conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

Preferred biosensors of the present invention, among others, include glutamate sensors constructed using YbeJ binding domains, and other amino acid biosensors. Such proteins may be used as neurotransmitter biosensors for detecting and measuring changes in neurotransmitter concentrations using Fluorescence Resonance Energy Transfer (FRET) (see U.S. provisional applications 60/618,179, herein incorporated by reference in their entirety). The three major categories of substances that act as neurotransmitters are (1) amino acids (primarily glutamic acid or glutamate, GABA, aspartic acid & glycine), (2) peptides (vasopressin, somatostatin, neurotensin, etc.) and (3) monoamines (norepinephrine, dopamine & serotonin) plus acetylcholine. In particular, the invention provides glutamate binding fluorescent indicators, particularly indicators comprising a glutamate binding protein moiety from the *Escherichia coli* glutamate/aspartate receptor, YbeJ. Additional neurotransmitter biosensors for the neurotransmitters listed above may also be prepared using the constructs and methods provided herein.

YbeJ is also known in the art as YzzK and GltI, and its DNA sequence (SEQ ID No. 27) and protein sequence (YbeJ, protein accession no. NP_415188, SEQ ID No. 28) are known. SEQ ID Nos. 1 and 2 provide alternative nucleic acid and protein sequences for YbeJ, respectively, and include additional upstream material that may be part of the full length protein. Naturally occurring homologues from other bacterial species may also be used, for instance the PA5082 gene from *Pseudomonas aeruginosa*, whose gene product is 70% similar to the YbeJ protein from *E. coli*. Any portion of the YbeJ DNA sequence which encodes a glutamate binding region may be used in the nucleic acids of the present invention. Glutamate binding portions of YbeJ or any of its homologues may be cloned into the vectors described herein and screened for activity according to the disclosed assays.

For instance, one region that is suitable for use in the nucleic acids of the present invention is provided by SEQ ID No. 3, which encodes a truncated glutamate-aspartate binding protein sequence (SEQ ID No. 4), encoding mature protein without signal peptide. A preferred internally fused intramolecular sensor according to the present invention comprises a fluorescent protein moiety inserted between amino acids corresponding to amino acids 58 and 59, and amino acid 216 and 217 of SEQ ID No. 28. In preferred embodiments, the donor fluorescent protein moiety is eCFP, however any of the donor moieties described herein may be used. In such sensors, the acceptor fluorescent protein moiety is preferably YFP VENUS or cpVenus, inserted at the C-terminus of said glutamate binding protein moiety or internally fused to said glutamate binding protein. Further, other acceptor moieties may be used, as described herein.

Preferred artificial variants of the sensors of the present invention may exhibit increased or decreased affinity for ligands, in order to expand the range of ligand concentration that can be measured. For instance, preferred artificial variants for YbeJ sensors include, among others, glutamate binding regions comprising the mutations A207G, A207P, A207K, A207M, A207S, A207C, A207R, A207V, A207L, A207Q, A207T, A207F, A207Y, A207N, A207W, A207H, A207D, and S95W. Additional artificial variants showing decreased or increased binding affinity for glutamate may be constructed by random or site-directed mutagenesis and other known mutagenesis techniques, and cloned into the vectors described herein and screened for activity according to the disclosed assays.

The sensors of the invention may also be designed with a reporter element different from a donor/acceptor pair of FRET-compatible fluorescent proteins. For instance, the ligand-binding moiety of the sensor may be fused with an enzyme in such a manner to create an allosterically regulated enzyme whose activity is regulated by a specified ligand (Guntas and Ostermeier, 2004, J. Mol. Biol. 336(1): 263-73). In addition, such an allosterically-regulated reporter domain may be divided into two or more separate and complementing halves, e.g. complementing fragments of β-lactamase (Galarneau et al., 2002, Nature Biotechnol. 20: 619-622) or of GFP (Cabantous et al., 2005, Nature Biotechnol. 23: 102-107). Any and all reporter element fragments may be fused with the ligand-binding moiety in either an end-to-end fashion (e.g. a typical fusion protein) or inserted internally into the sequence of the ligand-binding moiety (e.g. an internally-fused fluorescent protein as described herein).

Other preferred PBPs to be used in the present invention include sugar binding proteins, such as maltose binding protein (MBP) and galactose/glucose binding protein (GGBP). Glucose sensors, such as GGBP sensors of the present invention, may be used for measuring blood glucose levels, for instance in diabetes or pregnancy. Other preferred ligand-binding moieties which provide a global conformational change in response to ligand binding include, but are not limited to, nuclear hormone receptors, lipocalins, fatty acid-binding proteins, and antibodies. Also possible are inactivated enzymes, including but not limited to, hexokinase, glucokinase, ribokinase, and any other conformationally responsive enzyme or enzyme domain.

General Materials and Methods

The isolated nucleic acids of the invention may incorporate any suitable donor and acceptor fluorescent protein moieties that are capable in combination of serving as donor and acceptor moieties in FRET. Preferred donor and acceptor moieties are selected from the group consisting of GFP (green fluorescent protein), CFP (cyan fluorescent protein), BFP (blue fluorescent protein), YFP (yellow fluorescent protein), and enhanced variants thereof, with a particularly preferred embodiment provided by the donor/acceptor pair CFP/YFP-Venus, a variant of YFP with improved pH tolerance and maturation time (Nagai, T., Ibata, K., Park, E. S., Kubota, M., Mikoshiba, K., and Miyawaki, A. (2002) A variant of yellow fluorescent protein with fast and efficient maturation for cell-biological applications. Nat. Biotechnol. 20, 87-90). An alternative is the MiCy/mKO pair with higher pH stability and a larger spectral separation (Karasawa S, Araki T, Nagai T, Mizuno H, Miyawaki A. Cyan-emitting and orange-emitting fluorescent proteins as a donor/acceptor pair for fluorescence resonance energy transfer. Biochem J. 2004 381:307-12). Also suitable as either a donor or acceptor is native DsRed from a *Discosoma* species, an ortholog of DsRed from another genus, or a variant of a native DsRed with optimized properties (e.g. a K83M variant or DsRed2 (available from Clontech)). Criteria to consider when selecting donor and acceptor fluorescent moieties are known in the art, for instance as disclosed in U.S. Pat. No. 6,197,928, which is herein incorporated by reference in its entirety.

As used herein, the term "variant" is intended to refer to polypeptides with at least about 70%, more preferably at least 75% identity, including at least 80%, 90%, 95% or greater identity to native fluorescent molecules. Many such variants are known in the art, or can be readily prepared by random or directed mutagenesis of native fluorescent molecules (see, for example, Fradkov et al., FEBS Lett. 479:127-130 (2000)).

When the fluorophores of the biosensor contain stretches of similar or related sequence(s), the present inventors have recently discovered that gene silencing may adversely affect expression of the biosensor in certain cells and particularly whole organisms. In such instances, it is possible to modify the fluorophore coding sequences at one or more degenerate or wobble positions of the codons of each fluorophore, such that the nucleic acid sequences of the fluorophores are modified but not the encoded amino acid sequences. Alternative, one or more conservative substitutions that do not adversely affect the function of the fluorophores may also be incorporated. See PCT application PCT/US2005/036953, "Methods of Reducing Repeat-Induced Silencing of Transgene Expression and Improved Fluorescent Biosensors], which is herein incorporated by reference in its entirety.

It is also possible to use dyes for FRET, alone or in combination with one or more of the fluorophores listed above, including but not limited to TOTO dyes (Laib and Seeger, 2004, J Fluoresc. 14(2):187-91), Cy3 and Cy5 (Churchman et al., 2005, Proc Natl Acad Sci USA. 102(5): 1419-23), Texas Red, fluorescein, and tetramethylrhodamine (TAMRA) (Unruh et al., Photochem Photobiol. 2004 Oct. 1), AlexaFluor 488, to name a few, as well as fluorescent tags (see, for example, Hoffman et al., 2005, Nat. Methods 2(3): 171-76).

It is also possible to use luminescent quantum dots (QD) or pebble-coupled approaches for FRET (Clapp et al., 2005, J. Am. Chem. Soc. 127(4): 1242-50; Medintz et al., 2004, Proc. Natl. Acad. Sci. USA 101(26): 9612-17; Buck et al., 2004, Curr. Opin. Chem. Biol. 8(5): 540-6), including Surface-Enhanced Raman Scattering, where sensors are bound to the surface of nanoparticles and detection is achieved by Raman spectroscopy (Haes and Van Duyne, 2004, Expert Rev. Mol. Diagn. 4(4): 527-37).

Bioluminescence resonance energy transfer (BRET) may also be used for both in vitro and in vivo measurements, and offers the advantages of FRET without the consequences of fluorescence excitation. BRET is a naturally occurring phenomenon. For instance, when the photoprotein aequorin is purified from the jellyfish, Aequorea, it emits blue light in the absence of GFP, but when GFP and aequorin are associated as they are in vivo, GFP accepts the energy from aequorin and emits green light. In BRET, the donor fluorophore of the FRET technique is replaced by a luciferase. In the presence of a substrate, bioluminescence from the luciferase excites the acceptor fluorophore through the same Forster resonance energy transfer mechanisms described above. Thus, by using a luciferase/GFP mutant or other fluorophore combination, BRET can be used to measure protein interactions both in vivo and in vitro (see Xu et al, 1999, Proc. Natl. Acad. Sci. USA 96: 151-56, which is herein incorporated by reference).

The invention further provides vectors containing isolated nucleic acid molecules encoding improved and internally fused biosensor polypeptides as disclosed herein. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. Such vectors include expression vectors containing expression control sequences operatively linked to the nucleic acid sequence coding for the neurotransmitter biosensor. Vectors may be adapted for function in a prokaryotic cell, such as *E. coli* or other bacteria, or a eukaryotic cell, including yeast and animal cells. For instance, the vectors of the invention will generally contain elements such as an origin of replication compatible with the intended host cells, one or more selectable markers compatible with the intended host cells and one or more multiple cloning sites. The choice of particular elements to include in a vector will depend on factors such as the intended host cells, the insert size, whether regulated expression of the inserted sequence is desired, i.e., for instance through the use of an inducible or regulatable promoter, the desired copy number of the vector, the desired selection system, and the like. The factors involved in ensuring compatibility between a host cell and a vector for different applications are well known in the art.

Preferred vectors for use in the present invention will permit cloning of the ligand binding domain or receptor genetically fused to nucleic acids encoding donor and acceptor fluorescent molecules, resulting in expression of a chimeric or fusion protein comprising the ligand binding domain genetically fused to donor and acceptor fluorescent molecules. Exemplary vectors include the bacterial pRSET-FLIP derivatives disclosed in Fehr et al. (2002) (Visualization of maltose uptake in living yeast cells by fluorescent nanosensors. Proc. Natl. Acad. Sci. USA 99, 9846-9851), which is herein incorporated by reference in its entirety. Methods of cloning nucleic acids into vectors in the correct frame so as to express fusion proteins are well known in the art.

The chimeric internally fused nucleic acids of the present invention are preferably constructed such that either or both the donor and acceptor fluorescent moiety coding sequences are fused to internal positions of the ligand binding protein sequence upon expression in a manner such that changes in FRET between donor and acceptor may be detected upon ligand binding. Fluorescent domains can optionally be separated from the ligand binding domain by one or more flexible linker sequences. Such linker moieties are preferably between about 1 and 50 amino acid residues in length, and more preferably between about 1 and 30 amino acid residues. Linker moieties and their applications are well known in the art and described, for example, in U.S. Pat. Nos. 5,998,204 and 5,981,200, and Newton et al., Biochemistry 35:545-553 (1996). Alternatively, shortened versions of the fluorophores or the binding proteins described herein may be used.

The invention also includes host cells transfected with a vector or an expression vector of the invention, including prokaryotic cells, such as *E. coli* or other bacteria, or eukaryotic cells, such as yeast cells or animal cells. In another aspect, the invention features a transgenic non-human animal having a phenotype characterized by expression of the nucleic acid sequence coding for the expression of the biosensor. The phenotype is conferred by a transgene contained in the somatic and germ cells of the animal, which may be produced by (a) introducing a transgene into a zygote of an animal, the transgene comprising a DNA construct encoding the biosensor; (b) transplanting the zygote into a pseudopregnant animal; (c) allowing the zygote to develop to term; and (d) identifying at least one transgenic offspring containing the transgene. The step of introducing of the transgene into the embryo can be by introducing an embryonic stem cell containing the transgene into the embryo, or infecting the embryo with a retrovirus containing the transgene. Transgenic animals of the invention include transgenic *C. elegans* and transgenic mice and other animals.

The present invention also encompasses isolated improved and internally fused biosensor molecules having the properties described herein, particularly PBP-based fluorescent indicators. Such polypeptides are preferably recombinantly expressed using the nucleic acid constructs described herein. The expressed polypeptides can optionally be produced in and/or isolated from a transcription-translation system or from a recombinant cell, by biochemical and/or immunological purification methods known in the art. The polypeptides of the invention can be introduced into a lipid bilayer, such as a cellular membrane extract, or an artificial lipid bilayer (e.g. a liposome vesicle) or nanoparticle.

The present invention includes methods of detecting changes in the levels of ligands in samples, comprising (a) providing a cell expressing a nucleic acid encoding an improved or internally fused sensor according to the present invention and a sample comprising said ligand; and (b) detecting a change in FRET between said donor fluorescent protein moiety and said acceptor fluorescent protein moiety, wherein a change in FRET between said donor moiety and said acceptor moiety indicates a change in the level of said ligand in the sample. The ligand may be any suitable ligand for which a fused FRET biosensor may be constructed, including any of the ligands described herein. Preferably the ligand is one recognized by a PBP, and more preferably a bacterial PBP, such as those included in Table 1 and homologues and natural and artificial variants thereof.

The amino acid binding sensors of the present invention are useful for detecting and measuring changes in the levels of neurotransmitters in the brain or nervous system of an animal, particularly changes in the level of extracellular glutamate, which can be a signal of a disorder or disease associated with glutamate excitotoxicity. In one embodiment, the invention comprises a method of detecting changes in the level of extracellular glutamate in a sample of neurons, comprising (a) providing a cell expressing a nucleic acid encoding a glutamate binding biosensor as described herein and a sample of neurons; and (b) detecting a change in FRET between a donor fluorescent protein moiety and an acceptor fluorescent protein moiety, each covalently attached to the glutamate binding domain, wherein a change in FRET between said donor moiety and said acceptor moiety indicates a change in the level of extracellular glutamate in the sample of neurons. Alternatively, the protein may be produced in a heterologous host, e.g. in bacteria, purified and injected into organs directly or into the intercellular spaces. The protein or derivatives thereof may also be coupled to particles including quantum dots and introduced into cells or compartments.

FRET may be measured using a variety of techniques known in the art. For instance, the step of determining FRET may comprise measuring light emitted from the acceptor fluorescent protein moiety. Alternatively, the step of determining FRET may comprise measuring light emitted from the donor fluorescent protein moiety, measuring light emitted from the acceptor fluorescent protein moiety, and calculating a ratio of the light emitted from the donor fluorescent protein moiety and the light emitted from the acceptor fluorescent protein moiety. The step of determining FRET may also comprise measuring the excited state lifetime of the donor moiety or anisotropy changes (Squire A, Verveer P J, Rocks O, Bastiaens P I. J Struct Biol. 2004 July; 147(1):62-9. Red-edge anisotropy microscopy enables dynamic imaging of homo-FRET between green fluorescent proteins in cells). Such methods are known in the art and described generally in U.S. Pat. No. 6,197,928, which is herein incorporated by reference in its entirety.

The amount of ligand in a sample can be determined by determining the degree of FRET. First the sensor must be introduced into the sample. Changes in ligand concentration can be determined by monitoring FRET changes at time intervals. The amount of ligand in the sample can be quantified for example by using a calibration curve established by titration in vivo.

The sample to be analyzed by the methods of the invention may be contained in vivo, for instance in the measurement of ligand transport on the surface of cells, or in vitro, wherein ligand efflux may be measured in cell culture. Alternatively, a fluid extract from cells or tissues may be used as a sample from which ligands are detected or measured. With amino acid sensors such as glutamate sensors, such measurements may be used to detect extracellular glutamate associated with traumatic injury to said neurons, or as a possible indicator of a neurological disorder associated with glutamate excitotoxicity, including stroke, epilepsy, Huntington disease, AIDS dementia complex, and amyotrophic lateral sclerosis, among others.

Methods for detecting ligands as disclosed herein may be used to screen and identify compounds that may be used to modulate ligand receptor binding. In one embodiment, among others, the invention comprises a method of identifying a compound that modulates binding of a ligand to a receptor, comprising (a) contacting a mixture comprising a cell expressing a biosensor nucleic acid of the present invention and said ligand with one or more test compounds; and (b) determining FRET between said donor fluorescent domain and said acceptor fluorescent domain following said contacting, wherein increased or decreased FRET following said contacting indicates that said test compound is a compound that modulates ligand binding. The term "modulate" generally means that such compounds may increase or decrease or inhibit the interaction of a ligand with the ligand binding domain.

The methods of the present invention may also be used as a tool for high throughput and high content drug screening. For instance, a solid support or multiwell dish comprising the biosensors of the present invention may be used to screen multiple potential drug candidates simultaneously. Thus, the invention comprises a high throughput method of identifying compounds that modulate binding of a ligand to a receptor, comprising (a) contacting a solid support comprising at least one biosensor of the present invention, or at least one cell expressing a biosensor nucleic acid of the present invention, with said ligand and a plurality of test compounds; and (b) determining FRET between said donor fluorescent domain and said acceptor fluorescent domain following said contacting, wherein increased or decreased FRET following said contacting indicates that a particular test compound is a compound that modulates ligand binding.

In one preferred embodiment, among others, the invention provides a method of identifying a compound that modulates glutamate excitotoxicity comprising (a) contacting a glutamate biosensor or a cell expressing a glutamate biosensor as disclosed herein and a sample of neurons with one or more test compounds, and (b) determining FRET between said donor fluorescent domain and said acceptor fluorescent domain following said contacting, wherein increased or decreased FRET following said contacting indicates that said test compound is a compound that modulates glutamate excitotoxicity. The term "modulate" in this embodiment means that such compounds may increase or decrease glutamate excitotoxicity. Compounds that increase glutamate levels are targets for therapeutic intervention and treatment of disorders associated with glutamate excitotoxicity, as described above. Compounds that decrease glutamate levels may be developed into therapeutic products for the treatment of disorders associated with glutamate excitotoxicity.

The targeting of the sensor to the outer leaflet of the plasma membrane is only one embodiment of the potential applications. It demonstrates that the nanosensor can be targeted to a specific compartment. Alternatively, other targeting sequences may be used to express the sensors in other compartments such as vesicles, ER, vacuole, etc.

Expression systems comprise not only rat neurons, but also human cell lines, animal cells and organs, fungi and plant cells. The sensors can also be used to monitor levels of glutamate in fungal and plant organisms where glutamate serves as an important nitrogen compound, but potentially also a signaling molecule. Expression in bacteria may be used to monitor glutamate levels at sites of infection or in compartments in which the bacteria reside or are introduced. Specifically, bacteria or fungi expressing the sensors may serve as biosensors or as tools to identify new pesticides using a similar scheme as outlined for drug screening above.

The biosensors of the present invention can also be expressed on the surface of animal cells to determine the function of neurons. For example, in *C. elegans*, many of the neurons present have not been assigned a specific function. Expression of the biosensors on the surface permits visualization of neuron activity in living worms in response to stimuli, permitting assignment of function and analysis of neuronal networks. Similarly, the introduction of multiphoton probes into the brain of living mice or rats permits imaging these processes. Finally, expression in specific neurons or glia will allow the study of phenomena such as stroke or Alzheimers Disease and the effect of such disorders on glutamate levels inside neuronal cells or on their surface. Moreover, the effect of medication on localized brain areas or neuronal networks can be studied in vivo.

Finally, it is possible to use the sensors as tools to modify ligand binding, and particularly glutamate fluxes, by introducing them as artificial ligand scavengers, for instance presented on membrane or artificial lipid complexes. Artificial glutamate scavengers may be used to manipulate brain or neuron function.

The following examples are provided to describe and illustrate the present invention. As such, they should not be construed to limit the scope of the invention. Those in the art will well appreciate that many other embodiments also fall within the scope of the invention, as it is described hereinabove and in the claims.

EXAMPLES

Example 1

Construction of Nucleic Acids and Vectors

A truncated glutamate-aspartate binding protein sequence (SEQ ID No. 4), encoding mature protein without signal peptide, was amplified by PCR using *E. coli* K12 genomic DNA as a template. The primers used were 5'-ggtaccggag-gcgccgcaggcagcacgctggacaaaatc-3' (SEQ ID No. 5) and 5'-accggtaccggcgccgttcagtgccttgtcattcggttc-3' (SEQ ID No. 6). The PCR fragment was cloned into the KpnI site of digested FLIPma1-25µ (Fehr et al. 2002) in pRSET vector (Invitrogen), exchanging the maltose binding protein sequence with the YbeJ sequence. The resulting plasmid was named pRSET-FLIP-E-600n (SEQ ID NO: 9).

To improve the pH and chloride tolerance and maturation of the sensor protein, the fragment containing the enhanced YFP (EYFP, CLONTECH) sequence in pRSET-FLIP-E-600n was replaced with the coding sequence of Venus, a variant of YFP with improved pH tolerance and maturation time (Nagai, T., Ibata, K., Park, E. S., Kubota, M., Mikoshiba, K., and Miyawaki, A. (2002) A variant of yellow fluorescent protein with fast and efficient maturation for cell-biological applications. Nat. Biotechnol. 20, 87-90). Affinity mutants carrying substitutions A207G, A207P, A207K, A207M, A207S, A207C, A207R, A207V, A207L, A207Q, A207T, A207F, A207Y, A207N, A207W, A207H, A207D, and S95W were created by site-directed mutagenesis (Kunkel, T. A., Roberts, J. D., and Zakour, R. A. (1987). Rapid and efficient site-specific mutagenesis without phenotypic selection. Methods Enzymol. 154, 367-382).

pRSET-FLIP-E constructs (SEQ ID NOs: 9 and 10) were transferred to *E. coli* BL21(DE3)Gold (Stratagene) using electroporation (Sambrook, J., Fritsch, E. F., and Maniatis, T. (1989). Molecular cloning. A laboratory manual. (Cold Spring Harbor N.Y.: Cold Spring Harbor Laboratory Press). FLIP-E proteins expressed in BL21(DE3)Gold strain were extracted and purified as previously described (Fehr et al. 2002). For expression in rat primary neuronal cell culture and PC12 cell culture, FLIP-E 600n (SEQ ID NO: 13) and –10µ cassettes (SEQ ID NO: 14) were cloned into pDisplay (Invitrogen) as follows: XmaI site and SalI site were introduced on the 5'- and 3'-ends of FLIP-E cassette, respectively, by PCR. The primers used were 5'-gagcccgggatggtgagcaagggcgag-gag-3' (SEQ ID No. 7) and 5'-gaggtcgaccttgtacagctcgtccat-gccgag-3' (SEQ ID No. 8). The PCR fragments were sequenced to confirm that there was no additional PCR error, digested with XmaI/SalI, and cloned into the XmaI/SalI sites of the pDisplay vector. Cell cultures were transfected using a modified calcium phosphate transfection protocol (Xia, Z., Dudek, H., Miranti, C. K., and Greenberg, M. E. (1996). Calcium influx via the NMDA receptor induces immediate early gene transcription by a MAP kinase/ERK-dependent mechanism. J. Neurosci. 16, 5425-5436) or Lipofectamine (Invitrogen).

Example 2

In Vitro Characterization of FLIP-E Nanosensors

A DNA fragment encoding the mature YBEJ protein was fused to ECFP and the Venus sequence at the N- and C-termini, respectively (FIG. 1). Emission spectra and substrate titration curves were obtained by using monochromator microplate reader Safire (Tecan, Austria). Excitation filter was 433±12 nm, emission filters for CFP and YFP emission were 485±12, 528±12 nm, respectively. All analyses were done in 20 mM sodium phosphate buffer, pH 7.0.

Figure 2:
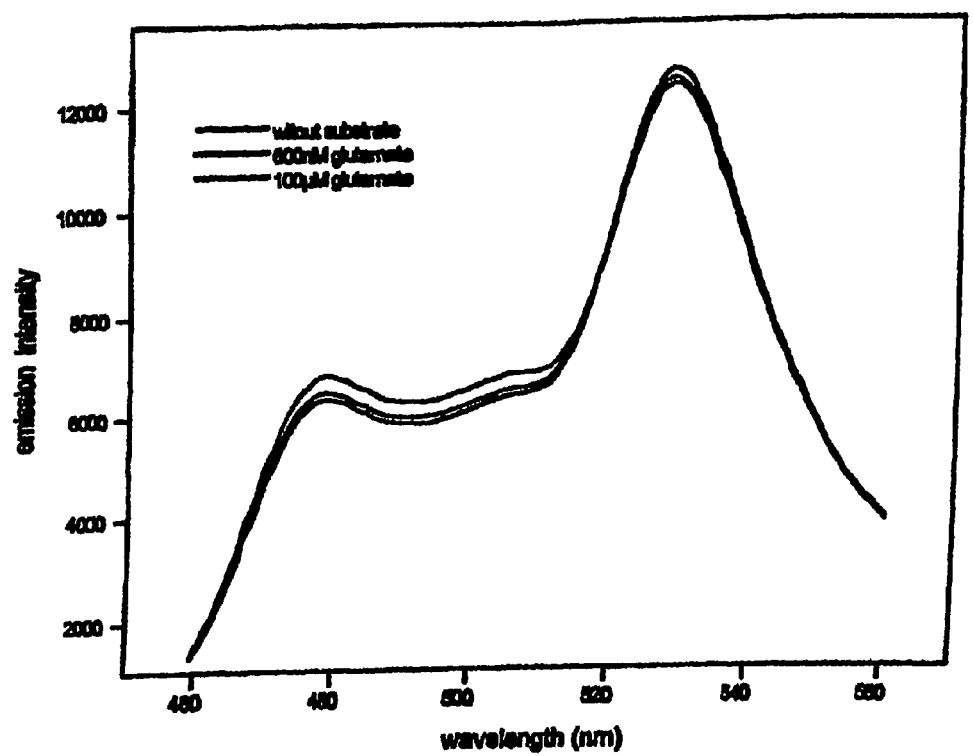
FIG. 2. Spectra of FLIP-E 600n sensor (fluorescent glutamate nanosensor with a $K_d$ for glutamate of 600 nM) at three different concentrations of glutamate: 0 mM (black), at the $K_d$ (blue), and at saturation (red). Curves share an isosbestic point at 520 nm.

Addition of glutamate resulted in an increase in CFP emission and a decrease in YFP emission, suggesting that binding of glutamate to YBEJ results in a conformational change of the chimeric protein potentially due to a relative change in the orientation of the dipoles of the fluorophores (FIG. 2). Since CFP and YFP moieties are assumed to be attached to the same lobe, we speculate that glutamate binding causes the change in dipole-dipole angle of two fluorophores. Interestingly, the ratio and ratio change were in a similar range as compared to other sensors generated so far (Fehr et al., 2002; Fehr et al., 2003; Lager et al., 2003), suggesting that distance changes may not be the primary factor in underlying the mechanisms for FRET changes. Spectra at three different glutamate concentrations (zero, Kd, saturation) reveals an isosbestic point at 520 nm (FIG. 2). The binding constant (Kd) for glutamate was determined to be 600 nM, consistent with data obtained by other methods (de Lorimier et al., 2002). Binding constants for aspartate, glutamine, asparagine were determined to be 6 µM, 100 µM, 300 µM, respectively (see Table 1, below).

In order to expand the range of concentration that can be measured by YBEJ-based glutamate nanosensors, the YBEJ moiety was mutagenized to create nanosensors with lower affinity for glutamate. It has previously been shown that conjugating various fluorophores to sites located at the perimeter of the interdomain cleft that forms the ligand binding site (named "peristeric") changes the ligand-binding affinity in periplasmic binding proteins (de Lorimier et al., 2002). Among the residues tested, mutation of alanine 207 to lysine, methionine, serine, cysteine, arginine, valine, leucine, glutamine, threonine, phenylalanine, tyrosine, aspargine, tryptophan, histidine, aspartate (based on the YbeJ sequence provided in SEQ ID No. 28) lowered the binding affinity significantly (Table 2). In addition, the mutation of serine 95 to tryptophan, which is suggested to interact with the nitrogen of glutamate, was found to decrease the affinity of the protein. Thus, mutations introduced into the FLIPE nanosensor can yield affinity mutants suitable to cover a wide range of physiological glutamate concentrations.

TABLE 2

| Vector | YbeJ moiety | Kd(M) Glutamate | Kd(M) Aspartate | Kd(M) Glutamine | Kd(M) Asparagine |
|---|---|---|---|---|---|
| FLIPE-600n-1 | WT | $6 \times 10^{-7}$ | $6 \times 10^{-6}$ | $1 \times 10^{-4}$ | $3 \times 10^{-4}$ |
| FLIPE-600n-2 | A207G | $6 \times 10^{-7}$ | $4 \times 10^{-6}$ | $2 \times 10^{-4}$ | n.d. |
| FLIPE-600n-3 | A207P | $6 \times 10^{-7}$ | $4 \times 10^{-6}$ | $2 \times 10^{-4}$ | n.d. |
| FLIPE-3µ | A207K | $3 \times 10^{-6}$ | $2 \times 10^{-5}$ | $7 \times 10^{-4}$ | n.d. |
| FLIPE-5µ | A207M | $5 \times 10^{-6}$ | $3 \times 10^{-5}$ | $1 \times 10^{-3}$ | n.d. |
| FLIPE-5µ-2 | A207S | $5 \times 10^{-6}$ | $3 \times 10^{-5}$ | $1 \times 10^{-3}$ | n.d. |
| FLIPE-6µ | A207C | $6 \times 10^{-6}$ | $5 \times 10^{-5}$ | n.d. | n.d. |
| FLIPE-10µ-1 | A207R | $1 \times 10^{-5}$ | $6 \times 10^{-5}$ | $1 \times 10^{-3}$ | n.d. |
| FLIPE-10µ-2 | A207V | $1 \times 10^{-5}$ | $8 \times 10^{-5}$ | $6 \times 10^{-3}$ | n.d. |
| FLIPE-30µ | A207L | $3 \times 10^{-5}$ | n.d. | n.d. | n.d. |
| FLIPE-40µ-1 | A207Q | $4 \times 10^{-5}$ | $2 \times 10^{-4}$ | $7 \times 10^{-3}$ | n.d. |
| FLIPE-40µ-1 | A207T | $4 \times 10^{-5}$ | $1 \times 10^{-4}$ | $7 \times 10^{-3}$ | n.d. |
| FLIPE-100µ-1 | S95W | $1 \times 10^{-4}$ | n.d. | n.d. | n.d. |
| FLIPE-100µ-2 | A207F | $1 \times 10^{-4}$ | $6 \times 10^{-4}$ | n.d. | n.d. |
| FLIPE-300µ | A207Y | $3 \times 10^{-4}$ | $5 \times 10^{-4}$ | n.d. | n.d. |
| FLIPE-400µ | A207N | $4 \times 10^{-4}$ | $1 \times 10^{-3}$ | n.d. | n.d. |
| FLIPE-1m | A207W | $1 \times 10^{-3}$ | n.d. | n.d. | n.d. |
| FLIPE-2m-1 | A207H | $2 \times 10^{-3}$ | $2 \times 10^{-3}$ | n.d. | n.d. |
| FLIPE-2m-2 | A207D | $2 \times 10^{-3}$ | $9 \times 10^{-4}$ | n.d. | n.d. |

Example 3

In Vivo Characterization of FLIP-E

For the in vivo characterization of FLIP-E nanosensors, FLIPE-600n and FLIPE-10μ were cloned into the mammalian expression vector pDisplay (Invitrogen, USA). The pDisplay vector carries a leader sequence which directs the protein to the secretory pathway, and the transmembrane domain which anchors the protein to the plasma membrane, displaying the protein on the extracellular face. Rat hippocampal cells and PC12 cells were transfected with pDisplay FLIPE-600n (SEQ ID NO: 11) and -10μ (SEQ ID NO: 12) constructs. FRET was imaged 24-48 hours after transfection on a fluorescent microscope (DM IRE2, Leica) with a cooled CoolSnap HQ digital camera (Photometrics). Dual emission intensity ratios were simultaneously recorded following excitation at 436 nm and splitting CFP and Venus emission by DualView with the OI-5-EM filter set (Optical Insights) and Metafluor 6.1r1 software (Universal Imaging).

Figure 3:
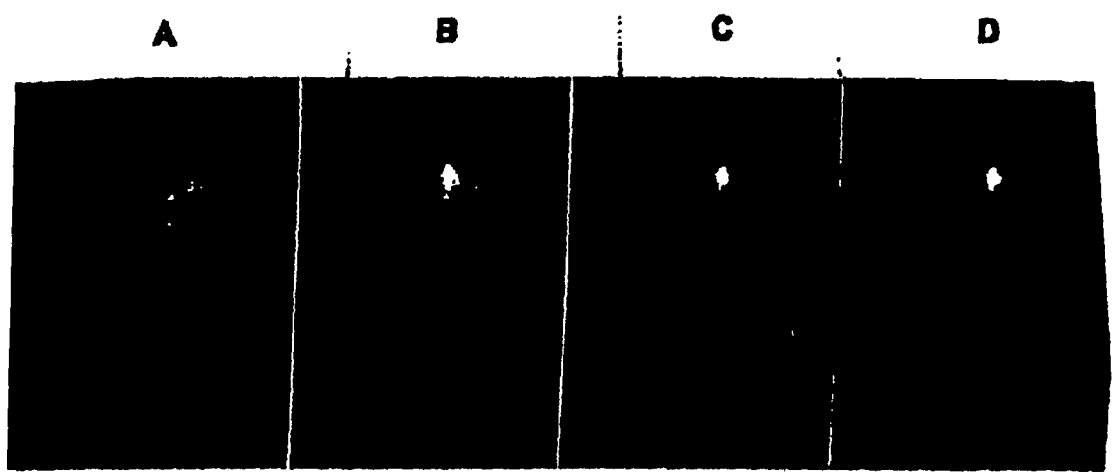
FIG. 3. A hippocampal cell treated with 1 mg/ml trypsin. Images (A-D) were taken at 10 second intervals. Note that signals on the cell surface largely disappear.

The expression of FLIP-E was observed on the plasma membrane of rat hippocampal cell culture, and to some extent also in intracellular compartments, probably in compartments involved in plasma membrane targeting of plasma membrane proteins. When treated with Tyrode's buffer containing 1 mg/mL of trypsin, the majority of fluorescence on the cell surface was eliminated, demonstrating that the FLIPE protein was indeed displayed on the extracellular face of the plasma membrane as expected from the properties of the pDisplay construct (FIG. 3). The nanosensors should thus measure extracellular glutamate levels close to the cell's surface.

Figure 4:
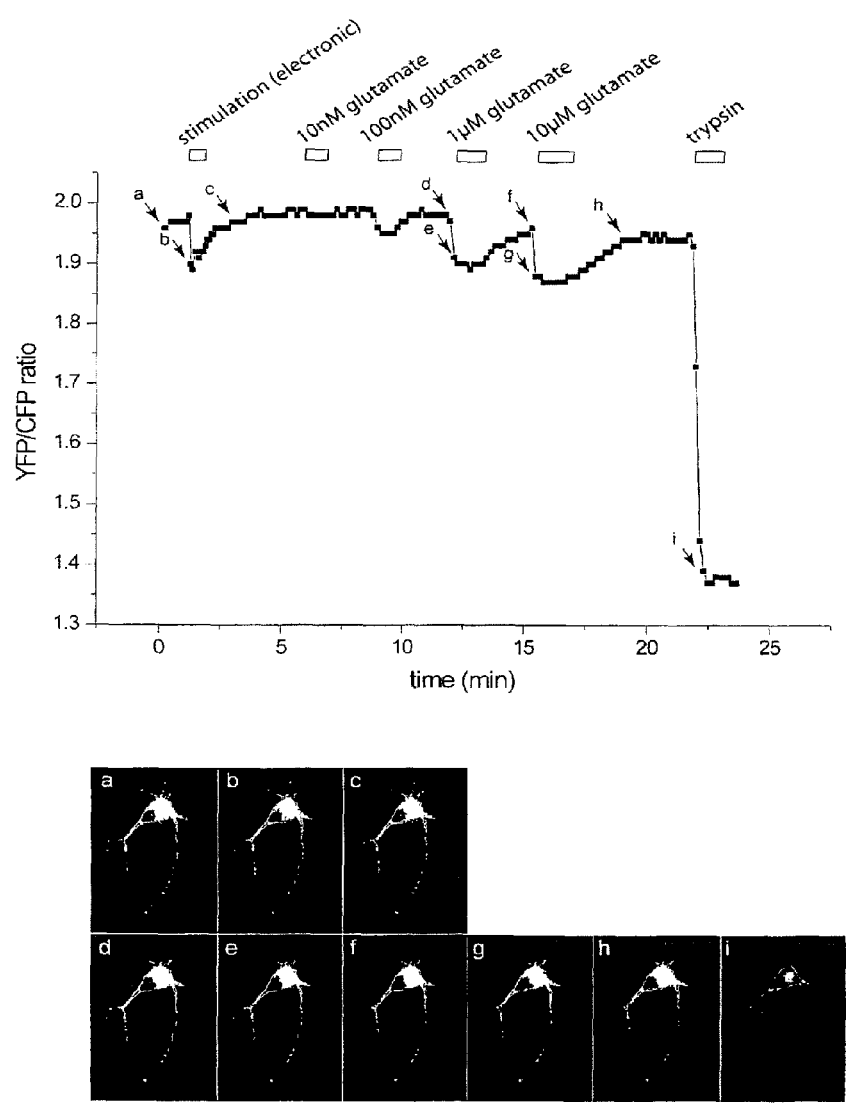
FIG. 4. Emission intensity ratio change in a hippocampal cell expressing FLIP-E 600n sensor. The images are pseudo-colored to indicate the emission intensity ratio change. Open bars above the graph (A) indicate the time point of treatment (stimulation/perfusion with glutamate). Ratio images at the time points indicated by arrows are shown in panel (B), a to i. The change in emission intensity ratio was both observed upon electrical stimulation and upon perfusion with glutamate. The ratio change was not observed when perfusing with low levels of substrate (10 nM glutamate).

To quantify the intensity of CFP and Venus emission, the fluorescence intensity in the two channels in the periphery of the cell was integrated on a pixel-by-pixel basis, and the CFP/Venus ratio was calculated. When the hippocampal cells displaying FLIPE-600n (SEQ ID NO: 13) on the surface were electrically stimulated by passing current pulse, a decrease in CFP/Venus emission ratio was observed (FIG. 4 *a-c*), suggesting that the glutamate is released from hippocampal cells by membrane depolarization. To confirm that the ratio change is due to changes in the extracellular concentration of glutamate, the cell was perfused with increasing concentrations of glutamate. The emission intensity ratio changed in a concentration dependent manner, (FIG. 4 *d-h*), indicating that the FLIPE-600n (SEQ ID NO: 13) displayed on the cell surface recognizes the extracellular glutamate. The working range of the FLIP-E 600n (SEQ ID NO: 13) sensor was between 100 nM to 1 μM, which is consistent with the in vitro working range of FLIPE-600n nanosensor (SEQ ID NO:13). The CFP/Venus ratio increased when the external medium was washed away by perfusion, suggesting that the change in FRET intensity in vivo is reversible.

Figure 5:
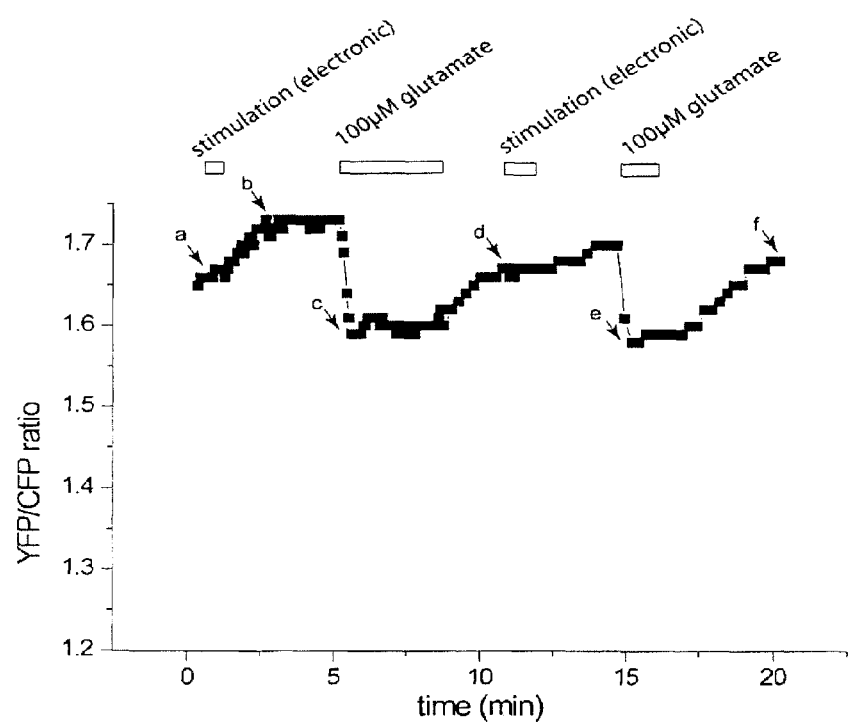
FIG. 5. Emission intensity ratio change in a hippocampal cell expressing FLIP-E 10µ sensor (fluorescent glutamate nanosensor with a $K_d$ for glutamate of 10 µM). Open bars above the graph (A) indicate the time point of treatment (stimulation/perfusion with glutamate). Ratio images at the time points indicated by arrow are shown in panel (B), a to g. Electrical stimulation did not cause a large change in the emission intensity ratio, whereas perfusion with 100 µM glutamate induces a reversible ratio change (panel (B), c and e).
Figure 5:
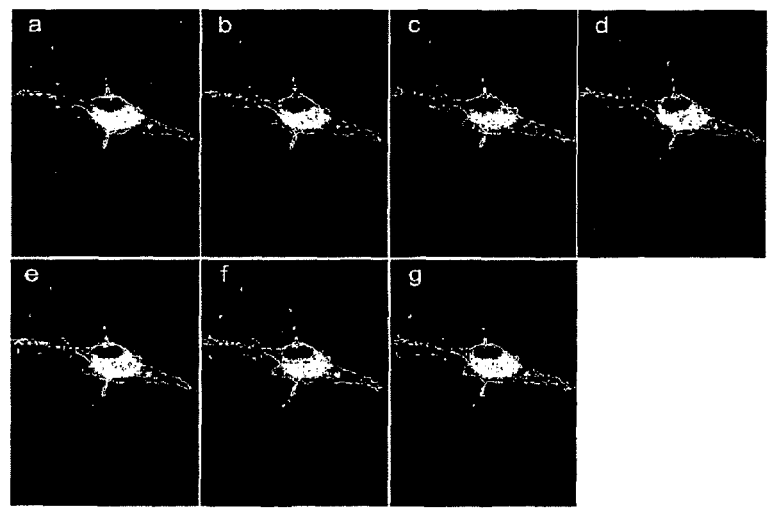

In contrast to the cells expressing FLIPE/600n sensor, the CFP/Venus emission intensity change was not observed in cells expressing FLIPE-10μ (SEQ ID NO: 14) upon electrostimulation (FIG. 5). However, a ratio change was observed when the cells were perfused with higher concentrations of glutamate, (FIG. 5 *c* and *e*), suggesting that the glutamate concentration change induced by depolarization of the cell was below the working range of FLIP-E 10μ sensor.

The novel nanosensors are thus able to measure glutamate on the surface of neuronal cells and to follow the glutamate secretion of presynaptic neurons directly.

Example 4

Internally Fused YbeJ Sensor

Figure 6:
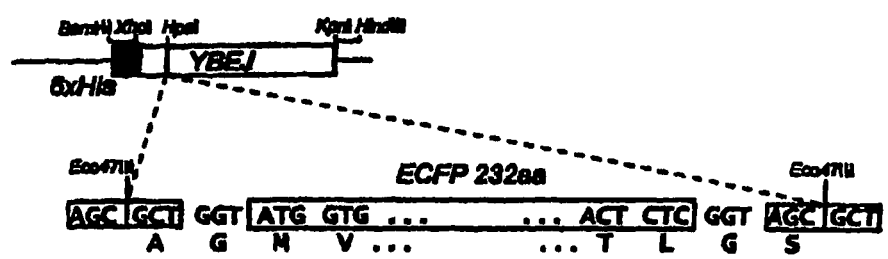
FIG. 6. Internally fused pRSETB FLIP-E nanosensor constructs (A and B) showing insertion site for eCFP.
Figure 6:
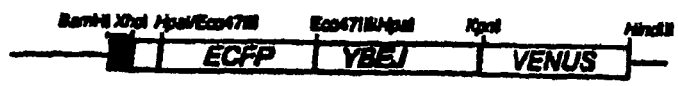
Figure 7B:
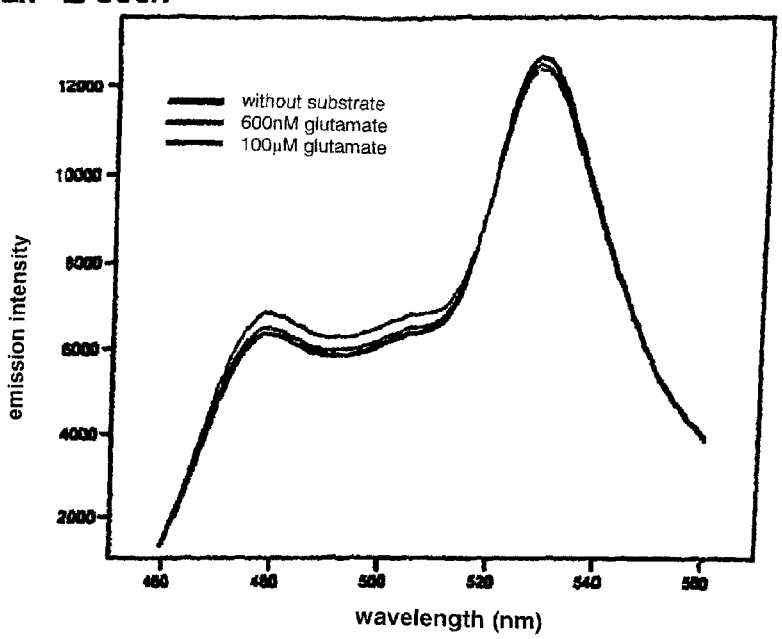
FIG. 7. Graphs comparing emission intensity of FLIP-E 600n with and without glutamate (A) and FLIP-E-internally-fused with and without glutamate (B).
Figure 7B:
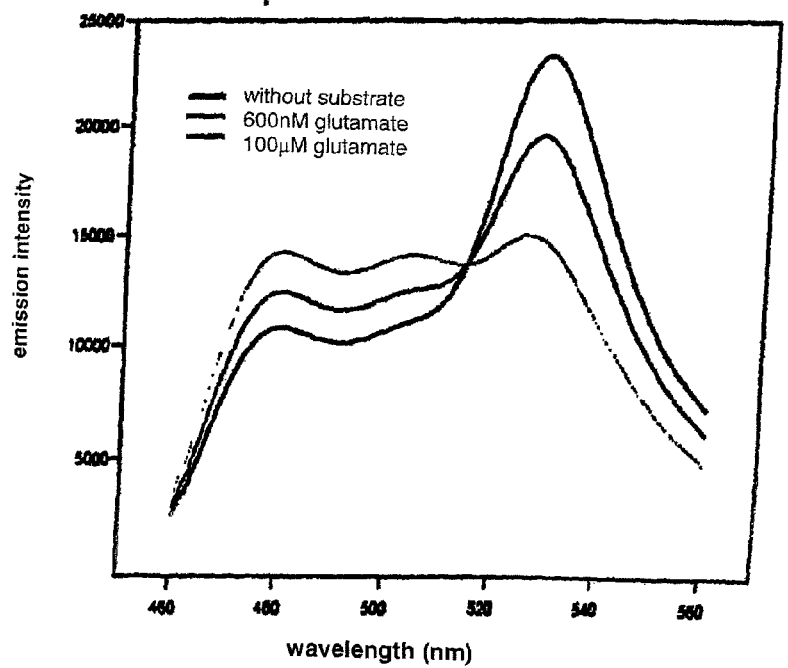

There is currently no crystal structure for YbeJ. We homology-modeled a potential structure on the basis of existing structures of related amino acid biding proteins (His and Gln). We then predicted positions which might be permissive, i.e., sites where an insertion would not affect the overall structure of the protein. We then introduced restriction sites by site directed mutagenesis in these positions (see Table 3 below). Then the coding region for eCFP was inserted into these sites. We then looked for bacterial colonies that showed fluorescence. Only N58V-Q59N with eCFP inserted was fluorescent (based on the YbeJ sequence provided in SEQ ID No. 28). We then attached Venus at the C-terminus (FLIP-E intermol) (see FIG. 6). The affinity was tested and we saw a much larger delta ratio change and an affinity of approximately 1 μM, which is only slightly higher than the 600n version of YbeJ carrying the fluorophores at the ends (see FIG. 7).

Figure 8:
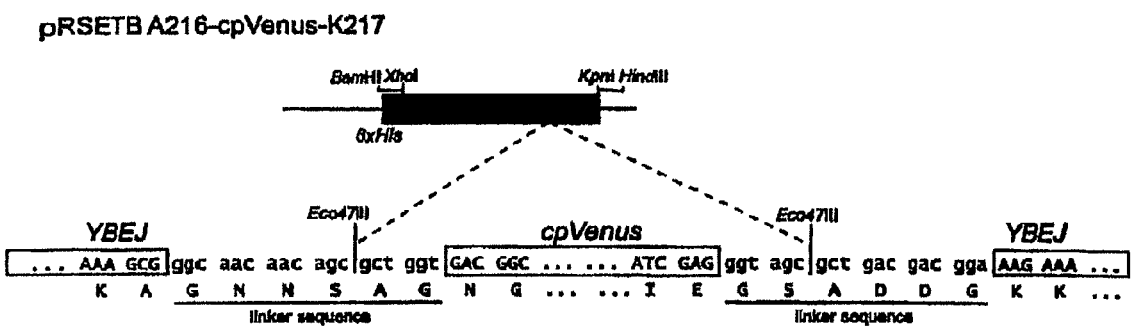
FIG. 8. Internally fused pRSETB FLIP-E 600n A216-cpV-enus-K217 construct (A and B) showing insertion site for cpVenus.
Figure 8:
Figure 9:
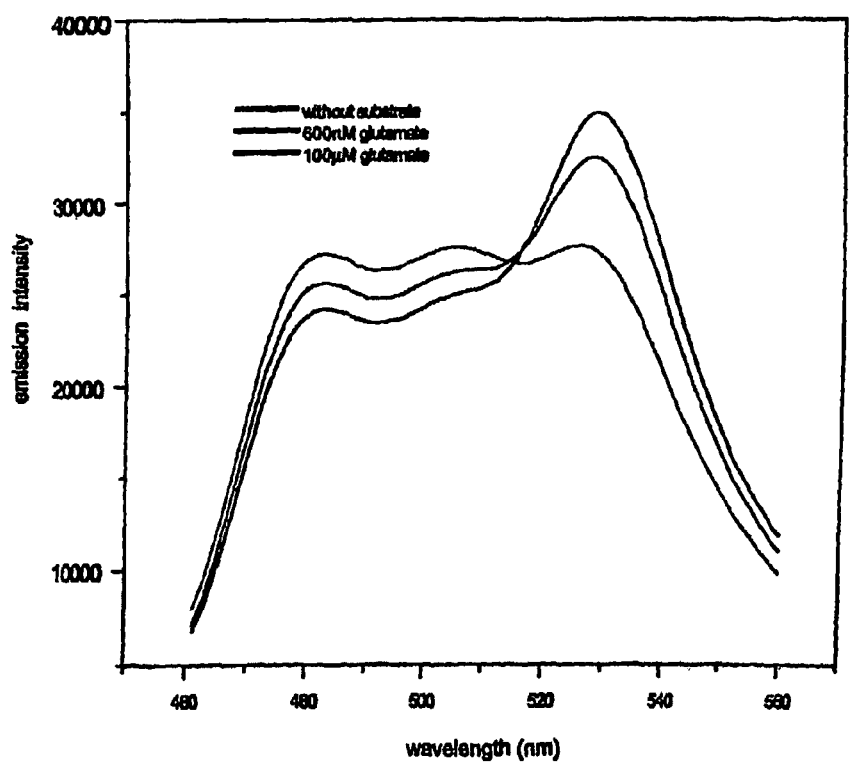
FIG. 9. Emission intensity of internally fused FLIP-E 600n A216-cpVenus-K217 with and without glutamate.

Attempts to insert the eCFP molecule in the Ybej protein were, except for the case of N58V-Q59N, unsuccessful. We speculated that the N-terminus and C-terminus of the eCFP molecules were too far apart, resulting in destabilizing the chimera molecule by making too wide a gap in the Ybej peptide sequence. Circular permutated GFP variants, on the other hand, had N- and C-termini that were next to each other in the original protein. Therefore, we speculated that inserting permutated fluorescent protein instead of eCFP might be less harmful for protein stability. Therefore, we inserted circular permutated Venus (Nagai T. Yamada S., Tominaga T., Ichikawa M., Miyawaki A. (2004) Expanded dynamic range of fluorescent indicators for Ca(2+) by circularly permuted yellow fluorescent proteins. Proc Natl Acad Sci USA. 101: 10554-9) between A216 and K217 with linker sequences GNNSAG (SEQ ID NO: 30) and GSADDG (SEQ ID NO: 31). Then eCFP was fused at the N-terminus (see FIG. 8). The affinity was tested and we saw a much larger delta ratio change and an affinity of approximately 600 nM, which is unchanged from the 600n version of YbeJ carrying the fluorophores at the ends (see FIG. 9).

Without being bound to any particular theory, we believe that the data supports the prediction that rotational movements play a role in FRET. The dipoles have to be oriented in a certain position to each other for efficient resonance energy transfer. However, with terminally fused donor and acceptor moieties, commonly one assumes that the peptide bonds in the linker between the three moieties are freely rotating, thus randomizing this parameter. By inserting the fluorescent moiety into an internal position of the PBP, we prevent free or limited free rotation of the fluorophore around the peptide axis in the linker sequences. Thus, the fluorescent moiety is now rigidly inserted at both ends, thereby reducing free wiggling and possibly explaining the higher observed delta ratio.

TABLE 3

| YbeJ Positions Mutated | Original Sequence | Altered Sequence (restriction site) | eCFP Fluorescence |
|---|---|---|---|
| N58V-Q59N | aatcag | gttaac (HpaI) | + |
| G142-G143A | ggcggc | ggcgcc (NarI) | − |
| G143-D144A | ggcgat | ggcgcc (NarI) | − |
| D144-I145 | gatatc | gatatc (native EcoRV site) | − |
| A149V-N150 | gccgac | gttaac (HpaI) | − |
| N150D-L151 | gacctg | gagctc (Ecl136II) | − |
| M177-N178H | atgaat | atgcat (BfrBI) | − |

Example 5

Internally Fused GGBP Sensors

To demonstrate that internally fused FRET biosensors could be constructed using other proteins, we constructed nanosensors comprising the *Escherichia coli* glucose/galactose binding protein (GGBP) as a binding domain and the Aequorea Victoria green fluorescent protein variants CFP and YFP as reporter domains. Whereas YFP was either fused to the C- or N-terminus of the binding protein, CFP was inserted into various positions of the binding protein yielding a set of internally fused sensors. Each of these sensors is characterized by different relative spatial orientations of the chromophores.

Step 1: Selection of Insertion Sites in GGBP

To scan for permissive sites inside GGBP that tolerate chromophore insertions a total of 13 different sites were selected. Those sites were preferentially located on loops or at the ends of secondary structure elements that are protruding from the core protein and which show a high B-factor in the crystal structure. Sites on both lobes of GGBP were selected. To enable CFP insertions the Nru I restriction recognition sequence was introduced by site directed mutagenesis into the respective positions in the GGBP coding sequence using Kunkel's method. Table 4 depicts the selected sites in GGBP and the mutations introduced by the Nru I recognition sequence.

TABLE 4

Insertion sites and mutations in GGBP.

| mutation | secondary structure |
|---|---|
| insertion sites in N-terminal domain of GGBP | |
| Y12S D13R | Loop |
| P32S D33R | loop at end of helix |
| S46S K47R | Helix |
| K58S G59R | loop at end of helix |
| Q83S N84R | Loop |
| Y102S D103R | Loop |
| G275S K276R | Loop |
| T282S N283R | Loop |
| insertion sites in C-terminal domain of GGBP | |
| N130S Q131R | loop at end of helix |
| N136S K137R | Loop |
| P150S G151R | Loop |
| G198S P199R | Loop |
| N226S K227R | loop at end of helix |

Numbering starts with first amino acid of the mature protein lacking the 23 amino acid signal sequence.

Step 2: Insertion of CFP and Screening for Fluorescent Colonies

The CFP coding sequence was inserted into the Nru I site in GGBP by molecular cloning. The constructs were designed to permit expression of the unfinished sensors at all stages of development. Two sets of constructs were engineered that bear the same insertion sites. One set was designed to enable the N-terminal fusion with YFP, the other to enable the C-terminal fusion with YFP.

The ligation reactions were transferred into the *E. Coli* expression strain BL21(DE3)gold. After transformation, the bacteria were spread on plates using selective conditions for the presence of the vector. Cells were allowed to form colonies over night at 37 degree Celsius. Subsequently, the plates were transferred to 4 degree Celsius for about 10 days to facilitate chromophore maturation. Fluorescent colonies were selected for further cloning using a UV lamp or the fluorescence module of a dissecting microscope. The screening approach permits the effective and time-saving construction of a larger number of insertions in parallel. Furthermore, it offers the opportunity to identify insertions that do not fold correctly leading to very dim fluorescence of the colonies. Table 5 reflects the relative fluorescence intensity of the colonies.

TABLE 5

Relative fluorescence of bacterial colonies.
Fluorescence of colonies after insertion of CFP

| | fluorescence on plate |
|---|---|
| Set for C-terminal YFP fusion | |
| pRSETB-BamHI-mglBF16A/Y12S-CFP-D13R-kpnl 3a/1 | low |
| pRSETB-BamHI-mglBF16A/P32S-CFP-D33R-kpnl 6a/3 | low |
| pRSETB-BamHI-mglBF16A/S46S-CFP-K47R-kpnl 11a/5 | microscope visible only |
| pRSETB-BamHI-mglBF16A/K58S-CFP-G59R-kpnl 1d/7 | microscope visible only |
| pRSETB-BamHI-mglBF16A/Q83S-CFP-N84R-kpnl 6d/57 | microscope visible only |
| pRSETB-BamHI-mglBF16A/Y102S-CFP-D103R-kpnl 17a/13 | microscope visible only |
| pRSETB-BamHI-mglBF16A/G275S-CFP-K276R-kpnl 14c/15 | microscope visible only |
| pRSETB-BamHI-mglBF16A/T282S-CFP-N283R-kpnl 13/73 | microscope visible only |
| pRSETB-BamHI-mglBF16A/N130S-CFP-Q131R-kpnl 17/65 | microscope visible only |
| pRSETB-BamHI-mglBF16A/N136S-CFP-K137R-kpnl 23/69 | microscope visible only |
| pRSETB-BamHI-mglBF16A/P150S-CFP-G151R-kpnl 25/23 | microscope visible only |
| pRSETB-BamHI-mglBF16A/G198S-CFP-P199R-kpnl 30/26 | microscope visible only |
| pRSETB-BamHI-mglBF16A/N226S-CFP-K227R-kpnl 33/27 | microscope visible only |
| Set for N-terminal YFP fusion | |
| pRSETB-kpnl-mglBF16A/Y12S-CFP-D13R-HindIII 3/29 | normal |
| pRSETB-kpnl-mglBF16A/P32S-CFP-D33R-HindIII 3b/32 | low |
| pRSETB-kpnl-mglBF16A/S46S-CFP-K47R-HindIII 6/34 | normal |
| pRSETB-kpnl-mglBF16A/K58S-CFP-G59R-HindIII 5b/35 | low |
| pRSETB-kpnl-mglBF16AQ83S-CFP-N84R-HindIII 11/37 | normal |
| pRSETB-kpnl-mglBF16A/Y102S-CFP-D103R-HindIII 14/41 | low |
| pRSETB-kpnl-mglBF16A/G275S-CFP-K276R-HindIII 18/43 | high |

TABLE 5-continued

Relative fluorescence of bacterial colonies.
Fluorescence of colonies after insertion of CFP

|  | fluorescence on plate |
|---|---|
| pRSETB-kpnl-mglBF16A/T282S-CFP-N283R-HindIII 22/46 | normal |
| pRSETB-kpnl-mglBF16A/N130S-CFP-Q131R-HindIII 25/47 | norm |
| pRSETB-kpnl-mglBF16A/N136S-CFP-K137R-HindIII 29/49 | low |
| pRSETB-kpnl-mglBF16A/P150S-CFP-G151R-HindIII 17b/51 | microscope visible only |
| pRSETB-kpnl-mglBF16A/G198S-CFP-P199R-HindIII 33/54 | microscope visible only |
| pRSETB-kpnl-mglBF16A/N226S-CFP-K227R/-HindIII 37/55 | low |

Fluorescence intensities range from microscope visible only < low < normal < high Step 3: Fusion to YFP and Screening for Colonies Expressing Both Chromophores The coding sequence of YFP was inserted into the expression cassettes containing the CFP insertions of step 2 by molecular cloning. Using the two sets of CFP insertions two sets of fluorescent nanosensors were obtained that bear the same insertion of CFP but have YFP attached either to their N- or C-terminus. The ligation reactions were transferred into the expression strain BL21(DE3)gold. Following growth under selective conditions the resulting colonies were used to start 200 µl cultures in a microtiter plate to screen for clones expressing both chromophores. The cultures were grown for two days at room temperature and allowed to rest for two days at 4 degrees Celsius to facilitate chromophore maturation. Subsequently the cultures were excited at the CFP excitation wavelength (433 nm) and emission intensities were recorded from 460 nm to 560 nm covering the emission peaks of CFP and YFP. Two to three clones of each nanosensor expression cassette that showed the presence of both chromophores were selected for further analysis. Small scale cultures were started to harvest the protein by Ni-NTA affinity chromatography. To analyze the ratio changes of the new nanosensors, spectra of the purified proteins were recorded in the absence and presence of 10 mM glucose and the difference in YFP/CFP emission intensity ratios were calculated. Table 6 depicts the measured ratio changes.

TABLE 6

| C-terminal YFP nanosensor | Δratio (10 mM-0 mM) | |
|---|---|---|
| FLIP-mglBF16A/Y12S-CFP-D13R-YFP (SEQ ID NOs: 15 and 16) | 1.34 | 1.11 |
| FLIP-mglBF16A/P32S-CFP-D33R-YFP | 0.18 | 0.12 |
| FLIP-mglBF16A/S46S-CFP-K47R-YFP | 0.01 | −0.07 |
| FLIP-mglBF16A/K58S-CFP-G59R-YFP | 0.00 | −0.04 |
| FLIP-mglBF16A/Q83S-CFP-N84R-YFP | −0.01 | −0.02 |
| FLIP-mglBF16A/Y102S-CFP-D103R-YFP | 0.02 | −0.01 |
| FLIP-mglBF16A/G275S-CFP-K276R-YFP (SEQ ID NOs: 17 and 18) | −0.19 | −0.25 |
| missing | | |
| FLIP-mglBF16A/N130S-CFP-Q131R-YFP | −0.07 | −0.11 | 0.02 |
| FLIP-mglBF16A/N136S-CFP-Q137R-YFP | −0.02 | −0.09 |
| missing | | |
| FLIP-mglBF16A/G198S-CFP-P199R-YFP | −0.01 | −0.01 |
| FLIP-mglBF16A/N226S-CFP-K227R-YFP | −0.01 | −0.01 |

TABLE 6-continued

| N-terminal YFP nanosensor | ΔRatio (10 mM-0 mM) | | |
|---|---|---|---|
| FLIP-YFP-mglBF16A/Y12S-CFP-D13R (SEQ ID NOs: 19 and 20) | −0.42 | −0.42 | |
| FLIP-YFP-mglBF16A/P32S-CFP-D33R (SEQ ID NOs: 21 and 22) | 0.35 | 0.36 | 0.37 |
| FLIP-YFP-mglBF16A/S46S-CFP-K47R | 0.01 | 0.01 | |
| FLIP-YFP-mglBF16A/K58S-CFP-G59R | 0.07 | 0.11 | |
| FLIP-YFP-mglBF16A/Q83S-CFP-N84R | 0.07 | 0.14 | |
| missing | | | |
| FLIP-YFP-mglBF16A/G275S-CFP-K276R (SEQ ID NOs: 23 and 24) | 0.28 | 0.33 | 0.30 |
| FLIP-YFP-mglBF16A/T282S-CFP-N283R (SEQ ID NOs: 25 and 26) | 0.39 | 0.32 | 0.35 |
| missing | | | |
| FLIP-YFP-mglBF16A/N136S-CFP-K137R | 0.03 | 0.02 | |
| FLIP-YFP-mglBF16A/N150S-CFP-G151R | 0.00 | 0.00 | 0.01 |
| FLIP-YFP-mglBF16A/G198S-CFP-P199R | 0.00 | 0.01 | |
| FLIP-YFP-mglBF16A/N226S-CFP-K227R | 0.00 | | |

Ratio changes of completed nanosensors between 0 mM and 10 mM glucose. For each nanosensor two or three clones were analysed. For missing nanosensors no clones expressing both chromophores were identified. Grey background indicates that the two chromophores are on different lobes, white background that the chromophores are on the same lobe of GGBP. Bold nanosensors were selected for further analysis.

Step 4: Analysis of Selected Nanosensors

Nanosensors with a ratio change greater 0.2 (depicted in bold letters in table 6) were selected for further analysis. Protein was purified from larger scale cultures using Ni-NTA affinity chromatography. The resulting protein extracts were titrated with increasing concentrations of glucose in a microplate based FRET assay. The affinity of the nanosensors was determined by non-linear regression of the titration curves. Furthermore, spectra were recorded in the absence, at half-saturation and saturating glucose concentrations. As a control the original nanosensor, FLIPmglBF16A, where GGBP is sandwiched between CFP and YFP, is included. To normalize the ratio change (delta ratio), the ratio change was divided by the ratio in the absence of glucose (Table 7) (see FIGS. 8 and 9).

TABLE 7

Properties of nanosensors.

| sensor | ratio | | | | |
|---|---|---|---|---|---|
|  | absence | saturation | Δ | Δ/absence | Kd (mM) |
| FLIP-mglBF16A/Y12S-CFP-D13R-YFP (SEQ ID NOs: 15 and 16) | 4.55 | 7.21 | 2.66 | 0.58 | 0.6 |

TABLE 7-continued

Properties of nanosensors.

| sensor | ratio | | | Δ/absence | Kd (mM) |
| --- | --- | --- | --- | --- | --- |
| | absence | saturation | Δ | | |
| FLIP-YFP-mglBF16A/G275S-CFP-K276R (SEQ ID NOs: 23 and 24) | 1.63 | 2.32 | 0.69 | 0.42 | 4.6 |
| FLIP-YFP-mglBF16A/T282S-CFP-N283R (SEQ ID NOs: 25 and 26) | 2.11 | 2.55 | 0.44 | 0.21 | 4 |
| FLIP-YFP-mglBF16A/P32S-CFP-D33R (SEQ ID NOs: 21 and 22) | 3.4 | 3.84 | 0.44 | 0.13 | 2.2 |
| FLIP-YFP-mglBF16A/Y12S-CFP-D13R (SEQ ID NOs: 19 and 20) | 2.6 | 2.33 | −0.27 | −0.10 | 1.8 |
| FLIPmglBF16A | 2.95 | 2.6 | −0.35 | −0.12 | 0.6 |
| FLIP-mglBF16A/G275S-CFP-K276R-YFP (SEQ ID NO: 17 and 18) | 1.93 | 1.6 | −0.33 | −0.17 | 13.8 |

Absence depicts the ratio at the absence of glucose, saturation at saturating concentrations of glucose.
Δ shows the delta ratio between saturation and absence of glucose.
Δ/absence is the normalized delta ratio.

Summary and Discussion:

Among 22 insertions, six functional glucose sensors were identified. Four sensors showed positive ratio changes upon addition of glucose. Only two displayed negative ratio changes as the original sensor FLIPmglBF16A. Four sensors had greater relative ratio changes as compared to FLIPmglBF16A. Two sensors showed relative ratio changes similar to FLIPmglBF16A. Hence, the insertion of a chromophore into the binding protein proved to be an efficient strategy to design and improve the nanosensors. Moreover, the chromophores do not have to be located on different lobes of the binding protein to yield functional sensors.

The direction and extent of a sensor's ratio change depend on the relative spatial orientation of the chromophores before and after binding of glucose. The change in spatial orientation can be a change in distance, a change in angular orientation or both. The contribution of the change in angular orientation increases, when the chromophores are fixed and cannot freely randomize prior to the transfer of energy.

Inserting CFP into the binding protein stiffens the connection between these two components of the sensor as compared to simple C- or N-terminal fusions of CFP. This has a major impact on the sensor. The stiffer connection improves the allosteric coupling between the hinge-twist motion of the binding protein and the change in spatial orientation of the chromophores. Particularly, the change in angular orientation of the chromophores is intensified, since the wobbling of CFP is reduced. Because under this condition the direction of the ratio change cannot be predicted from the change in chromophore distance alone, it follows that sensors with ratio changes in both directions were engineered by inserting CFP.

However, due to the nature of FRET, not every relative change in chromophore orientation can translate into a change in ratio. Certain combinations of relative spatial chromophore orientations exist that are completely different but lead to a similar degree of FRET. Thus despite a large spatial reorientation of the chromophores, no significant ratio change might be observed. Moreover, insertion of CFP might abolish glucose binding by GGBP and some insertions might not even fold correctly.

Figure 10:
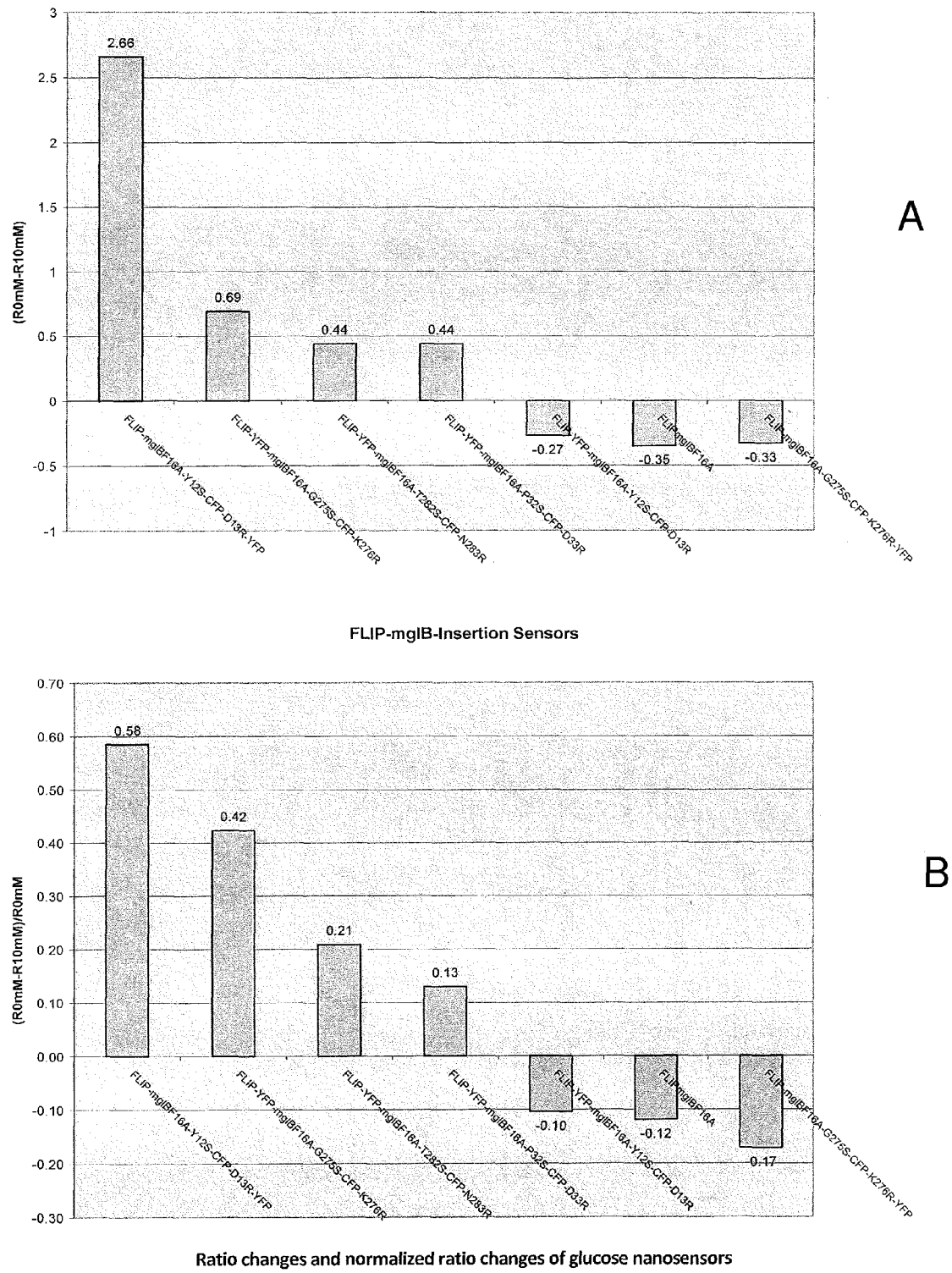
FIG. 10. Graphs showing the ratio changes (A) and normalized ratio changes (B) of internally fused glucose nanosensors.
Figure 11A:
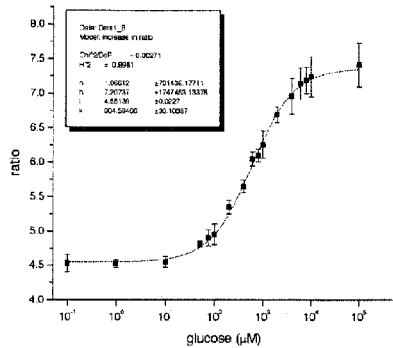
FIG. 11. Graphs showing titration curves (A, C, E, G, I, K, M) and spectra (B, D, F, H, J, L, N) of glucose nanosensors.
Figure 11A:
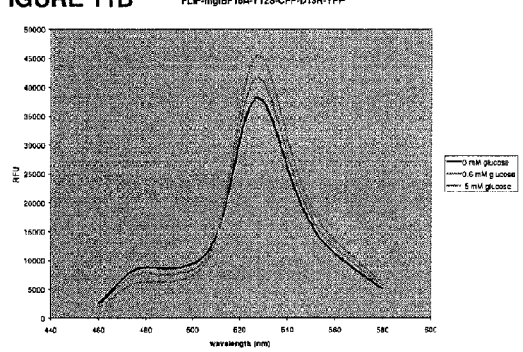
Figure 11C:
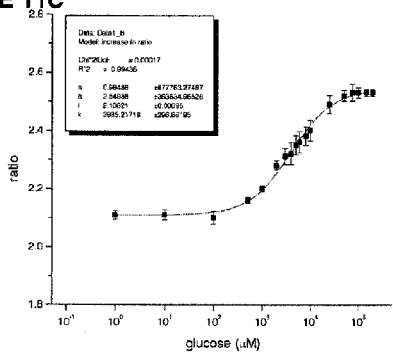
Figure 11C:
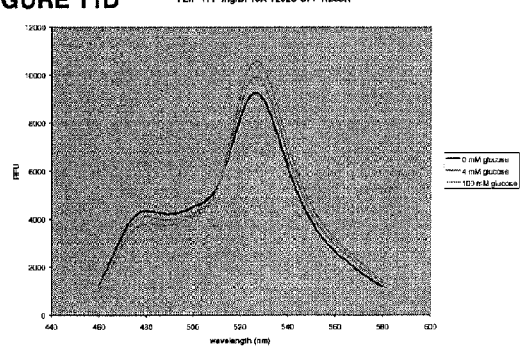
Figure 11E:
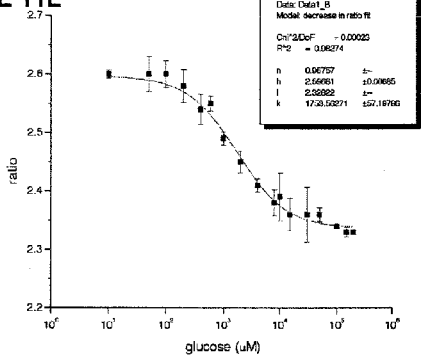
Figure 11E:
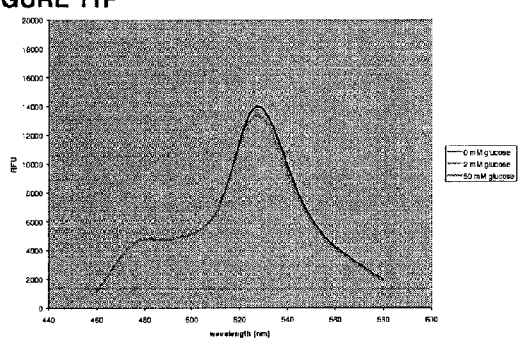
Figure 11G:
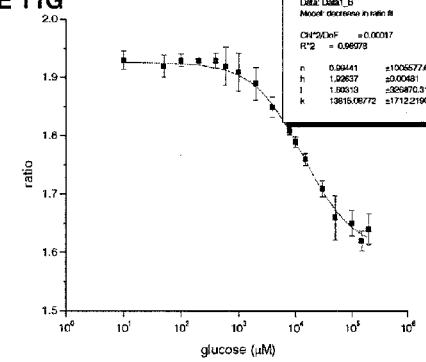
Figure 11G:
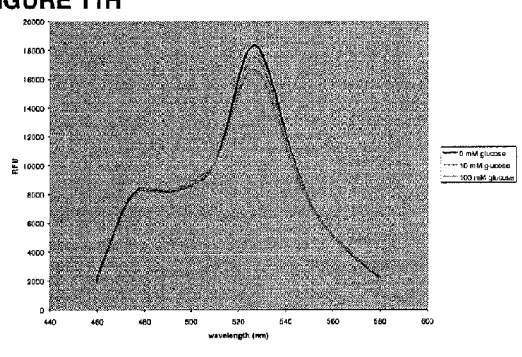
Figure 11I:
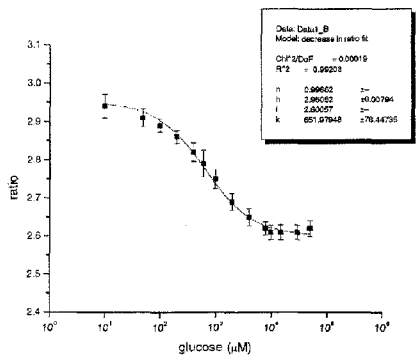
Figure 11J:
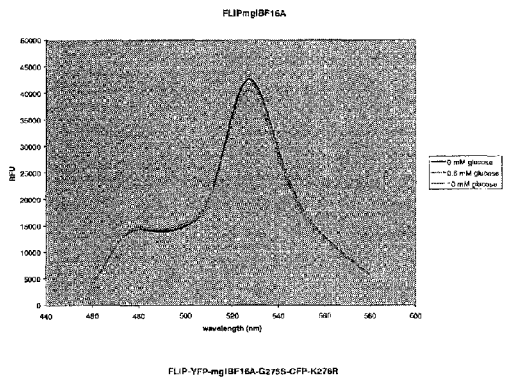
Figure 11K:
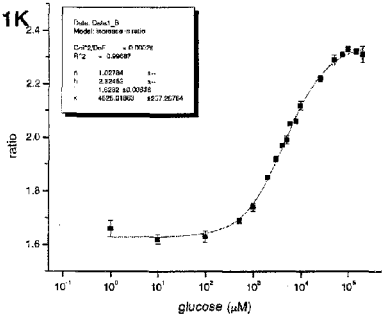
Figure 11L:
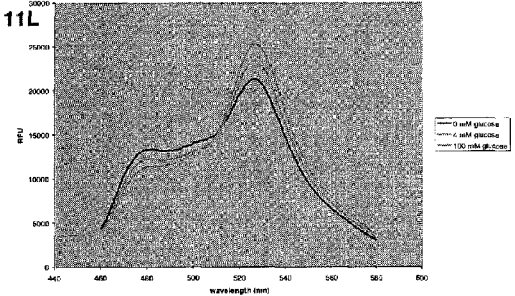
Figure 11M:
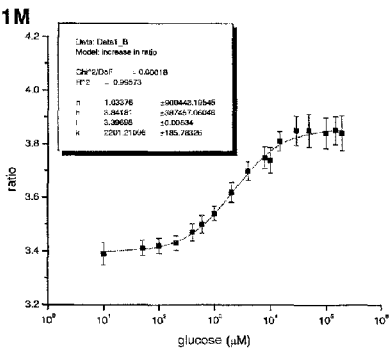
Figure 11N:
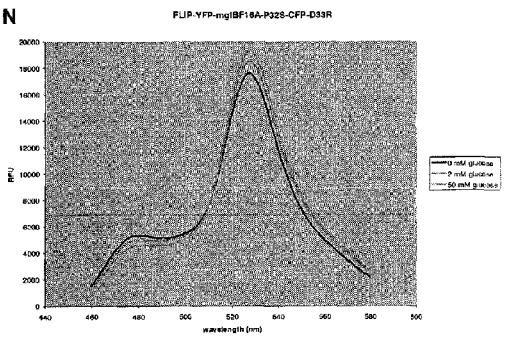

The chart in FIG. 10 shows the correlation between the starting ratio in the absence of glucose and the normalized ratio change and assesses the overall success rate of the insertions. Sector 1 depicts the insertions that do not fold properly. For two insertions, both the N-terminal and C-terminal YFP fusion display a low ratio and a negligible ratio change. Sector 2 harbors 8 insertions which fold correctly but do no show a significant ratio change. This can be attributed to similar degrees of FRET before and after binding of glucose or to the fact that glucose binding is abolished. The fact that at least some functional sensors show a decreased affinity towards glucose supports the assumption that by reverting mutation F16A a number of these insertions can be turned into functional sensors. Sector 3 depicts 5 sensors based on 4 different insertions that possess higher ratio changes than the original sensor FLIPmglBF16A, which is shown as a reference point.

Thus, despite the above limitations, scanning different insertion sites for CFP in GGBP appears be an efficient method to improve the sensors. Further, the fact that the chromophores can be located on the same lobe to yield a functional sensor potentially enables us to use chromophore insertions to turn virtually each binding protein or enzyme into a sensor. It may be imagined given the above data that a further increase in signal response may be obtained by internally fusing both chromophores into the ligand-binding moiety sequence. We are creating these constructs, and expect them to show further improved properties.

Example 6

Design of FRET Biosensors with Improved Sensitivity

Having learned that the reduced rotational averaging in the internal insertion of a fluorophores is a general strategy to generate sensors with high ratio changes, we hypothesized that one may obtain similar results by reducing the rotational freedom of the linkage between the analyte binding domain and the fluorophores. We thus systematically removed sequences that connect the core protein structure of the binding domain and the fluorophore, i.e. by removing linker sequences and by deleting both amino acids from the ends of the analyte binding moiety and the fluorophores. We found that close coupling also leads to higher ratio changes. This concept is exemplified for FLIPglu.

Figure 12:
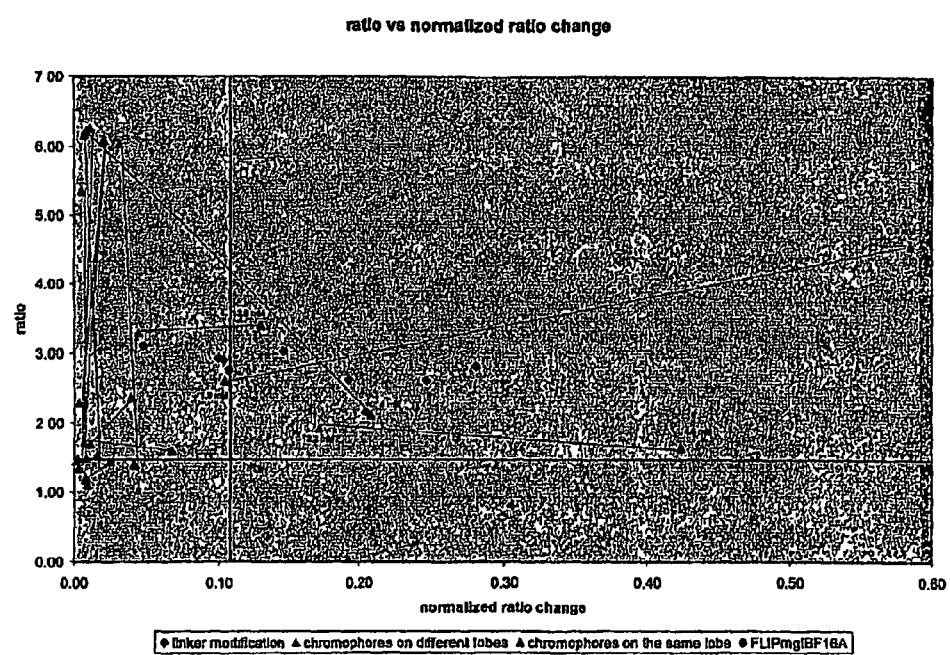
FIG. 12. Figure showing the correlation between the starting ratio in the absence of glucose and the normalized ratio change.
Figure 13:
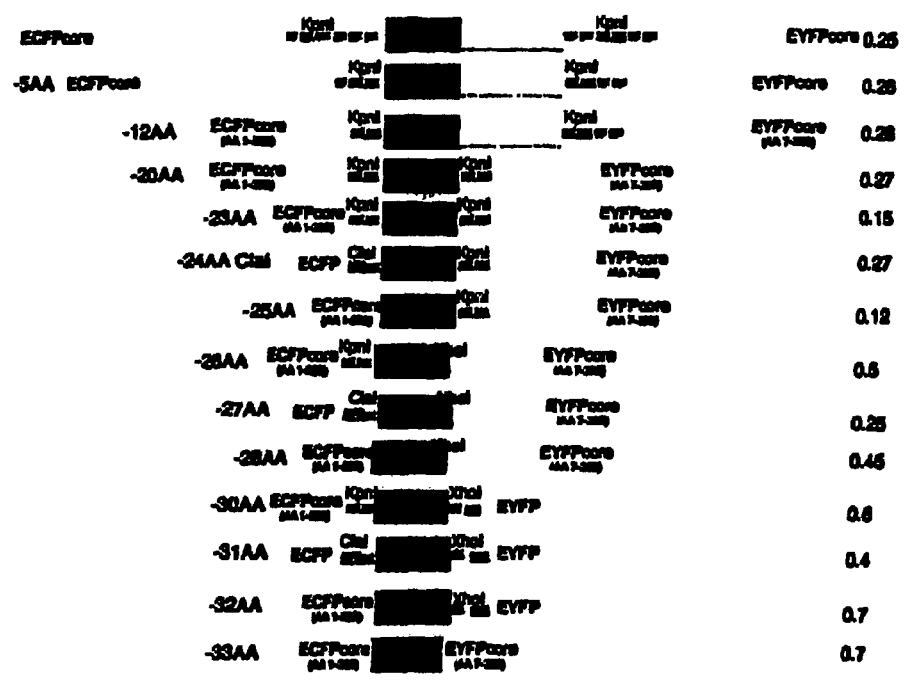

To perform the comparison, thirteen different shortened sensor proteins were generated. Deletions of up to 8 amino acids of the linker regions between the fluorophores and the analyte binding domain did not result in a marked increase of the ratio change (see FIG. 13). Further deletions were done on the C-terminus of the ECFP (6 or 9 amino acids), on the C-terminus of the mglB analyte binding domain (5 amino acids) and on the N-terminus of the EYFP (1, 2 or 6 amino acids), which resulted in an overall increase of the change in ratio in 5 of the proteins (see FIG. 12). In all cases, the core of the fluorophore determined necessary for fluorescence (amino acid 7 to 229, Li et al., 1997, JBC 272 pp. 28545) was included.

Example 7

Testing of FRET Biosensors with Improved Sensitivity In Vitro

Materials and Methods:
Linker deletions for FLIPglu Internally Fused Sensors

Figure 14:
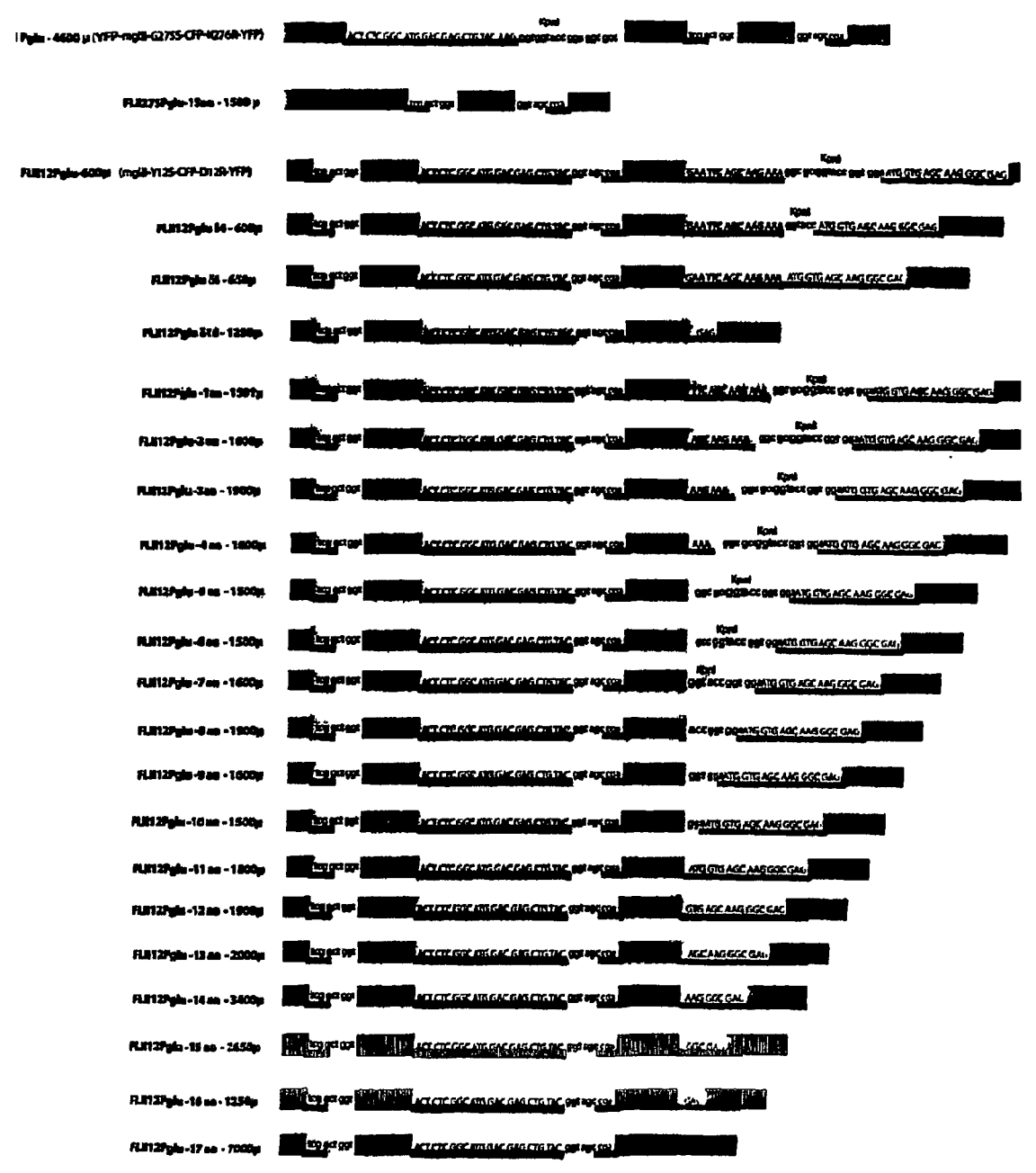

Two internally fused glucose sensors were chosen on the basis of their Δ ratio and affinities, FLII$^{12}$Pglu-600μ and FLIIP$^{275}$Pglu-4.6m. For FLII$^{12}$Pglu-600μ, the linker and less well-structured domains at the termini of mglB and Citrine (together comprising the 17 amino acid "composite linker") was systematically deleted starting at the mglB using Kunkel mutagenesis (Kunkel et al.). 17 primers were used designed to delete increasing number of amino acid residues from FLII$^{12}$Pglu-600μ creating FLII$^{12}$Pglu-1aa through FLII$^{12}$Pglu-17aa. In addition, deletion of 16 amino acids, FLII$^{12}$PgluΔ16 was also created by adding a XhoI site at residue 305 of mglB and cloning a shortened Citrine (amino acids 7-238) using XhoI and HindIII. FLII$^{12}$Pglu-16aa and FLII$^{12}$PgluΔ16 thus differ in a single amino acid residue at position 305 of mglB (Ala for FLII$^{12}$Pglu-16aa and Leu for FLII$^{12}$Pglu δ16). Two more primers were used to delete 4 and 6 amino acid residues Gly-Gly-Thr-Gly-Gly-Ala (SEQ ID NO: 32) (GGTGGTACCGGAGGCGCC (SEQ ID NO: 33)) of the plasmid derived linker between the mglB and Citrine keeping the mglB and Citrine intact (FLII$^{12}$Pglu δ4 and FLII$^{12}$Pglu δ6). In case of FLIIP$^{275}$Pglu-4.6m, where Citrine is at the N-terminus, a single primer was used to delete 15 amino acid residues (9 from the C-terminus dispensable portion of Citrine and 6 of the plasmid derived linker connecting the Citrine and mglB) (FIG. 14).

In Vitro Analysis of Sensors

Constructs were transferred to *E. coli* BL21(DE3)Gold (Stratagene, USA) using electroporation, extracted and purified as previously described (Fehr et al., 2002, Proc. Natl. Acad. Sci. USA 99: 9846-9851). Emission spectra and ligand titration curves were obtained by using a monochromator microplate reader (Safire, Tecan, Austria). The excitation filter was 433/12 nm; emission filters for ECFP and EYFP (also Citrine and Venus) emission was 485/12 and 528/12 nm, respectively. All analyses for FLIPE constructs and linearly-fused FLIPglu constructs were performed in 210 mM sodium phosphate buffer, pH 7.0; analyses of FLIP$^{X}$Pglu were done in 20 mM MOPS buffer, pH 7.0. In order to compare the FLII$^{12}$Pglu-600μ and FLIIP$^{275}$Pglu-4.6m deletions better, the Citrine emission values for each was kept constant at about 20000 and the emission gain was kept constant at 80. The sensors were also analysed in Hanks buffer (pH 7.2), synthetic mammalian cytosol (pH 7.2), synthetic plant cytosol (pH 7.2) and MOPS pH 5.0 using the same amount of protein as used for assay in MOPS pH 7.0. The $K_d$ of each sensor was determined by fitting to a single site binding isotherm: $S=(r-r_{apo})/(r_{sat}-r_{apo})=[L]/(K_d+[L])$, where S is saturation; [L], ligand concentration; r, ratio; $r_{apo}$ ratio in the absence of ligand; and $r_{sat}$, ratio at saturation with ligand. Measurements were performed with at least three independent protein extracts. ECFP emission is characterized by two peaks at 485 and 502 nm; the ratio was defined here as the uncorrected fluorescence intensity at 528 nm divided by the intensity at 485 nm.

Analysis in Different Buffers

In order to see the effect of environmental conditions on the sensors, they were analysed under various conditions, in mammalian cell culture solution (Hanks buffer: 137 mM NaCl, 5.4 mM KCl, 0.3 mM Na$_2$HPO$_4$, 0.4 mM KH$_2$PO$_4$, 4.2 mM NaHCO$_3$, 0.6 MgSO$_4$, 10 mM Lactate, 1 mM Pyruvate pH 7.4), synthetic mammalian cytosol (135 mM K(gluconate), 4 mM KCl, 12 mM NaHCO$_3$, 0.8 mM MgCl$_2$, 0.2 μM CaCl$_2$ pH 7.4), synthetic plant cytosol (10 mM NaCl, 150 mM K(gluconate), 1 mM MgCl$_2$, 100 mg/mL BSA, 10 mM HEPES pH 7.5 with BTP) and MOPS buffer pH 5.0. The protein amount was kept constant as for the analysis in MOPS buffer pH 7.0. The spectrum was measured with no glucose, 10 mM glucose and 100 mM glucose in triplicate and the analysis was done with 2 independent protein preps for each sensor.

Results:
FLIPglu Linker Variation

To further improve the signal to noise ratio and to develop environmentally stable sensors, a systematic deletion analysis of the linkers in the intramolecular FRET sensor FLII$^{12}$Pglu-600μ (Deuschle et al., 2005, Protein Science 14:2304-2314) was carried out. The glucose nanosensor FLII$^{12}$Pglu-600μ consists of the mature glucose/galactose-binding protein mglB from *Escherichia coli* into which CFP had been inserted at position 12 and a linearly fused EYFP via a 6-amino acid linker to the C-terminus (Deuschle 2005). The linker and less well-structured domains at the termini of mglB and EYFP variants (together comprising the "composite linker") would be assumed to allow flexible (if not free) rotation of the fluorophores relative to the binding protein and one another. The composite linker was systematically truncated in an attempt to decrease rotational averaging and to enhance the allosteric coupling. FPs possess terminal regions not absolutely required for folding and fluorescence (an N-terminal helix and a C-terminal coil) (Li et al., 1997, J. Biol. Chem. 272: 28545-28549). Furthermore, five amino acids may be deleted from the C-terminal region of the mglB binding protein without affecting binding. These together yield 17 amino acids, the removal of which might a priori be expected to preserve binding and fluorescence (FIG. 14). Composite linker regions were deleted from FLII$^{12}$Pglu-600μ in a stepwise manner.

Effect of Deletions on Ratio and Kd

Figure 15:
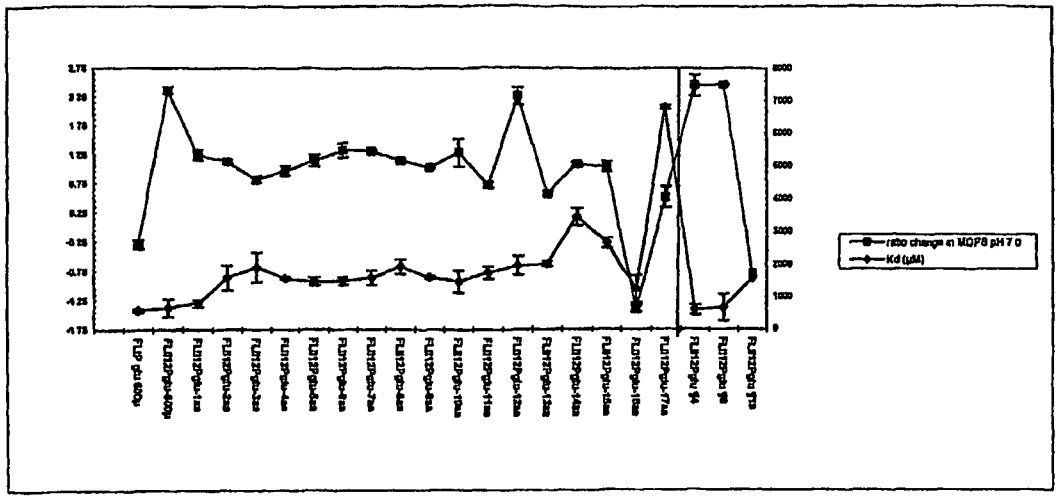
FIG. 15. Correlation between Δ ratio in MOPS buffer pH 7.0 (red), number of amino acid residues deleted and affinity (Kd, µM) of the FLII[12]Pglu-600µ deletion constructs.

Most of the FLII$^{12}$Pglu-600μ deletions showed a decreased FRET compared to the full length sensor. The Δ ratio of the deletion constructs varying between 0.52 (FLII$^{12}$Pglu-17aa, 78% decrease) to 2.26 (FLII$^{12}$Pglu-12aa, 5% decrease). Out of the 20 deletion constructs 14 still had a Δ ratio of above 1 of which 5 constructs had Δ ratio of 1.3 or more (FLII$^{12}$Pglu-6aa 1.32, FLII$^{12}$Pglu-7aa 1.31, FLII$^{12}$Pglu-10aa 1.3, FLII$^{12}$Pglu-12aa 2.26, FLII$^{12}$Pglu-16aa-1.40). FLII$^{12}$Pglu δ4 and FLII$^{12}$Pglu δ6 had a slightly improved Δ ratio (4% increase) as compared to FLII$^{12}$Pglu-600μ. Interestingly, FLII$^{12}$Pglu-16aa and FLII$^{12}$Pglu δ16, showed a decrease in ratio upon ligand binding whereas the FLII$^{12}$Pglu-600μ and all of the other deletions show increased ratio upon ligand binding. The affinity of each of the sensors was determined by titrating with glucose (Table 8). The affinity to glucose decreased after deletion of 2 amino acids FLII$^{12}$Pglu-2aa through FLII$^{12}$Pglu-13aa have binding constants ranging between 1.5-2.0 mM, deletion of more than 13 amino acids further decreased the affinity (FLII$^{12}$Pglu-14aa 3.4 mM, FLII$^{12}$Pglu-15aa 2.6 mM). FLII$^{12}$Pglu-17aa has a dramatically decreased affinity of 6.8 mM. FLII$^{12}$Pglu δ4 and FLII$^{12}$Pglu δ6 however have Kd comparable to FLII$^{12}$Pglu-600μ (FIG. 15, Table 8).

FLIIP$^{275}$Pglu-15aa showed an increased Δ ratio of 1.14 (73% increase) as compared to FLIIP$^{275}$Pglu-4.6m, which has a Δ ratio of 0.66. However the deletion affected affinity dramatically, decreasing it to a point where the sensor was no longer measurable (data not shown). So, in order to make a usable sensor, the alanine-16 in the mglB, was mutated back to wild-type phenylalanine which is involved in glucose binding (Fehr et al. 2003), thus decreasing the affinity of FLIIP$^{275}$Pglu-15aa to 1.5 mM and an increased Δ ratio.

The FLII$^{12}$Pglu-600μ loop-inserted sensor shows a significantly higher ratio change than the linear-fusion FLIPglu-600μ sensor; with little effect on ligand affinity. Upon deletion of up to eleven residues from the sensor (first from the C-terminal helix of the mglB domain: 5 residues, then from the synthetic linker connecting the mglB and YFP domains: 6 residues), there is a slight decrease in ligand affinity, and a decrease in ligand-dependent signal change. Molecular modeling suggests that up to this point, there is still a good degree of separation between the YFP and both the N- and C-terminal lobes of mglB (the CFP is not modeled to be highly sterically regulated by any of the other domains). The N-terminal domain of mglB is modeled to be in closer proximity to the YFP in the open versus the closed conformation (modeled by overlaying the open and closed structures of the E. coli ribose-binding protein rbsB). Thus it appears that the YFP domain is coming into closer contact with the N-terminal mglB domain, perhaps making some favorable contacts, thus driving the equilibrium slightly towards the open state, and slightly decreasing affinity. Up to the −11aa deletion, signal change and ligand-binding affinity appear to be positively correlated, with higher-affinity sensors also having a higher signal change. This is consistent with the YFP domain having some sort of interaction with the N-terminal domain of mglB in the open state, with the result that affinity is decreased by shifting the equilibrium, and the ratio change is adversely affected, perhaps through quenching. After this amount of deletion, molecular modeling suggests that the YFP is coming into very close proximity to the mglB N- and C-terminal domains, and indeed the −12aa deletion appears as if it may be conformationally restricted by this proximity, resulting in decreased rotational averaging and a higher signal change. Beyond this point, signal change and ligand-binding affinity become negatively correlated, with higher-affinity sensors yielding a lower ratio change. This is consistent with the molecular modeling, and suggests that after this point, the YFP and the mglB open-form N-terminal domain come in sufficient proximity as to give rise to energetically-unfavorable clashes, thus making the closed-form more favorable and increasing affinity.

Deletions beyond 15 amino acids were most sensitive to small deletions, consistent with an overall "tightening" of the allosteric linkage between domains. In this regime, even deletion of a single amino acid reversed the sign of the fluorescence signal change. This is somewhat surprising since similar deletions in the linearly-fused FLIPglu-600Δ13 sensor did not show these dramatic effects. This suggests that perhaps there is some degree of allosteric cross-regulation between the YFP and the loop-inserted CFP, which is modeled to be about 20 Å away, giving rise to the high sensitivity to small deletions.

Effects of deletions targeted solely to the center of the synthetic linker were assayed independently (right section of FIG. 15), and had minimal effect on affinity, as would be expected (the linker is still quite long, and inter-domain contacts are not affected), and a slight increase in signal change, consistent with a slight decrease in the rotational average caused by the likely-unstructured synthetic linker, without any quenching due to deletions of the highly-structured terminal helices of the mglB and YFP domains.

Sensitivity to Environmental Conditions

Figure 16:
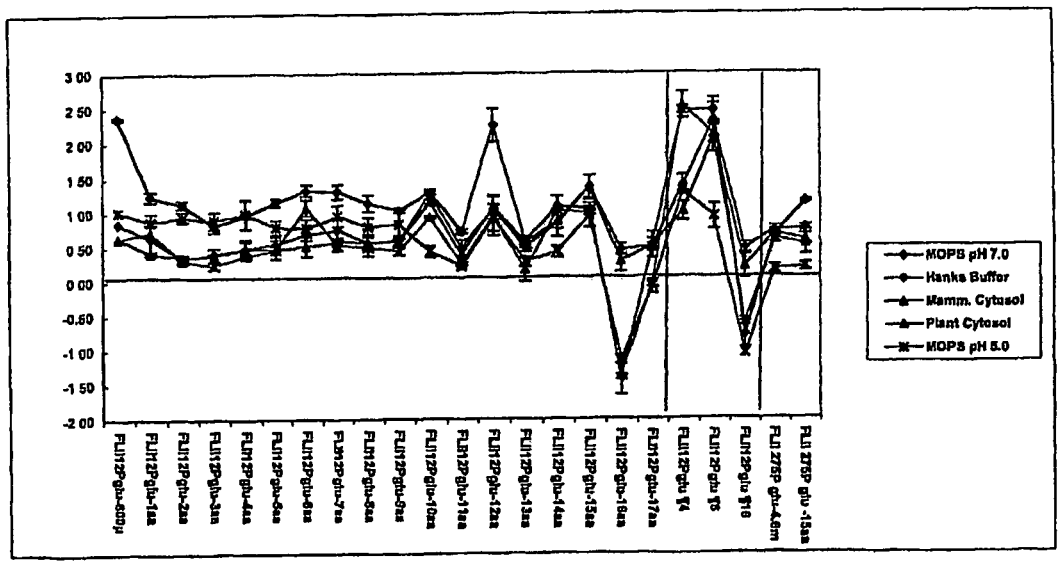
FIG. 16. Sensitivity of the FLII[12]Pglu-600µ deletion constructs to cell culture solution, synthetic cytosols and pH. Comparison of the Δ ratio FLII[12]Pglu-600µ deletion constructs in MOPS pH 7.0 (black), Hanks buffer pH 7.2 (red), Mammalian cytosol pH 7.4 (blue), plant cytosol pH 7.5 (green) and MOPS pH 5.0 (purple). FLII[12]Pglu-10aa, FLII[12]Pglu-14aa, FLII[12]Pglu-15aa and FLII[12]Pglu δ6 can be seen as the sensors least affected by different buffers and low pH.

It has been noted before that buffers can affect ratio change. Moreover, in vivo the ratio change is always dampened owing to various factors such as pH, presence of ions, sugars etc. Therefore, to identify the sensors best suited for in vivo applications, various buffers mimicking cell medium (Hank's), mammalian cytosol, plant cytosol and low pH similar to that inside vesicles, vacuoles or cell wall were tested (Table 8). FLII$^{12}$Pglu-600μ shows a 57% to 74% decrease in ratio change in MOPS pH 5.0 and plant cytosol. Most of the deletion constructs have a 20-70% decreased Δ ratio in various buffers. Of the 5 constructs having a Δ ratio of 1.3 or more, FLII$^{12}$Pglu-6aa and FLII$^{12}$Pglu-7aa are greatly affected by all the buffers tested showing a decreased Δ ratio of 20-61%. FLII$^{12}$Pglu-10aa is unaffected by Hanks buffer and very slightly affected in mammalian cytosol (10% decrease), it shows a 28% decrease in Δ ratio in plant cytosol and a 66% decrease in low pH. FLII$^{12}$Pglu-12aa shows a decrease of 52-59% in all buffers but still has a Δ ratio of 1.0. FLII$^{12}$Pglu-16aa shows a decrease of about 30% in Hanks buffer and mammalian cytosol and is unaffected in plant cytosol and MOPS pH 5.0 but, it completely changes orientation in response to different ions. It shows increase in ratio in Hanks buffer and mammalian cytosol and decrease in ratio in plant cytosol and MOPS pH 5.0 (same as FLII$^{12}$Pglu δ16). FLII$^{12}$Pglu-15aa however is the least affected in all the buffers and even has an improved Δ ratio in Hanks buffer and mammalian cytosol (FIG. 16).

FLIIP$^{275}$Pglu-4.6m is unaffected in Hanks buffer and mammalian cytosol but shows a decreased Δ ratio in plant cytosol (28%) and MOPS pH 5.0 (82%). FLIIP$^{275}$Pglu-15aa showed a 40 and 45% decrease in Hanks buffer and mammalian cytosol respectively, and a 75 and 88% decrease in plant cytosol and low pH (Table 8).

Sensors with the Highest Ratio and Resistance to Environmental Conditions

Though most of the FLII$^{12}$Pglu-600μ deletion constructs have a decreased Δ ratio than the original sensor, they showed more resistance to the environmental conditions tested. The deletion of residues most likely rearranges the sensor in a way that residues most sensitive to ions are no longer exposed thus making the sensor more resistant to environmental conditions.

TABLE 8

Ratio change and affinity of the FLII$^{12}$Pglu-600μ and FLII$^{275}$Pglu-4.6m in MOPS buffer pH 7.0, Hanks buffer, mammalian cytosol, plant cytosol and MOPS buffer pH 5.0

| Sensor Name | MOPS pH 7.0 | | Kd | | HANKS BUFFER | | Mamm cytosol | | Plant cytosol | | MOPS pH 5.0 | |
| --- | --- | --- | --- | --- | --- | --- | --- | --- | --- | --- | --- | --- |
| | Ratio | Stdev | (μM) | Stdev | Ratio | stdev | Ratio | stdev | Ratio | stdev | Ratio | stdev |
| FLIP glu 600μ | −0.29 | 0.0208 | 583 | 8.49 | | | | | | | | |
| FLII$^{12}$Pglu-600μ | 2.37 | 0.0764 | 675 | 45.25 | 0.84 | 0.2056 | 0.64 | 0.0306 | 0.62 | 0.2723 | 1.02 | 0.0354 |
| FLII$^{12}$Pglu-1aa | 1.24 | 0.0624 | 796 | 277.89 | 0.64 | 0.0566 | 0.42 | 0.0283 | 0.73 | 0.0354 | 0.87 | 0.0707 |
| FLII$^{12}$Pglu-2aa | 1.13 | 0.0907 | 1580 | 108.19 | 0.35 | 0.0058 | 0.36 | 0.1021 | 0.31 | 0.0569 | 0.94 | 0.1250 |
| FLII$^{12}$Pglu-3aa | 0.81 | 0.0306 | 1904 | 376.18 | 0.41 | 0.1079 | 0.39 | 0.1380 | 0.24 | 0.0361 | 0.89 | 0.2121 |

TABLE 8-continued

Ratio change and affinity of the FLII$^{12}$Pglu-600μ and FLII$^{275}$Pglu-4.6m in MOPS buffer pH 7.0, Hanks buffer, mammalian cytosol, plant cytosol and MOPS buffer pH 5.0

| Sensor Name | MOPS pH 7.0 | | Kd | | HANKS BUFFER | | Mamm cytosol | | Plant cytosol | | MOPS pH 5.0 | |
|---|---|---|---|---|---|---|---|---|---|---|---|---|
| | Ratio | Stdev | (μM) | Stdev | Ratio | stdev | Ratio | stdev | Ratio | stdev | Ratio | stdev |
| FLII$^{12}$Pglu-4aa | 0.97 | 0.0586 | 1562 | 451.84 | 0.48 | 0.1002 | 0.48 | 0.1380 | 0.38 | 0.0577 | 0.99 | 0.1061 |
| FLII$^{12}$Pglu-5aa | 1.15 | 0.0862 | 1465 | 53.03 | 0.55 | 0.0850 | 0.48 | 0.1450 | 0.46 | 0.1222 | 0.79 | 0.1273 |
| FLII$^{12}$Pglu-6aa | 1.32 | 0.1041 | 1474 | 118.09 | 0.70 | 0.1914 | 0.52 | 0.0557 | 1.07 | 0.0751 | 0.78 | 0.1531 |
| FLII$^{12}$Pglu-7aa | 1.31 | 0.1212 | 1580 | 113.14 | 0.75 | 0.1217 | 0.58 | 0.1997 | 0.53 | 0.0200 | 0.95 | 0.1415 |
| FLII$^{12}$Pglu-8aa | 1.14 | 0.0306 | 1924 | 217.79 | 0.57 | 0.0854 | 0.58 | 0.0551 | 0.51 | 0.0495 | 0.80 | 0.2108 |
| FLII$^{12}$Pglu-9aa | 1.03 | 0.0300 | 1600 | 229.81 | 0.59 | 0.0700 | 0.58 | 0.0252 | 0.44 | 0.0141 | 0.83 | 0.0757 |
| FLII$^{12}$Pglu-10aa | 1.29 | 0.0265 | 1473 | 41.72 | 1.27 | 0.1137 | 1.16 | 0.1159 | 0.94 | 0.0212 | 0.44 | 0.0100 |
| FLII$^{12}$Pglu-11aa | 0.72 | 0.2397 | 1733 | 333.05 | 0.49 | 0.2030 | 0.39 | 0.1701 | 0.26 | 0.2829 | 0.22 | 0.1935 |
| FLII$^{12}$Pglu-12aa | 2.26 | 0.0493 | 1953 | 192.33 | 1.05 | 0.0700 | 1.07 | 0.0874 | 0.95 | 0.1670 | 0.92 | 0.0707 |
| FLII$^{12}$Pglu-13aa | 0.58 | 0.1484 | 2007 | 292.04 | 0.50 | 0.1838 | 0.57 | 0.1061 | 0.17 | 0.0071 | 0.29 | 0.0778 |
| FLII$^{12}$Pglu-14aa | 1.08 | 0.0346 | 3423 | 74.95 | 0.83 | 0.1609 | 0.86 | 0.1758 | 1.02 | 0.0379 | 0.43 | 0.1768 |
| FLII$^{12}$Pglu-15aa | 1.04 | 0.0321 | 2642 | 260.22 | 1.37 | 0.0778 | 1.36 | 0.1626 | 0.99 | 0.2828 | 0.95 | 0.0566 |
| FLII$^{12}$Pglu-16aa | -1.40 | 0.0929 | 1235 | 157.68 | 0.46 | 0.0458 | 0.29 | 0.1858 | -1.37 | 0.0495 | -1.15 | 0.0990 |
| FLII$^{12}$Pglu-17aa | 0.52 | 0.0513 | 6800 | 424.26 | 0.50 | 0.1365 | 0.51 | 0.1332 | -0.04 | 0.1931 | -0.09 | 0.0071 |
| FLII$^{12}$Pglu δ 4 | 2.45 | 0.1767 | 594 | 64.35 | 1.38 | 0.2401 | 1.00 | 0.2060 | 2.53 | 0.1290 | 1.29 | 0.1819 |
| FLII$^{12}$Pglu δ 6 | 2.46 | 0.1890 | 659 | 156.98 | 2.31 | 0.0707 | 2.06 | 0.1697 | 2.12 | 0.0495 | 0.93 | 0.0105 |
| FLII$^{12}$Pglu δ 16 | -0.79 | 0.0100 | 1766 | 221 | 0.48 | 0.0636 | 0.21 | 0.0424 | -0.61 | 0.0707 | -1.07 | 0.0586 |
| FLII$^{275}$Pglu 4.6m | 0.66 | 0.0112 | 5200 | 520 | 0.73 | 0.04 | 0.68 | 0.0707 | 0.62 | 0.1484 | 0.16 | 0.0565 |

Summary and Discussion:

We have accumulated a large data set following the effect residue-by-residue of a series of deletions from the binding protein (BP)-to-fluorescent protein (FP) boundary in a high-signal change loop-inserted glucose sensor FLII$^{12}$Pglu-600μ. Deletions have concomitant effects both on the signal change and glucose-binding affinity of the nanosensor family, consistent with predictions from crude molecular modeling. Of all the sensor modifications, only deletions of one or two amino acids from the center of the synthetic linker connecting the mglB C-terminus with the YFP N-terminus give rise to sensors with higher signal change or higher ligand-binding affinity (in this case, both). All other deletions decrease affinity for glucose, and the glucose-dependent signal change. Some sensors give a higher signal change than the original sensor in different buffer conditions, however, which will be useful for in vivo sensing. Perhaps most importantly, the family of linker-deleted sensors provides a robust data set for the rationalization and design of further linker variants, which may allow high-response sensors to be created out of non-functional ones.

Taken together, the data set supports a model in which local allosteric regulation, particularly of reporter element orientation, plays a significant role in the resonance energy transfer of a family of genetically-encoded nanosensor proteins. Testing of this hypothesis by rational protein design produced sensors with greatly-improved signal-to-noise, enabling a wide array of in vivo applications. Molecular modeling may provide a route to further sensor improvement, and may prove useful in the optimization of other signal transduction mechanisms, such as allosteric enzymatic switches. These findings may be relevant for the optimization of other types of FRET sensors as well as the generation of novel sensors.

Example 8

Testing of FRET Biosensors with Improved Sensitivity In Vivo

Figures 17, 18:
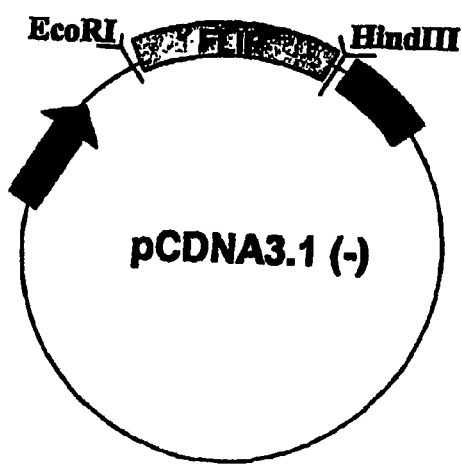
FIG. 17. Diagram showing the constructs of three intramolecular glucose sensors: FLII[12]Pglu-600µ; FLII[12]Pglu δ4aa-593µ, and FLII[275]Pglu-4600µ.
FIG. 18. Diagram showing the FLIP constructs in pc DNA3.1.
Figure 19A:
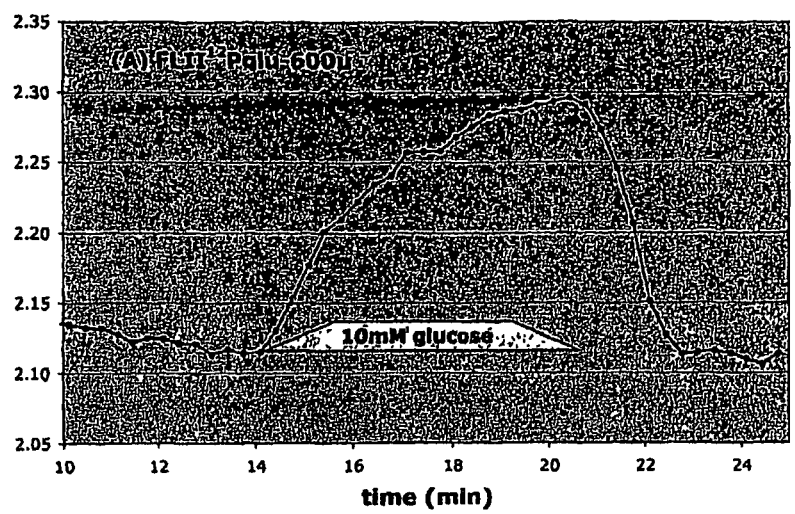
FIG. 19. FRET changes observed in NIH3T3 cells transformed with the improved glucose sensors. (A) Perfusion of NIH3T3-L1 cells transiently cytosolic expressing by FLII[12]Pglu-600µ, (B) FLII[12]Pglu δ4aa-593µ and (C) FLII[275]Pglu-4600µ. The bars indicate the presence of 10 mM glucose in the perfusion buffer.
Figure 19B:
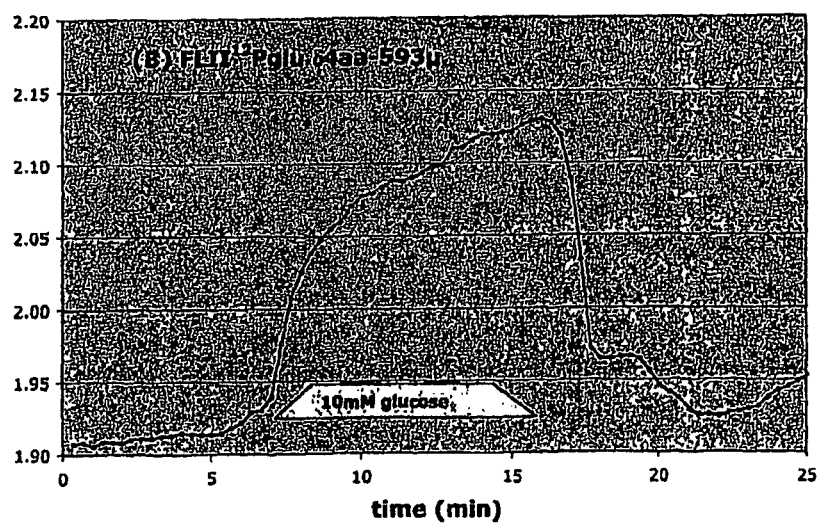
Figure 19C:
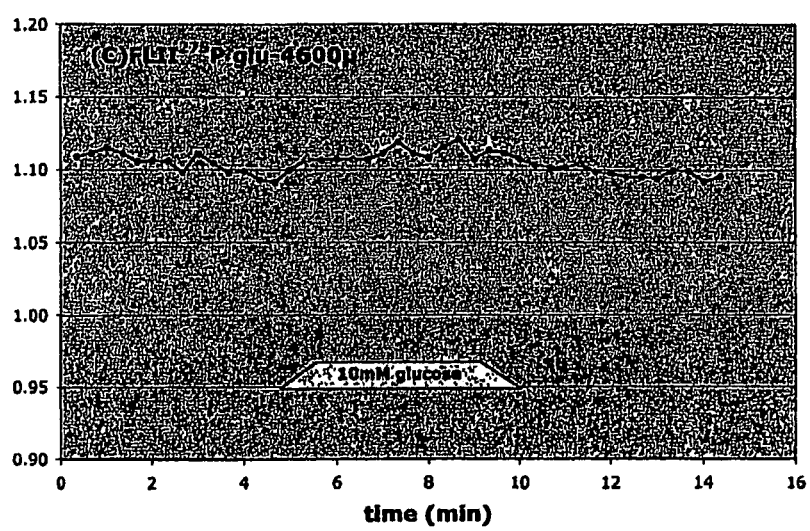

To test the improved sensors for glucose detection in living cells and to test whether the sensors can be used also in other cell types, three intramolecular sensors (FLII$^{12}$Pglu-6001μ; FLII$^{12}$Pglu δ4aa-593μ; FLII$^{275}$Pglu-4600μ; FIG. 17) were cloned into pcDNA3.1 (−) (FIG. 18). FIG. 19 shows FRET changes observed in NIH3T3 cells transformed with the improved glucose sensors.

All publications, patents and patent applications discussed herein are incorporated herein by reference. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed:

1. An isolated nucleic acid comprising a polynucleotide sequence which encodes: a glutamate-aspartate receptor (YbeJ) comprising the amino acid sequence of SEQ, ID NO: 28, wherein the YbeJ specifically binds a glutamate or aspartate, and at least one of a donor fluorophore protein moiety fused to the YbeJ or an acceptor fluorophore protein moiety fused to the YbeJ, wherein the coding region of the donor fluorophore protein moiety is inserted between amino acids 58 and 59 of SEQ, ID NO: 28, and the coding region of the acceptor fluorophore protein moiety is inserted at an internal site of the coding region of said YbeJ.

2. The isolated nucleic acid of claim 1, wherein said coding region of the donor fluorescent protein moiety and said coding region of the acceptor fluorescent protein moiety are fused to the same lobe of said YbeJ.

3. The isolated nucleic acid of claim 1, wherein said coding region of the acceptor fluorophore protein moiety is inserted at the C-terminus of said YbeJ.

4. The isolated nucleic acid of claim 1, wherein said donor fluorophore protein moiety is selected from the group consisting of a GFP, a CFP, a BFP, a YFP, a dsRED, CoralHue Midoriishi-Cyan (MiCy) and monomeric CoralHue Kusabira-Orange (mKO).

5. The isolated nucleic acid of claim 1, wherein said acceptor fluorophore protein moiety is selected from the group consisting of a GFP, a CFP, a BFP, a YFP, a dsRED, CoralHue Midoriishi-Cyan (MiCy) and monomeric CoralHue Kusabira-Orange (mKO).

6. The isolated nucleic acid of claim 4, wherein the donor fluorophore protein moiety is eCFP.

7. The isolated nucleic acid of claim 5, wherein the acceptor fluorophore protein moiety is YFP VENUS.

8. The isolated nucleic acid of claim 1, further comprising at least one linker moiety that links the internal site of the YbeJ to the at least one donor fluorophore protein moiety or acceptor fluorophore protein moiety.

9. An expression vector comprising the nucleic acid of claim 1 or 8.

10. A cell comprising the vector of claim 9.

11. The isolated nucleic acid of claim 1, further comprising one or more nucleic acid substitutions that modify the affinity of the YbeJ to glutamate or aspartate.

12. A ligand binding fluorescent indicator encoded by the nucleic acid of claim 1 or 8.

* * * * *

SEQUENCE LISTING

```
<160> NUMBER OF SEQ ID NOS: 59

<210> SEQ ID NO 1
<211> LENGTH: 978
<212> TYPE: DNA
<213> ORGANISM: Escherichia coli K12
<220> FEATURE:
<221> NAME/KEY: CDS
<222> LOCATION: (1)..(978)
```

<400> SEQUENCE: 1

```
atg ata aca aca caa aca ctc aca acg ggt atc cat gcg ttc tta acg      48
Met Ile Thr Thr Gln Thr Leu Thr Thr Gly Ile His Ala Phe Leu Thr
1               5                   10                  15 cag aag ata aag gag ttg gat atg caa tta cgt aaa cct gcc aca gca      96
Gln Lys Ile Lys Glu Leu Asp Met Gln Leu Arg Lys Pro Ala Thr Ala
            20                  25                  30 atc ctc gcc ctg gcg ctt tcc gca gga ctg gca cag gca gat gac gcc     144
Ile Leu Ala Leu Ala Leu Ser Ala Gly Leu Ala Gln Ala Asp Asp Ala
        35                  40                  45 gcc ccg gca gcg ggc agt act ctg gac aaa atc gcc aaa aac ggt gtg     192
Ala Pro Ala Ala Gly Ser Thr Leu Asp Lys Ile Ala Lys Asn Gly Val
    50                  55                  60 att gtc gtc ggt cac cgt gaa tct tca gtg cct ttc tct tat tac gac     240
Ile Val Val Gly His Arg Glu Ser Ser Val Pro Phe Ser Tyr Tyr Asp
65                  70                  75                  80 aat cag caa aaa gtg gtg ggt tac tcg cag gat tac tcc aac gcc att     288
Asn Gln Gln Lys Val Val Gly Tyr Ser Gln Asp Tyr Ser Asn Ala Ile
                85                  90                  95 gtt gaa gca gtg aaa aag aaa ctc aac aaa ccg gac ttg cag gta aaa     336
Val Glu Ala Val Lys Lys Lys Leu Asn Lys Pro Asp Leu Gln Val Lys
            100                 105                 110 ctg att ccg att acc tca caa aac cgt att cca ctg ctg caa aac ggc     384
Leu Ile Pro Ile Thr Ser Gln Asn Arg Ile Pro Leu Leu Gln Asn Gly
        115                 120                 125 act ttc gat ttt gaa tgt ggt tct acc acc aac aac gtc gaa cgc caa     432
Thr Phe Asp Phe Glu Cys Gly Ser Thr Thr Asn Asn Val Glu Arg Gln
    130                 135                 140 aaa cag gcg gct ttc tct gac act att ttc gtg gtc ggt acg cgc ctg     480
Lys Gln Ala Ala Phe Ser Asp Thr Ile Phe Val Val Gly Thr Arg Leu
145                 150                 155                 160 ttg acc aaa aag ggt ggc gat atc aaa gat ttt gcc aac ctg aaa gac     528
Leu Thr Lys Lys Gly Gly Asp Ile Lys Asp Phe Ala Asn Leu Lys Asp
                165                 170                 175 aaa gcc gta gtc gtc act tcc ggc act acc tct gaa gtt ttg ctc aac     576
Lys Ala Val Val Val Thr Ser Gly Thr Thr Ser Glu Val Leu Leu Asn
            180                 185                 190 aaa ctg aat gaa gag caa aaa atg aat atg cgc atc atc agc gcc aaa     624
Lys Leu Asn Glu Glu Gln Lys Met Asn Met Arg Ile Ile Ser Ala Lys
        195                 200                 205 gat cac ggt gac tct ttc cgc acc ctg gaa agc ggt cgt gcc gtt gcc     672
Asp His Gly Asp Ser Phe Arg Thr Leu Glu Ser Gly Arg Ala Val Ala
    210                 215                 220 ttt atg atg gat gac gct ctg ctg gcc ggt gaa cgt gcg aaa gcg aag     720
Phe Met Met Asp Asp Ala Leu Leu Ala Gly Glu Arg Ala Lys Ala Lys
225                 230                 235                 240 aaa cca gac aac tgg gaa atc gtc ggc aag ccg cag tct cag gag gcc     768
Lys Pro Asp Asn Trp Glu Ile Val Gly Lys Pro Gln Ser Gln Glu Ala
                245                 250                 255 tac ggt tgt atg ttg cgt aaa gat gat ccg cag ttc aaa aag ctg atg     816
Tyr Gly Cys Met Leu Arg Lys Asp Asp Pro Gln Phe Lys Lys Leu Met
            260                 265                 270 gat gac acc atc gct cag gtg cag acc tcc ggt gaa gcg gaa aaa tgg     864
Asp Asp Thr Ile Ala Gln Val Gln Thr Ser Gly Glu Ala Glu Lys Trp
        275                 280                 285 ttt gat aag tgg ttc aaa aat cca att ccg ccg aaa aac ctg aac atg     912
Phe Asp Lys Trp Phe Lys Asn Pro Ile Pro Pro Lys Asn Leu Asn Met
    290                 295                 300
```

-continued

```
aat ttc gaa ctg tca gac gaa atg aaa gca ctg ttc aaa gaa ccg aat    960
Asn Phe Glu Leu Ser Asp Glu Met Lys Ala Leu Phe Lys Glu Pro Asn
305                 310                 315                 320 gac aag gca ctg aac taa                                             978
Asp Lys Ala Leu Asn
            325
```

<210> SEQ ID NO 2
<211> LENGTH: 325
<212> TYPE: PRT
<213> ORGANISM: Escherichia coli K12

<400> SEQUENCE: 2

```
Met Ile Thr Thr Gln Thr Leu Thr Thr Gly Ile His Ala Phe Leu Thr
1               5                   10                  15

Gln Lys Ile Lys Glu Leu Asp Met Gln Leu Arg Lys Pro Ala Thr Ala
            20                  25                  30

Ile Leu Ala Leu Ala Leu Ser Ala Gly Leu Ala Gln Ala Asp Asp Ala
        35                  40                  45

Ala Pro Ala Ala Gly Ser Thr Leu Asp Lys Ile Ala Lys Asn Gly Val
50                  55                  60

Ile Val Val Gly His Arg Glu Ser Ser Val Pro Phe Ser Tyr Tyr Asp
65                  70                  75                  80

Asn Gln Gln Lys Val Gly Tyr Ser Gln Asp Tyr Ser Asn Ala Ile
                85                  90                  95

Val Glu Ala Val Lys Lys Leu Asn Lys Pro Asp Leu Gln Val Lys
                100                 105                 110

Leu Ile Pro Ile Thr Ser Gln Asn Arg Ile Pro Leu Leu Gln Asn Gly
            115                 120                 125

Thr Phe Asp Phe Glu Cys Gly Ser Thr Thr Asn Val Glu Arg Gln
    130                 135                 140

Lys Gln Ala Ala Phe Ser Asp Thr Ile Phe Val Val Gly Thr Arg Leu
145                 150                 155                 160

Leu Thr Lys Lys Gly Gly Asp Ile Lys Asp Phe Ala Asn Leu Lys Asp
                165                 170                 175

Lys Ala Val Val Val Thr Ser Gly Thr Thr Ser Glu Val Leu Leu Asn
                180                 185                 190

Lys Leu Asn Glu Glu Gln Lys Met Asn Met Arg Ile Ile Ser Ala Lys
            195                 200                 205

Asp His Gly Asp Ser Phe Arg Thr Leu Glu Ser Gly Arg Ala Val Ala
    210                 215                 220

Phe Met Met Asp Asp Ala Leu Leu Ala Gly Glu Arg Ala Lys Ala Lys
225                 230                 235                 240

Lys Pro Asp Asn Trp Glu Ile Val Gly Lys Pro Gln Ser Gln Glu Ala
                245                 250                 255

Tyr Gly Cys Met Leu Arg Lys Asp Asp Pro Gln Phe Lys Lys Leu Met
            260                 265                 270

Asp Asp Thr Ile Ala Gln Val Gln Thr Ser Gly Glu Ala Glu Lys Trp
        275                 280                 285

Phe Asp Lys Trp Phe Lys Asn Pro Ile Pro Lys Asn Leu Asn Met
    290                 295                 300

Asn Phe Glu Leu Ser Asp Glu Met Lys Ala Leu Phe Lys Glu Pro Asn
305                 310                 315                 320

Asp Lys Ala Leu Asn
            325
```

<210> SEQ ID NO 3
<211> LENGTH: 810
<212> TYPE: DNA
<213> ORGANISM: Escherichia coli K12
<220> FEATURE:
<221> NAME/KEY: CDS
<222> LOCATION: (1)..(810)

<400> SEQUENCE: 3

| | | | | | | | | | | | | | | | | |
|---|---|---|---|---|---|---|---|---|---|---|---|---|---|---|---|---|
| ctg | gac | aaa | atc | gcc | aaa | aac | ggt | gtg | att | gtc | gtc | ggt | cac | cgt | gaa | 48 |
| Leu | Asp | Lys | Ile | Ala | Lys | Asn | Gly | Val | Ile | Val | Val | Gly | His | Arg | Glu | |
| 1 | | | | 5 | | | | | 10 | | | | | 15 | | |
| tct | tca | gtg | cct | ttc | tct | tat | tac | gac | aat | cag | caa | aaa | gtg | gtg | ggt | 96 |
| Ser | Ser | Val | Pro | Phe | Ser | Tyr | Tyr | Asp | Asn | Gln | Gln | Lys | Val | Val | Gly | |
| | | | 20 | | | | | 25 | | | | | 30 | | | |
| tac | tcg | cag | gat | tac | tcc | aac | gcc | att | gtt | gaa | gca | gtg | aaa | aag | aaa | 144 |
| Tyr | Ser | Gln | Asp | Tyr | Ser | Asn | Ala | Ile | Val | Glu | Ala | Val | Lys | Lys | Lys | |
| | 35 | | | | | 40 | | | | | 45 | | | | | |
| ctc | aac | aaa | ccg | gac | ttg | cag | gta | aaa | ctg | att | ccg | att | acc | tca | caa | 192 |
| Leu | Asn | Lys | Pro | Asp | Leu | Gln | Val | Lys | Leu | Ile | Pro | Ile | Thr | Ser | Gln | |
| 50 | | | | | 55 | | | | | 60 | | | | | | |
| aac | cgt | att | cca | ctg | ctg | caa | aac | ggc | act | ttc | gat | ttt | gaa | tgt | ggt | 240 |
| Asn | Arg | Ile | Pro | Leu | Leu | Gln | Asn | Gly | Thr | Phe | Asp | Phe | Glu | Cys | Gly | |
| 65 | | | | | 70 | | | | | 75 | | | | | 80 | |
| tct | acc | acc | aac | aac | gtc | gaa | cgc | caa | aaa | cag | gcg | gct | ttc | tct | gac | 288 |
| Ser | Thr | Thr | Asn | Asn | Val | Glu | Arg | Gln | Lys | Gln | Ala | Ala | Phe | Ser | Asp | |
| | | | | 85 | | | | | 90 | | | | | 95 | | |
| act | att | ttc | gtg | gtc | ggt | acg | cgc | ctg | ttg | acc | aaa | aag | ggt | ggc | gat | 336 |
| Thr | Ile | Phe | Val | Val | Gly | Thr | Arg | Leu | Leu | Thr | Lys | Lys | Gly | Gly | Asp | |
| | | | 100 | | | | | 105 | | | | | 110 | | | |
| atc | aaa | gat | ttt | gcc | aac | ctg | aaa | gac | aaa | gcc | gta | gtc | gtc | act | tcc | 384 |
| Ile | Lys | Asp | Phe | Ala | Asn | Leu | Lys | Asp | Lys | Ala | Val | Val | Val | Thr | Ser | |
| | 115 | | | | | 120 | | | | | 125 | | | | | |
| ggc | act | acc | tct | gaa | gtt | ttg | ctc | aac | aaa | ctg | aat | gaa | gag | caa | aaa | 432 |
| Gly | Thr | Thr | Ser | Glu | Val | Leu | Leu | Asn | Lys | Leu | Asn | Glu | Glu | Gln | Lys | |
| 130 | | | | | 135 | | | | | 140 | | | | | | |
| atg | aat | atg | cgc | atc | atc | agc | gcc | aaa | gat | cac | ggt | gac | tct | ttc | cgc | 480 |
| Met | Asn | Met | Arg | Ile | Ile | Ser | Ala | Lys | Asp | His | Gly | Asp | Ser | Phe | Arg | |
| 145 | | | | | 150 | | | | | 155 | | | | | 160 | |
| acc | ctg | gaa | agc | ggt | cgt | gcc | gtt | gcc | ttt | atg | atg | gat | gac | gct | ctg | 528 |
| Thr | Leu | Glu | Ser | Gly | Arg | Ala | Val | Ala | Phe | Met | Met | Asp | Asp | Ala | Leu | |
| | | | | 165 | | | | | 170 | | | | | 175 | | |
| ctg | gcc | ggt | gaa | cgt | gcg | aaa | gcg | aag | aaa | cca | gac | aac | tgg | gaa | atc | 576 |
| Leu | Ala | Gly | Glu | Arg | Ala | Lys | Ala | Lys | Lys | Pro | Asp | Asn | Trp | Glu | Ile | |
| | | | 180 | | | | | 185 | | | | | 190 | | | |
| gtc | ggc | aag | ccg | cag | tct | cag | gag | gcc | tac | ggt | tgt | atg | ttg | cgt | aaa | 624 |
| Val | Gly | Lys | Pro | Gln | Ser | Gln | Glu | Ala | Tyr | Gly | Cys | Met | Leu | Arg | Lys | |
| | 195 | | | | | 200 | | | | | 205 | | | | | |
| gat | gat | ccg | cag | ttc | aaa | aag | ctg | atg | gat | gac | acc | atc | gct | cag | gtg | 672 |
| Asp | Asp | Pro | Gln | Phe | Lys | Lys | Leu | Met | Asp | Asp | Thr | Ile | Ala | Gln | Val | |
| 210 | | | | | 215 | | | | | 220 | | | | | | |
| cag | acc | tcc | ggt | gaa | gcg | gaa | aaa | tgg | ttt | gat | aag | tgg | ttc | aaa | aat | 720 |
| Gln | Thr | Ser | Gly | Glu | Ala | Glu | Lys | Trp | Phe | Asp | Lys | Trp | Phe | Lys | Asn | |
| 225 | | | | | 230 | | | | | 235 | | | | | 240 | |
| cca | att | ccg | ccg | aaa | aac | ctg | aac | atg | aat | ttc | gaa | ctg | tca | gac | gaa | 768 |
| Pro | Ile | Pro | Pro | Lys | Asn | Leu | Asn | Met | Asn | Phe | Glu | Leu | Ser | Asp | Glu | |
| | | | | 245 | | | | | 250 | | | | | 255 | | |
| atg | aaa | gca | ctg | ttc | aaa | gaa | ccg | aat | gac | aag | gca | ctg | aac | | | 810 |
| Met | Lys | Ala | Leu | Phe | Lys | Glu | Pro | Asn | Asp | Lys | Ala | Leu | Asn | | | |
| | | | 260 | | | | | 265 | | | | | 270 | | | |

<210> SEQ ID NO 4

```
<211> LENGTH: 270
<212> TYPE: PRT
<213> ORGANISM: Escherichia coli K12

<400> SEQUENCE: 4

Leu Asp Lys Ile Ala Lys Asn Gly Val Ile Val Gly His Arg Glu
1               5                   10                  15

Ser Ser Val Pro Phe Ser Tyr Tyr Asp Asn Gln Gln Lys Val Val Gly
            20                  25                  30

Tyr Ser Gln Asp Tyr Ser Asn Ala Ile Val Glu Ala Val Lys Lys Lys
        35                  40                  45

Leu Asn Lys Pro Asp Leu Gln Val Lys Leu Ile Pro Ile Thr Ser Gln
50                  55                  60

Asn Arg Ile Pro Leu Leu Gln Asn Gly Thr Phe Asp Phe Glu Cys Gly
65                  70                  75                  80

Ser Thr Thr Asn Asn Val Glu Arg Gln Lys Gln Ala Ala Phe Ser Asp
                85                  90                  95

Thr Ile Phe Val Val Gly Thr Arg Leu Leu Thr Lys Lys Gly Gly Asp
            100                 105                 110

Ile Lys Asp Phe Ala Asn Leu Lys Asp Lys Ala Val Val Val Thr Ser
        115                 120                 125

Gly Thr Thr Ser Glu Val Leu Leu Asn Lys Leu Asn Glu Glu Gln Lys
130                 135                 140

Met Asn Met Arg Ile Ile Ser Ala Lys Asp His Gly Asp Ser Phe Arg
145                 150                 155                 160

Thr Leu Glu Ser Gly Arg Ala Val Ala Phe Met Met Asp Asp Ala Leu
                165                 170                 175

Leu Ala Gly Glu Arg Ala Lys Ala Lys Lys Pro Asp Asn Trp Glu Ile
            180                 185                 190

Val Gly Lys Pro Gln Ser Gln Glu Ala Tyr Gly Cys Met Leu Arg Lys
        195                 200                 205

Asp Asp Pro Gln Phe Lys Lys Leu Met Asp Asp Thr Ile Ala Gln Val
210                 215                 220

Gln Thr Ser Gly Glu Ala Glu Lys Trp Phe Asp Lys Trp Phe Lys Asn
225                 230                 235                 240

Pro Ile Pro Pro Lys Asn Leu Asn Met Asn Phe Glu Leu Ser Asp Glu
                245                 250                 255

Met Lys Ala Leu Phe Lys Glu Pro Asn Asp Lys Ala Leu Asn
            260                 265                 270

<210> SEQ ID NO 5
<211> LENGTH: 39
<212> TYPE: DNA
<213> ORGANISM: Artificial Sequence
<220> FEATURE:
<223> OTHER INFORMATION: Primer

<400> SEQUENCE: 5
ggtaccggag gcgccgcagg cagcacgctg gacaaaatc                              39

<210> SEQ ID NO 6
<211> LENGTH: 39
<212> TYPE: DNA
<213> ORGANISM: Artificial Sequence
<220> FEATURE:
<223> OTHER INFORMATION: Primer

<400> SEQUENCE: 6
accggtaccg gcgccgttca gtgccttgtc attcggttc                              39
```

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
gagcccggga tggtgagcaa gggcgaggag                                    30

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
gaggtcgacc ttgtacagct cgtccatgcc gag                                33

<210> SEQ ID NO 9
<211> LENGTH: 5206
<212> TYPE: DNA
<213> ORGANISM: Artificial Sequence
<220> FEATURE:
<223> OTHER INFORMATION: DNA sequence of pRSETB FLIP-E 600n vector

<400> SEQUENCE: 9
atctcgatcc cgcgaaatta atacgactca ctatagggag accacaacgg tttccctcta     60
gataattttg tttaacttta agaaggagat atacatatgc ggggttctca tcatcatcat    120
catcatggta tggctagcat gactggtgga cagcaaatgg gtcggatct gtacgacgat     180 gacgataagg atccgggccg catggtgagc aagggcgagg agctgttcac cggggtggtg    240
cccatcctgg tcgagctgga cggcgacgta aacggccaca gttcagcgt gtccggcgag     300 ggcgagggcg atgccaccta cggcaagctg accctgaagt tcatctgcac caccggcaag    360
ctgcccgtgc cctggcccac cctcgtgacc accctgacct ggggcgtgca gtgcttcagc    420
cgctaccccg accacatgaa gcagcacgac ttcttcaagt ccgccatgcc cgaaggctac    480
gtccaggagc gcaccatctt cttcaaggac gacggcaact acaagacccg cgccgaggtg    540
aagttcgagg gcgacaccct ggtgaaccgc atcgagctga agggcatcga cttcaaggag    600
gacggcaaca tcctggggca caagctggag tacaactaca tcagccacaa cgtctatatc    660
accgccgaca gcagaagaa cggcatcaag gccaacttca gatccgcca caacatcgag     720 gacggcagcg tgcagctcgc cgaccactac cagcagaaca cccccatcgg cgacggcccc    780
gtgctgctgc ccgacaacca ctacctgagc acccagtccg ccctgagcaa agaccccaac    840
gagaagcgcg atcacatggt cctgctggag ttcgtgaccg ccgccgggat cactctcggc    900
atggacgagc tgtacaaggg tggtaccgga ggcgccgcag gcagcacgct ggacaaaatc    960
gccaaaaacg gtgtgattgt cgtcggtcac cgtgaatctt cagtgccttt ctcttattac   1020
gacaatcagc aaaaagtggt gggttactcg caggattact ccaacgccat tgttgaagca   1080
gtgaaaaaga aactcaacaa accggacttg caggtaaaac tgattccgat tacctcacaa   1140
aaccgtattc cactgctgca aacggcact ttcgattttg aatgtggttc taccaccaac   1200
aacgtcgaac gccaaaaaca ggcggctttc tctgacacta ttttcgtggt cggtacgcgc   1260
ctgttgacca aaaagggtgg cgatatcaaa gattttgcca acctgaaaga caagccgta   1320 gtcgtcactt ccggcactac ctctgaagtt ttgctcaaca aactgaatga agagcaaaaa   1380

```
atgaatatgc gcatcatcag cgccaaagat cacggtgact ctttccgcac cctggaaagc   1440
ggtcgtgccg ttgcctttat gatggatgac gctctgctgg ccggtgaacg tgcgaaagcg   1500
aagaaaccag acaactggga atcgtcggc aagccgcagt ctcaggaggc ctacggttgt    1560
atgttgcgta aagatgatcc gcagttcaaa aagctgatgg atgacaccat cgctcaggtg   1620
cagacctccg gtgaagcgga aaatggtttt gataagtggt tcaaaaatcc aattccgccg   1680
aaaaacctga acatgaattt cgaactgtca gacgaaatga agcactgtt caaagaaccg    1740 aatgacaagg cactgaacgg cgccggtacc ggtggaatgg tgagcaaggg cgaggagctg   1800
ttcaccgggg tggtgcccat cctggtcgag ctggacggcg acgtaaacgg ccacaagttc   1860
agcgtgtccg gcgagggcga gggcgatgcc acctacggca agctgaccct gaagttcatc   1920
tgcaccaccg gcaagctgcc cgtgccctgg cccaccctcg tgaccacctt cggctacggc   1980
ctgcagtgct tcgcccgcta ccccgaccac atgaagcagc acgacttctt caagtccgcc   2040
atgcccgaag ctacgtcca ggagcgcacc atcttcttca aggacgacgg caactacaag    2100
acccgcgccg aggtgaagtt cgagggcgac accctggtga accgcatcga gctgaagggc   2160
atcgacttca aggaggacgg caacatcctg gggcacaagc tggagtacaa ctacaacagc   2220
cacaacgtct atatcatggc cgacaagcag aagaacggca tcaaggtgaa cttcaagatc   2280
cgccacaaca tcgaggacgg cagcgtgcag ctcgccgacc actaccagca gaacaccccc   2340
atcggcgacg gccccgtgct gctgcccgac aaccactacc tgagctacca gtccgccctg   2400
agcaaagacc ccaacgagaa gcgcgatcac atggtcctgc tggagttcgt gaccgccgcc   2460
gggatcactc tcggcatgga cgagctgtac aagtaaaagc ttgatccggc tgctaacaaa   2520
gcccgaaagg aagctgagtt ggctgctgcc accgctgagc aataactagc ataacccctt   2580
ggggcctcta acgggtctt gagggggttt tgctgaaag gaggaactat atccggatct     2640
ggcgtaatag cgaagaggcc cgcaccgatc gcccttccca acagttgcgc agcctgaatg   2700
gcgaatggga cgcgccctgt agcggcgcat taagcgcggc gggtgtggtg gttacgcgca   2760
gcgtgaccgc tacacttgcc agcgccctag cgcccgctcc tttcgctttc ttcccttcct   2820
ttctcgccac gttcgccggc tttccccgtc aagctctaaa tcggggctc cctttagggt    2880 tccgatttag agctttacgg cacctcgacc gcaaaaaact tgatttgggt gatggttcac   2940
gtagtgggcc atcgccctga tagacggttt ttcgcccttt gacgttggag tccacgttct   3000
ttaatagtgg actcttgttc caaactggaa caacactcaa ccctatcgcg gtctattctt   3060
ttgatttata agggattttg ccgatttcgg cctattggtt aaaaaatgag ctgatttaac   3120
aaatatttaa cgcgaatttt aacaaaatat taacgtttac aatttcgcct gatgcggtat   3180
tttctcctta cgcatctgtg cggtatttca caccgcatac aggtggcact tttcggggaa   3240
atgtgcgcgg aacccctatt tgtttatttt tctaaataca ttcaaatatg tatccgctca   3300
tgagacaata accctgataa atgcttcaat aatattgaaa aaggaagagt atgagtattc   3360
aacatttccg tgtcgccctt attccctttt tgcggcatt ttgccttcct gtttttgctc    3420
acccagaaac gctggtgaaa gtaaaagatg ctgaagatca gttgggtgca cgagtgggtt   3480
acatcgaact ggatctcaac agcggtaaga tccttgagag ttttcgcccc gaagaacgtt   3540
ttccaatgat gagcactttt aaagttctgc tatgtgatac actattatcc cgtattgacg   3600
ccgggcaaga gcaactcggt cgccgcatac actattctca gaatgacttg gttgagtact   3660
caccagtcac agaaaagcat cttacggatg gcatgacagt aagagaatta tgcagtgctg   3720
ccataaccat gagtgataac actgcggcca acttacttct gacaacgatc ggaggaccga   3780
```

```
aggagctaac cgcttttttg cacaacatgg gggatcatgt aactcgcctt gatcgttggg    3840
aaccggagct gaatgaagcc ataccaaacg acgagagtga caccacgatg cctgtagcaa    3900
tgccaacaac gttgcgcaaa ctattaactg gcgaactact tactctagct tcccggcaac    3960
aattaataga ctgaatggag gcggataaag ttgcaggacc acttctgcgc tcggcccttc    4020
cggctggctg gtttattgct gataaatctg gagccggtga gcgtgggtct cgcggtatca    4080
ttgcagcact ggggccagat ggtaagcgct cccgtatcgt agttatctac acgacgggga    4140
gtcaggcaac tatggatgaa cgaaatagac agatcgctga gataggtgcc tcactgatta    4200
agcattggta actgtcagac caagtttact catatatact ttagattgat ttaaaacttc    4260
atttttaatt taaaaggatc taggtgaaga tcctttttga taatctcatg accaaaatcc    4320
cttaacgtga gttttcgttc cactgagcgt cagaccccgt agaaaagatc aaaggatctt    4380
cttgagatcc ttttttttctg cgcgtaatct gctgcttgca acaaaaaaa ccaccgctac    4440 cagcggtggt ttgtttgccg gatcaagagc taccaactct ttttccgaag gtaactggct    4500
tcagcagagc gcagatacca atactgtcc ttctagtgta gccgtagtta ggccaccact    4560
tcaagaactc tgtagcaccg cctacatacc tcgctctgct aatcctgtta ccagtggctg    4620
ctgccagtgg cgataagtcg tgtcttaccg ggttggactc aagacgatag ttaccggata    4680
aggcgcagcg gtcgggctga acggggggtt cgtgcacaca gcccagcttg gagcgaacga    4740
cctacaccga actgagatac ctacagcgtg agctatgaga aagcgccacg cttcccgaag    4800
ggagaaaggc ggacaggtat ccggtaagcg gcagggtcgg aacaggagag cgcacgaggg    4860
agcttccagg gggaaacgcc tggtatcttt atagtcctgt cgggtttcgc cacctctgac    4920
ttgagcgtcg atttttgtga tgctcgtcag ggggggcggag cctatggaaa aacgccagca    4980
acgcggcctt tttacggttc ctgggctttt gctggccttt tgctcacatg ttctttcctg    5040
cgttatcccc tgattctgtg gataaccgta ttaccgcctt tgagtgagct gataccgctc    5100
gccgcagccg aacgaccgag cgcagcgagt cagtgagcga ggaagcggaa gagcgcccaa    5160
tacgcaaacc gcctctcccc gcgcgttggc cgattcatta atgcag        5206
```

<210> SEQ ID NO 10
<211> LENGTH: 5206
<212> TYPE: DNA
<213> ORGANISM: Artificial Sequence
<220> FEATURE:
<223> OTHER INFORMATION: DNA sequence of pRSETB FLIP-E 10u vector

<400> SEQUENCE: 10

```
atctcgatcc cgcgaaatta atacgactca ctatagggag accacaacgg tttccctcta      60
gataattttg tttaacttta agaaggagat atacatatgc ggggttctca tcatcatcat     120
catcatggta tggctagcat gactggtgga cagcaaatgg gtcgggatct gtacgacgat     180
gacgataagg atccgggccg catggtgagc aagggcgagg agctgttcac cggggtggtg     240
cccatcctgg tcgagctgga cggcgacgta aacggccaca agttcagcgt gtccggcgag     300
ggcgagggcg atgccaccta cggcaagctg accctgaagt tcatctgcac caccggcaag     360
ctgcccgtgc cctggcccac cctcgtgacc accctgacct ggggcgtgca gtgcttcagc     420
cgctaccccg accacatgaa gcagcacgac ttcttcaagt ccgccatgcc cgaaggctac     480
gtccaggagc gcaccatctt cttcaaggac gacggcaact acaagacccg cgccgaggtg     540
aagttcgagg gcgacaccct ggtgaaccgc atcgagctga agggcatcga cttcaaggag     600
gacggcaaca tcctggggca caagctggag tacaactaca tcagccacaa cgtctatatc     660
```

```
accgccgaca agcagaagaa cggcatcaag gccaacttca agatccgcca caacatcgag    720
gacggcagcg tgcagctcgc cgaccactac cagcagaaca ccccatcgg cgacggcccc    780 gtgctgctgc ccgacaacca ctacctgagc acccagtccg ccctgagcaa agaccccaac    840
gagaagcgcg atcacatggt cctgctggag ttcgtgaccg ccgccgggat cactctcggc    900
atggacgagc tgtacaaggg tggtaccgga ggcgccgcag gcagcacgct ggacaaaatc    960
gccaaaaacg gtgtgattgt cgtcggtcac cgtgaatctt cagtgccttt ctcttattac   1020
gacaatcagc aaaaagtggt gggttactcg caggattact ccaacgccat tgttgaagca   1080
gtgaaaaaga aactcaacaa accggacttg caggtaaaac tgattccgat tacctcacaa   1140
aaccgtattc cactgctgca aaacggcact ttcgattttg aatgtggttc taccaccaac   1200
aacgtcgaac gccaaaaaca ggcggctttc tctgacacta ttttcgtggt cggtacgcgc   1260
ctgttgacca aaagggtgg cgatatcaaa gattttgcca acctgaaaga caaagccgta   1320
gtcgtcactt ccggcactac ctctgaagtt ttgctcaaca aactgaatga agagcaaaaa   1380
atgaatatgc gcatcatcag cgccaaagat cacggtgact ctttccgcac cctggaaagc   1440
ggtcgtgccg ttgcctttat gatggatgac cggctgctgg ccggtgaacg tgcgaaagcg   1500
aagaaaccag acaactggga atcgtcggc aagccgcagt ctcaggaggc ctacggttgt   1560
atgttgcgta agatgatcc gcagttcaaa aagctgatgg atgacaccat cgctcaggtg   1620
cagacctccg gtgaagcgga aaatggtttt gataagtggt tcaaaaatcc aattccgccg   1680
aaaaacctga acatgaattt cgaactgtca gacgaaatga agcactgtt caaagaaccg   1740 aatgacaagg cactgaacgg cgccggtacc ggtggaatgg tgagcaaggg cgaggagctg   1800
ttcaccgggg tggtgcccat cctggtcgag ctggacggcg acgtaaacgg ccacaagttc   1860
agcgtgtccg gcgagggcga gggcgatgcc acctacggca agctgaccct gaagttcatc   1920
tgcaccaccg gcaagctgcc cgtgccctgg cccaccctcg tgaccacctt cggctacggc   1980
ctgcagtgct tcgcccgcta ccccgaccac atgaagcagc acgacttctt caagtccgcc   2040
atgcccgaag gctacgtcca ggagcgcacc atcttcttca aggacgacgg caactacaag   2100
acccgcgccg aggtgaagtt cgagggcgac accctggtga accgcatcga gctgaagggc   2160
atcgacttca aggaggacgg caacatcctg gggcacaagc tggagtacaa ctacaacagc   2220
cacaacgtct atatcatggc cgacaagcag aagaacggca tcaaggtgaa cttcaagatc   2280
cgccacaaca tcgaggacgg cagcgtgcag ctcgccgacc actaccagca gaacacccc   2340 atcggcgacg gccccgtgct gctgcccgac aaccactacc tgagctacca gtccgccctg   2400
agcaaagacc ccaacgagaa gcgcgatcac atggtcctgc tggagttcgt gaccgccgcc   2460
gggatcactc tcggcatgga cgagctgtac aagtaaaagc ttgatccggc tgctaacaaa   2520
gcccgaaagg aagctgagtt ggctgctgcc accgctgagc aataactagc ataacccctt   2580
ggggcctcta aacgggtctt gaggggtttt ttgctgaaag gaggaactat atccggatct   2640
ggcgtaatag cgaagaggcc cgcaccgatc gcccttccca acagttgcgc agcctgaatg   2700
gcgaatggga cgcgccctgt agcggcgcat taagcgcggc gggtgtggtg gttacgcgca   2760
gcgtgaccgc tacacttgcc agcgccctag cgcccgctcc tttcgctttc ttcccttcct   2820
ttctcgccac gttcgccggc tttccccgtc aagctctaaa tcggggctc cctttagggt   2880 tccgatttag agctttacgg cacctcgacc gcaaaaaact tgatttgggt gatggttcac   2940
gtagtgggcc atcgccctga tagacggttt ttcgcccttt gacgttggag tccacgttct   3000
ttaatagtgg actcttgttc caaactggaa caacactcaa ccctatcgcg gtctattctt   3060
```

```
ttgatttata agggattttg ccgatttcgg cctattggtt aaaaaatgag ctgatttaac    3120
aaatatttaa cgcgaatttt aacaaaatat taacgtttac aatttcgcct gatgcggtat    3180
tttctcctta cgcatctgtg cggtatttca caccgcatac aggtggcact tttcggggaa    3240
atgtgcgcgg aacccctatt tgtttatttt tctaaataca ttcaaatatg tatccgctca    3300
tgagacaata accctgataa atgcttcaat aatattgaaa aaggaagagt atgagtattc    3360
aacatttccg tgtcgccctt attccctttt ttgcggcatt ttgccttcct gttttgctc    3420 acccagaaac gctggtgaaa gtaaaagatg ctgaagatca gttgggtgca cgagtgggtt    3480
acatcgaact ggatctcaac agcggtaaga tccttgagag ttttcgcccc gaagaacgtt    3540
ttccaatgat gagcactttt aaagttctgc tatgtgatac actattatcc cgtattgacg    3600
ccgggcaaga gcaactcggt cgccgcatac actattctca gaatgacttg gttgagtact    3660
caccagtcac agaaaagcat cttacggatg gcatgacagt aagagaatta tgcagtgctg    3720
ccataaccat gagtgataac actgcggcca acttacttct gacaacgatc ggaggaccga    3780
aggagctaac cgcttttttg cacaacatgg gggatcatgt aactcgcctt gatcgttggg    3840
aaccggagct gaatgaagcc ataccaaacg acgagagtga ccacgatg cctgtagcaa     3900 tgccaacaac gttgcgcaaa ctattaactg gcgaactact tactctagct tcccggcaac    3960
aattaataga ctgaatggag gcggataaag ttgcaggacc acttctgcgc tcggcccttc    4020
cggctggctg gtttattgct gataaatctg gagccggtga gcgtgggtct cgcggtatca    4080
ttgcagcact ggggccagat ggtaagcgct cccgtatcgt agttatctac acgacgggga    4140
gtcaggcaac tatggatgaa cgaaatagac agatcgctga gataggtgcc tcactgatta    4200
agcattggta actgtcagac caagtttact catatatact ttagattgat ttaaaacttc    4260
atttttaatt taaaaggatc taggtgaaga tccttttga taatctcatg accaaaatcc    4320
cttaacgtga gttttcgttc cactgagcgt cagaccccgt agaaaagatc aaaggatctt    4380
cttgagatcc tttttttctg cgcgtaatct gctgcttgca acaaaaaaa ccaccgctac     4440 cagcggtggt ttgtttgccg gatcaagagc taccaactct ttttccgaag gtaactggct    4500
tcagcagagc gcagatacca aatactgtcc ttctagtgta gccgtagtta ggccaccact    4560
tcaagaactc tgtagcaccg cctacatacc tcgctctgct aatcctgtta ccagtggctg    4620
ctgccagtgg cgataagtcg tgtcttaccg ggttggactc aagacgatag ttaccggata    4680
aggcgcagcg gtcgggctga acggggggtt cgtgcacaca gcccagcttg gagcgaacga    4740
cctacaccga actgagatac ctacagcgtg agctatgaga aagcgccacg cttcccgaag    4800
ggagaaaggc ggacaggtat ccggtaagcg gcagggtcgg aacaggagag cgcacgaggg    4860
agcttccagg gggaaacgcc tggtatcttt atagtcctgt cgggtttcgc cacctctgac    4920
ttgagcgtcg atttttgtga tgctcgtcag ggggcggag cctatggaaa aacgccagca    4980
acgcggcctt tttacggttc ctgggctttt gctggccttt tgctcacatg ttctttcctg    5040
cgttatcccc tgattctgtg gataaccgta ttaccgcctt tgagtgagct gataccgctc    5100
gccgcagccg aacgaccgag cgcagcgagt cagtgagcga ggaagcggaa gagcgcccaa    5160
tacgcaaacc gcctctcccc gcgcgttggc cgattcatta atgcag              5206
```

<210> SEQ ID NO 11
<211> LENGTH: 7603
<212> TYPE: DNA
<213> ORGANISM: Artificial Sequence
<220> FEATURE:
<223> OTHER INFORMATION: DNA sequence of pDisplay FLIP-E 600n

```
<400> SEQUENCE: 11
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgacccccgc ccattgacgt caataatgac gtatgttccc atagtaacgc     180
caatagggac tttccattga cgtcaatggg tggactattt acggtaaact gcccacttgg     240
cagtacatca agtgtatcat atgccaagta cgccccctat tgacgtcaat gacggtaaat     300
ggcccgcctg gcattatgcc cagtacatga ccttatggga cttttcctact tggcagtaca    360 tctacgtatt agtcatcgct attaccatgg tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta tataagcaga gctctctggc     600
taactagaga acccactgct tactggctta tcgaaattaa tacgactcac tatagggaga     660
cccaagcttg gtaccgagct cggatccact agtaacggcc gccagtgtgc tggaattcgg     720
cttggggata tccaccatgg agacagacac actcctgcta tgggtactgc tgctctgggt     780
tccaggttcc actggtgact atccatatga tgttccagat tatgctgggg cccagccggc     840
cagatctccc gggatggtga gcaagggcga ggagctgttc accggggtgg tgcccatcct     900
ggtcgagctg gacggcgacg taaacggcca agttcagc gtgtccggcg agggcgaggg      960
cgatgccacc tacggcaagc tgaccctgaa gttcatctgc accaccggca agctgcccgt    1020
gccctggccc accctcgtga ccaccctgac ctggggcgtg cagtgcttca gccgctaccc    1080
cgaccacatg aagcagcacg acttcttcaa gtccgccatg cccgaaggct acgtccagga    1140
gcgcaccatc ttcttcaagg acgacggcaa ctacaagacc cgcgccgagg tgaagttcga    1200
gggcgacacc ctggtgaacc gcatcgagct gaagggcatc gacttcaagg aggacggcaa    1260
catcctgggg cacaagctgg agtacaacta catcagccac aacgtctata tcaccgccga    1320
caagcagaag aacggcatca aggccaactt caagatccgc cacaacatcg aggacggcag    1380
cgtgcagctc gccgaccact accagcagaa cacccccatc ggcgacggcc ccgtgctgct    1440
gcccgacaac cactacctga gcacccagtc cgccctgagc aaagacccca acgagaagcg    1500
cgatcacatg gtcctgctgg agttcgtgac cgccgccggg atcactctcg gcatggacga    1560
gctgtacaag ggtggtaccg gaggcgccgc aggcagcacg ctggacaaaa tcgccaaaaa    1620
cggtgtgatt gtcgtcggtc accgtgaatc ttcagtgcct ttctcttatt acgacaatca    1680
gcaaaaagtg gtgggttact cgcaggatta ctccaacgcc attgttgaag cagtgaaaaa    1740
gaaactcaac aaaccggact tgcaggtaaa actgattccg attacctcac aaaaccgtat    1800
tccactgctg caaaacggca cttttcgatt tgaatgtggt tctaccacca acaacgtcga    1860
acgccaaaaa caggcggctt tctctgacac tatttttcgtg gtcggtacgc gcctgttgac    1920
caaaaagggt ggcgatatca aagattttgc caacctgaaa gacaaagccg tagtcgtcac    1980
ttccggcact acctctgaag ttttgctcaa caaactgaat gaagagcaaa aaatgaatat    2040
gcgcatcatc agcgccaaag atcacggtga ctctttccgc accctggaaa gcggtcgtgc    2100
cgttgccttt atgatggatg acgctctgct ggccggtgaa cgtgcgaaag cgaagaaacc    2160
agacaactgg gaaatcgtcg gcaagccgca gtctcaggag gcctacggtt gtatgttgcg    2220
taaagatgat ccgcagttca aaaagctgat ggatgacacc atcgctcagg tgcagacctc    2280
cggtgaagcg gaaaaatggt ttgataagtg gttcaaaaat ccaattccgc cgaaaaacct    2340
```

```
gaacatgaat tcgaactgt cagacgaaat gaaagcactg ttcaaagaac cgaatgacaa    2400
ggcactgaac ggcgccggta ccggtggaat ggtgagcaag ggcgaggagc tgttcaccgg    2460
ggtggtgccc atcctggtcg agctggacgg cgacgtaaac ggccacaagt tcagcgtgtc    2520
cggcgagggc gagggcgatg ccacctacgg caagctgacc ctgaagttca tctgcaccac    2580
cggcaagctg cccgtgccct ggcccaccct cgtgaccacc ttcggctacg gcctgcagtg    2640
cttcgcccgc taccccgacc acatgaagca gcacgacttc ttcaagtccg ccatgcccga    2700
aggctacgtc caggagcgca ccatcttctt caaggacgac ggcaactaca agacccgcgc    2760
cgaggtgaag ttcgagggcg acaccctggt gaaccgcatc gagctgaagg gcatcgactt    2820
caaggaggac ggcaacatcc tggggcacaa gctggagtac aactacaaca gccacaacgt    2880
ctatatcatg gccgacaagc agaagaacgg catcaaggtg aacttcaaga tccgccacaa    2940
catcgaggac ggcagcgtgc agctcgccga ccactaccag cagaacaccc ccatcggcga    3000
cggccccgtg ctgctgcccg acaaccacta cctgagctac cagtccgccc tgagcaaaga    3060
ccccaacgag aagcgcgatc acatggtcct gctggagttc gtgaccgccg ccgggatcac    3120
tctcggcatg gacgagctgt acaaggtcga cgaacaaaaa ctcatctcag aagaggatct    3180
gaatgctgtg ggccaggaca cgcaggaggt catcgtggtg ccacactcct gccctttaa     3240 ggtggtggtg atctcagcca tcctggccct ggtggtgctc accatcatct cccttatcat    3300
cctcatcatg ctttggcaga agaagccacg ttaggcggcc gctcgagatc agcctcgact    3360
gtgccttcta gttgccagcc atctgttgtt tgccccctccc ccgtgccttc cttgaccctg    3420
gaaggtgcca ctcccactgt cctttcctaa taaaatgagg aaattgcatc gcattgtctg    3480
agtaggtgtc attctattct ggggggtggg gtggggcagg acagcaaggg ggaggattgg    3540
gaagacaata gcaggcatgc tggggatgcg gtgggctcta tggcttctga ggcggaaaga    3600
accagtggcg gtaatacggt tatccacaga atcaggggat aacgcaggaa agaacatgtg    3660
agcaaaaggc cagcaaaagg ccaggaaccg taaaaaggcc gcgttgctgg cgttttttcca    3720 taggctccgc cccctgacg agcatcacaa aaatcgacgc tcaagtcaga ggtggcgaaa    3780
cccgacagga ctataaagat accaggcgtt tcccctgga agctccctcg tgcgctctcc     3840
tgttccgacc ctgccgctta ccggatacct gtccgccttt ctcccttcgg gaagcgtggc    3900
gctttctcat agctcacgct gtaggtatct cagttcggtg taggtcgttc gctccaagct    3960
gggctgtgtg cacgaacccc ccgttcagcc cgaccgctgc gccttatccg gtaactatcg    4020
tcttgagtcc aacccggtaa gacacgactt atcgccactg gcagcagcca ctggtaacag    4080
gattagcaga gcgaggtatg taggcggtgc tacagagttc ttgaagtggt ggcctaacta    4140
cggctacact agaaggacag tatttggtat ctgcgctctg ctgaagccag ttaccttcgg    4200
aaaaagagtt ggtagctctt gatccggcaa acaaaccacc gctggtagcg gtggtttttt    4260
tgtttgcaag cagcagatta cgcgcagaaa aaaaggatct caagaagatc ctttgatctt    4320
ttctacgggg tctgacgctc agtggaacga aaactcacgt taagggattt tggtcatgag    4380
attatcaaaa aggatcttca cctagatcct tttaaattaa aaatgaagtt ttaaatcaat    4440
ctaaagtata tatgagtaac ctgaggctat ggcagggcct gccgccccga cgttggctgc    4500
gagccctggg ccttcacccg aacttggggg gtggggtggg gaaaaggaag aaacgcgggc    4560
gtattggccc caatggggtc tcggtggggt atcgacagag tgccagccct gggaccgaac    4620
cccgcgttta tgaacaaacg acccaacacc gtgcgtttta ttctgtcttt ttattgccgt    4680
catagcgcgg gttccttccg gtattgtctc cttccgtgtt tcagttagcc tcccccctagg    4740
```

```
gtgggcgaag aactccagca tgagatcccc gcgctggagg atcatccagc cggcgtcccg    4800
gaaaacgatt ccgaagccca acctttcata gaaggcggcg gtggaatcga aatctcgtga    4860
tggcaggttg ggcgtcgctt ggtcggtcat ttcgaacccc agagtcccgc tcagaagaac    4920
tcgtcaagaa ggcgatagaa ggcgatgcgc tgcgaatcgg gagcggcgat accgtaaagc    4980
acgaggaagc ggtcagccca ttcgccgcca agctcttcag caatatcacg ggtagccaac    5040
gctatgtcct gatagcggtc cgccacaccc agccggccac agtcgatgaa tccagaaaag    5100
cggccatttt ccaccatgat attcggcaag caggcatcgc catgggtcac gacgagatcc    5160
tcgccgtcgg catgctcgc cttgagcctg gcgaacagtt cggctggcgc gagcccctga    5220
tgctcttgat catcctgatc gacaagaccg gcttccatcc gagtacgtgc tcgctcgatg    5280
cgatgtttcg cttggtggtc gaatgggcag gtagccggat caagcgtatg cagccgccgc    5340
attgcatcag ccatgatgga tactttctcg gcaggagcaa ggtgagatga caggagatcc    5400
tgccccggca cttcgcccaa tagcagccag tcccttcccg cttcagtgac aacgtcgagc    5460
acagctgcgc aaggaacgcc cgtcgtggcc agccacgata ccgcgctgc ctcgtcttgc    5520 agttcattca gggcaccgga caggtcggtc ttgacaaaaa gaaccgggcg cccctgcgct    5580
gacagccgga acacggcggc atcagagcag ccgattgtct gttgtgccca gtcatagccg    5640
aatagcctct ccacccaagc ggccggagaa cctgcgtgca atccatcttg ttcaatcatg    5700
cgaaacgatc ctcatcctgt ctcttgatcg atctttgcaa aagcctaggc ctccaaaaaa    5760
gcctcctcac tacttctgga atagctcaga ggccgaggag gcggcctcgg cctctgcata    5820
aataaaaaaa attagtcagc catggggcgg agaatgggcg gaactgggcg gagttagggg    5880
cgggatgggc ggagttaggg gcgggactat ggttgctgac taattgagat gcatgctttg    5940
catacttctg cctgctgggg agcctgggga cttttccacac ctggttgctg actaattgag    6000
atgcatgctt tgcatacttc tgcctgctgg ggagcctggg gacttccac accctaactg    6060 acacacattc cacagctggt tctttccgcc tcaggactct tcctttttca ataaatcaat    6120
ctaaagtata tatgagtaaa cttggtctga cagttaccaa tgcttaatca gtgaggcacc    6180
tatctcagcg atctgtctat ttcgttcatc catagttgcc tgactccccg tcgtgtagat    6240
aactacgata cgggagggct taccatctgg ccccagtgct gcaatgatac cgcgagaccc    6300
acgctcaccg gctccagatt tatcagcaat aaaccagcca gccggaaggg ccgagcgcag    6360
aagtggtcct gcaactttat ccgcctccat ccagtctatt aattgttgcc gggaagctag    6420
agtaagtagt tcgccagtta atagtttgcg caacgttgtt gccattgcta caggcatcgt    6480
ggtgtcacgc tcgtcgtttg gtatggcttc attcagctcc ggttcccaac gatcaaggcg    6540
agttacatga tcccccatgt tgtgcaaaaa agcggttagc tccttcggtc ctccgatcgt    6600
tgtcagaagt aagttggccg cagtgttatc actcatggtt atggcagcac tgcataattc    6660
tcttactgtc atgccatccg taagatgctt ttctgtgact ggtgagtact caaccaagtc    6720
attctgagaa tagtgtatgc ggcgaccgag ttgctcttgc ccggcgtcaa tacgggataa    6780
taccgcgcca catagcagaa ctttaaaagt gctcatcatt ggaaaacgtt cttcggggcg    6840
aaaactctca aggatcttac cgctgttgag atccagttcg atgtaaccca ctcgtgcacc    6900
caactgatct tcagcatctt ttactttcac cagcgtttct gggtgagcaa aaacaggaag    6960
gcaaaatgcc gcaaaaaagg gaataagggc gacacggaaa tgttgaatac tcatactctt    7020 ccttttttcaa tattattgaa gcatttatca gggttattgt ctcatgagcg gatacatatt    7080
tgaatgtatt tagaaaaata aacaaatagg ggttccgcgc acatttcccc gaaaagtgcc    7140
```

```
acctgacgcg ccctgtagcg gcgcattaag cgcggcgggt gtggtggtta cgcgcagcgt    7200
gaccgctaca cttgccagcg ccctagcgcc cgctcctttc gctttcttcc cttcctttct    7260
cgccacgttc gccggctttc cccgtcaagc tctaaatcgg gggctccctt tagggttccg    7320
atttagtgct ttacggcacc tcgaccccaa aaaacttgat tagggtgatg gttcacgtag    7380
tgggccatcg ccctgataga cggttttttcg ccctttgacg ttggagtcca cgttctttaa    7440
tagtggactc ttgttccaaa ctggaacaac actcaaccct atctcggtct attcttttga    7500
tttataaggg attttgccga tttcggccta ttggttaaaa aatgagctga tttaacaaaa    7560
atttaacgcg aattttaaca aaatattaac gcttacaatt tac                      7603

<210> SEQ ID NO 12
<211> LENGTH: 7603
<212> TYPE: DNA
<213> ORGANISM: Artificial Sequence
<220> FEATURE:
<223> OTHER INFORMATION: DNA sequence of pDisplay FLIP-E 10u

<400> SEQUENCE: 12
gcgcgcgttg acattgatta ttgactagtt attaatagta atcaattacg gggtcattag     60
ttcatagccc atatatggag ttccgcgtta cataacttac ggtaaatggc ccgcctggct    120
gaccgcccaa cgaccccgc ccattgacgt caataatgac gtatgttccc atagtaacgc    180
caatagggac tttccattga cgtcaatggg tggactattt acggtaaact gcccacttgg    240
cagtacatca agtgtatcat atgccaagta cgccccctat tgacgtcaat gacggtaaat    300
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta tataagcaga gctctctggc    600
taactagaga acccactgct tactggctta tcgaaattaa tacgactcac tatagggaga    660
cccaagcttg gtaccgagct cggatccact agtaacggcc gccagtgtgc tggaattcgg    720
cttggggata tccaccatgg agacagacac actcctgcta tgggtactgc tgctctgggt    780
tccaggttcc actggtgact atccatatga tgttccagat tatgctgggg cccagccggc    840
cagatctccc gggatggtga gcaagggcga ggagctgttc accggggtgg tgcccatcct    900
ggtcgagctg gacggcgacg taaacggcca agttcagc gtgtccggcg agggcgaggg    960
cgatgccacc tacggcaagc tgaccctgaa gttcatctgc accaccggca agctgcccgt   1020
gccctggccc accctcgtga ccaccctgac ctggggcgtg cagtgcttca gccgctaccc   1080
cgaccacatg aagcagcacg acttcttcaa gtccgccatg cccgaaggct acgtccagga   1140
gcgcaccatc ttcttcaagg acgacggcaa ctacaagacc cgcgccgagg tgaagttcga   1200
gggcgacacc ctggtgaacc gcatcgagct gaagggcatc gacttcaagg aggacggcaa   1260
catcctgggg cacaagctgg agtacaacta catcagccac aacgtctata tcaccgccga   1320
caagcagaag aacggcatca aggccaactt caagatccgc cacaacatcg aggacggcag   1380
cgtgcagctc gccgaccact accagcagaa caccccatc ggcgacggcc ccgtgctgct   1440
gcccgacaac cactacctga gcacccagtc cgccctgagc aaagaccca acgagaagcg   1500 cgatcacatg gtcctgctgg agttcgtgac cgccgccggg atcactctcg gcatggacga   1560
gctgtacaag ggtggtaccg gaggcgccgc aggcagcacg ctggacaaaa tcgccaaaaa   1620
```

-continued

```
cggtgtgatt gtcgtcggtc accgtgaatc ttcagtgcct ttctcttatt acgacaatca    1680
gcaaaaagtg gtgggttact cgcaggatta ctccaacgcc attgttgaag cagtgaaaaa    1740
gaaactcaac aaaccggact tgcaggtaaa actgattccg attacctcac aaaaccgtat    1800
tccactgctg caaaacggca ctttcgattt tgaatgtggt tctaccacca acaacgtcga    1860
acgccaaaaa caggcggctt tctctgacac tattttcgtg gtcggtacgc gcctgttgac    1920
caaaaagggt ggcgatatca agattttgc caacctgaaa gacaaagccg tagtcgtcac    1980
ttccggcact acctctgaag ttttgctcaa caaactgaat gaagagcaaa aaatgaatat    2040
gcgcatcatc agcgccaaag atcacggtga ctctttccgc accctggaaa gcggtcgtgc    2100
cgttgccttt atgatggatg accggctgct ggccggtgaa cgtgcgaaag cgaagaaacc    2160
agacaactgg gaaatcgtcg gcaagccgca gtctcaggag gcctacggtt gtatgttgcg    2220
taaagatgat ccgcagttca aaagctgat ggatgacacc atcgctcagg tgcagacctc    2280
cggtgaagcg gaaaatggt ttgataagtg gttcaaaaat ccaattccgc cgaaaaacct    2340
gaacatgaat ttcgaactgt cagacgaaat gaaagcactg ttcaaagaac cgaatgacaa    2400
ggcactgaac ggcgccggta ccggtggaat ggtgagcaag ggcgaggagc tgttcaccgg    2460
ggtggtgccc atcctggtcg agctggacgg cgacgtaaac ggccacaagt tcagcgtgtc    2520
cggcgagggc gagggcgatg ccacctacgg caagctgacc ctgaagttca tctgcaccac    2580
cggcaagctg cccgtgccct ggcccaccct cgtgaccacc ttcggctacg gcctgcagtg    2640
cttcgcccgc taccccgacc acatgaagca gcacgacttc ttcaagtccg ccatgcccga    2700
aggctacgtc caggagcgca ccatcttctt caaggacgac ggcaactaca agacccgcgc    2760
cgaggtgaag ttcgagggcg acaccctggt gaaccgcatc gagctgaagg gcatcgactt    2820
caaggaggac ggcaacatcc tggggcacaa gctggagtac aactacaaca gccacaacgt    2880
ctatatcatg gccgacaagc agaagaacgg catcaaggtg aacttcaaga tccgccacaa    2940
catcgaggac ggcagcgtgc agctcgccga ccactaccag cagaacaccc ccatcggcga    3000
cggccccgtg ctgctgcccg acaaccacta cctgagctac cagtccgccc tgagcaaaga    3060
ccccaacgag aagcgcgatc acatggtcct gctggagttc gtgaccgccg ccgggatcac    3120
tctcggcatg gacgagctgt acaaggtcga cgaacaaaaa ctcatctcag aagaggatct    3180
gaatgctgtg ggccaggaca cgcaggaggt catcgtggtg ccacactcct tgcccttta    3240 ggtggtggtg atctcagcca tcctggccct ggtggtgctc accatcatct cccttatcat    3300
cctcatcatg ctttggcaga agaagccacg ttaggcggcc gctcgagatc agcctcgact    3360
gtgccttcta gttgccagcc atctgttgtt tgccctccc ccgtgccttc cttgaccctg    3420
gaaggtgcca ctcccactgt cctttcctaa taaaatgagg aaattgcatc gcattgtctg    3480
agtaggtgtc attctattct ggggggtggg gtggggcagg acagcaaggg ggaggattgg    3540
gaagacaata gcaggcatgc tggggatgcg gtgggctcta tggcttctga gcggaaaga    3600 accagtggcg gtaatacggt tatccacaga atcaggggat aacgcaggaa agaacatgtg    3660
agcaaaaggc cagcaaaagg ccaggaaccg taaaaaggcc gcgttgctgg cgttttccca    3720
taggctccgc cccctgacg agcatcacaa aaatcgacgc tcaagtcaga ggtggcgaaa    3780
cccgacagga ctataaagat accaggcgtt tccccctgga agctccctcg tgcgctctcc    3840
tgttccgacc ctgccgctta ccggatacct gtccgccttt ctcccttcgg aagcgtggc    3900 gctttctcat agctcacgct gtaggtatct cagttcggtg taggtcgttc gctccaagct    3960
gggctgtgtg cacgaacccc ccgttcagcc cgaccgctgc gccttatccg gtaactatcg    4020
```

-continued

```
tcttgagtcc aacccggtaa gacacgactt atcgccactg gcagcagcca ctggtaacag   4080
gattagcaga gcgaggtatg taggcggtgc tacagagttc ttgaagtggt ggcctaacta   4140
cggctacact agaaggacag tatttggtat ctgcgctctg ctgaagccag ttaccttcgg   4200
aaaaagagtt ggtagctctt gatccggcaa acaaaccacc gctggtagcg tggttttttt   4260
tgtttgcaag cagcagatta cgcgcagaaa aaaaggatct caagaagatc ctttgatctt   4320
ttctacgggg tctgacgctc agtggaacga aaactcacgt taagggattt tggtcatgag   4380
attatcaaaa aggatcttca cctagatcct tttaaattaa aaatgaagtt ttaaatcaat   4440
ctaaagtata tatgagtaac ctgaggctat ggcagggcct gccgccccga cgttggctgc   4500
gagccctggg ccttcacccg aacttggggg gtgggtggg gaaaaggaag aaacgcgggc   4560
gtattggccc caatgggggtc tcggtggggt atcgacagag tgccagccct gggaccgaac   4620
cccgcgttta tgaacaaacg acccaacacc gtgcgtttta ttctgtcttt ttattgccgt   4680
catagcgcgg gttccttccg gtattgtctc cttccgtgtt tcagttagcc tcccccctagg   4740
gtgggcgaag aactccagca tgagatcccc gcgctggagg atcatccagc cggcgtcccg   4800
gaaaacgatt ccgaagccca accttttcata gaaggcggcg gtggaatcga aatctcgtga   4860
tggcaggttg ggcgtcgctt ggtcggtcat ttcgaacccc agagtccgcg tcagaagaac   4920
tcgtcaagaa ggcgatagaa ggcgatgcgc tgcgaatcgg gagcggcgat accgtaaagc   4980
acgaggaagc ggtcagccca ttcgccgcca agctcttcag caatatcacg ggtagccaac   5040
gctatgtcct gatagcggtc cgccacaccc agccggccac agtcgatgaa tccagaaaag   5100
cggccatttt ccaccatgat attcggcaag caggcatcgc catgggtcac gacgagatcc   5160
tcgccgtcgg gcatgctcgc cttgagcctg gcgaacagtt cggctggcgc gagccctga   5220
tgctcttgat catcctgatc gacaagaccg gcttccatcc gagtacgtgc tcgctcgatg   5280
cgatgtttcg cttggtggtc gaatgggcag gtagccggat caagcgtatg cagccgccgc   5340
attgcatcag ccatgatgga tactttctcg gcaggagcaa ggtgagatga caggagatcc   5400
tgccccggca cttcgcccaa tagcagccag tcccttcccg cttcagtgac aacgtcgagc   5460
acagctgcgc aaggaacgcc cgtcgtggcc agccacgata gccgcgctgc ctcgtcttgc   5520
agttcattca gggcaccgga caggtcggtc ttgacaaaaa gaaccgggcg cccctgcgct   5580
gacagccgga acacggcggc atcagagcag ccgattgtct gttgtgccca gtcatagccg   5640
aatagcctct ccacccaagc ggccggagaa cctgcgtgca atccatcttg ttcaatcatg   5700
cgaaacgatc ctcatcctgt ctcttgatcg atctttgcaa aagcctaggc ctccaaaaaa   5760
gcctcctcac tacttctgga atagctcaga ggccgaggag gcggcctcgg cctctgcata   5820
aataaaaaaa attagtcagc catggggcgg agaatgggcg gaactgggcg gagttagggg   5880
cgggatgggc ggagttaggg gcgggactat ggttgctgac taattgagat gcatgctttg   5940
catacttctg cctgctgggg agcctgggga cttttccacac ctggttgctg actaattgag   6000
atgcatgctt tgcatacttc tgcctgctgg ggagcctggg gactttccac accctaactg   6060
acacacattc cacagctggt tcttttccgcc tcaggactct tccttttttca ataaatcaat   6120
ctaaagtata tatgagtaaa cttggtctga cagttaccaa tgcttaatca gtgaggcacc   6180
tatctcagcg atctgtctat ttcgttcatc catagttgcc tgactcccccg tcgtgtagat   6240
aactacgata cgggagggct taccatctgg ccccagtgct gcaatgatac cgcgagaccc   6300
acgctcaccg gctccagatt tatcagcaat aaaccagcca gccggaaggg ccgagcgcag   6360
aagtggtcct gcaactttat ccgcctccat ccagtctatt aattgttgcc gggaagctag   6420
```

-continued

```
agtaagtagt tcgccagtta atagtttgcg caacgttgtt gccattgcta caggcatcgt   6480
ggtgtcacgc tcgtcgtttg gtatggcttc attcagctcc ggttcccaac gatcaaggcg   6540
agttacatga tcccccatgt tgtgcaaaaa agcggttagc tccttcggtc ctccgatcgt   6600
tgtcagaagt aagttggccg cagtgttatc actcatggtt atggcagcac tgcataattc   6660
tcttactgtc atgccatccg taagatgctt ttctgtgact ggtgagtact caaccaagtc   6720
attctgagaa tagtgtatgc ggcgaccgag ttgctcttgc ccggcgtcaa tacgggataa   6780
taccgcgcca catagcagaa ctttaaaagt gctcatcatt ggaaaacgtt cttcggggcg   6840
aaaactctca aggatcttac cgctgttgag atccagttcg atgtaaccca ctcgtgcacc   6900
caactgatct tcagcatctt ttactttcac cagcgtttct gggtgagcaa aacaggaag    6960 gcaaaatgcc gcaaaaaagg gaataagggc gacacggaaa tgttgaatac tcatactctt   7020
cctttttcaa tattattgaa gcatttatca gggttattgt ctcatgagcg gatacatatt   7080
tgaatgtatt tagaaaaata acaaataggg gttccgcgc  acatttcccc gaaaagtgcc   7140
acctgacgcg ccctgtagcg gcgcattaag cgcggcgggt gtggtggtta cgcgcagcgt   7200
gaccgctaca cttgccagcg ccctagcgcc cgctcctttc gctttcttcc cttcctttct   7260
cgccacgttc gccggctttc cccgtcaagc tctaaatcgg gggctccctt tagggttccg   7320
atttagtgct ttacggcacc tcgaccccaa aaaacttgat tagggtgatg gttcacgtag   7380
tgggccatcg ccctgataga cggttttttcg ccctttgacg ttggagtcca cgttctttaa   7440
tagtggactc ttgttccaaa ctggaacaac actcaaccct atctcggtct attcttttga   7500
tttataaggg attttgccga tttcggccta ttggttaaaa aatgagctga tttaacaaaa   7560
atttaacgcg aattttaaca aaatattaac gcttacaatt tac                     7603
```

<210> SEQ ID NO 13
<211> LENGTH: 799
<212> TYPE: PRT
<213> ORGANISM: Artificial Sequence
<220> FEATURE:
<223> OTHER INFORMATION: Amino acid sequence of FLIP-E 600n (expressed
as 6xHis fusion in pRSET FLIP-E 600n)

<400> SEQUENCE: 13

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Met Val Ser Lys Gly Glu Glu Leu Phe Thr Gly Val Val
        35                  40                  45

Pro Ile Leu Val Glu Leu Asp Gly Asp Val Asn Gly His Lys Phe Ser
    50                  55                  60

Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Trp Gly Val Gln Cys Phe Ser Arg Tyr Pro Asp
            100                 105                 110

His Met Lys Gln His Asp Phe Phe Lys Ser Ala Met Pro Glu Gly Tyr
        115                 120                 125

Val Gln Glu Arg Thr Ile Phe Phe Lys Asp Asp Gly Asn Tyr Lys Thr
    130                 135                 140

Arg Ala Glu Val Lys Phe Glu Gly Asp Thr Leu Val Asn Arg Ile Glu
```

```
            145                 150                 155                 160
Leu Lys Gly Ile Asp Phe Lys Glu Asp Gly Asn Ile Leu Gly His Lys
            165                 170                 175

Leu Glu Tyr Asn Tyr Ile Ser His Asn Val Tyr Ile Thr Ala Asp Lys
            180                 185                 190

Gln Lys Asn Gly Ile Lys Ala Asn Phe Lys Ile Arg His Asn Ile Glu
            195                 200                 205

Asp Gly Ser Val Gln Leu Ala Asp His Tyr Gln Gln Asn Thr Pro Ile
            210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
            245                 250                 255

Leu Glu Phe Val Thr Ala Ala Gly Ile Thr Leu Gly Met Asp Glu Leu
            260                 265                 270

Tyr Lys Gly Gly Thr Gly Gly Ala Ala Gly Ser Thr Leu Asp Lys Ile
            275                 280                 285

Ala Lys Asn Gly Val Ile Val Gly His Arg Glu Ser Ser Val Pro
            290                 295                 300

Phe Ser Tyr Tyr Asp Asn Gln Gln Lys Val Val Gly Tyr Ser Gln Asp
305                 310                 315                 320

Tyr Ser Asn Ala Ile Val Glu Ala Val Lys Lys Leu Asn Lys Pro
            325                 330                 335

Asp Leu Gln Val Lys Leu Ile Pro Ile Thr Ser Gln Asn Arg Ile Pro
            340                 345                 350

Leu Leu Gln Asn Gly Thr Phe Asp Phe Glu Cys Gly Ser Thr Thr Asn
            355                 360                 365

Asn Val Glu Arg Gln Lys Gln Ala Ala Phe Ser Asp Thr Ile Phe Val
            370                 375                 380

Val Gly Thr Arg Leu Leu Thr Lys Lys Gly Gly Asp Ile Lys Asp Phe
385                 390                 395                 400

Ala Asn Leu Lys Asp Lys Ala Val Val Thr Ser Gly Thr Thr Ser
            405                 410                 415

Glu Val Leu Leu Asn Lys Leu Asn Glu Glu Gln Lys Met Asn Met Arg
            420                 425                 430

Ile Ile Ser Ala Lys Asp His Gly Asp Ser Phe Arg Thr Leu Glu Ser
            435                 440                 445

Gly Arg Ala Val Ala Phe Met Met Asp Asp Ala Leu Leu Ala Gly Glu
450                 455                 460

Arg Ala Lys Ala Lys Lys Pro Asp Asn Trp Glu Ile Val Gly Lys Pro
465                 470                 475                 480

Gln Ser Gln Glu Ala Tyr Gly Cys Met Leu Arg Lys Asp Asp Pro Gln
            485                 490                 495

Phe Lys Lys Leu Met Asp Asp Thr Ile Ala Gln Val Gln Thr Ser Gly
            500                 505                 510

Glu Ala Glu Lys Trp Phe Asp Lys Trp Phe Lys Asn Pro Ile Pro Pro
            515                 520                 525

Lys Asn Leu Asn Met Asn Phe Glu Leu Ser Asp Glu Met Lys Ala Leu
            530                 535                 540

Phe Lys Glu Pro Asn Asp Lys Ala Leu Asn Gly Ala Thr Gly Gly
545                 550                 555                 560

Met Val Ser Lys Gly Glu Glu Leu Phe Thr Gly Val Val Pro Ile Leu
            565                 570                 575
```

Val Glu Leu Asp Gly Asp Val Asn Gly His Lys Phe Ser Val Ser Gly
            580                 585                 590

Glu Gly Glu Gly Asp Ala Thr Tyr Gly Lys Leu Thr Leu Lys Phe Ile
        595                 600                 605

Cys Thr Thr Gly Lys Leu Pro Val Pro Trp Pro Thr Leu Val Thr Thr
610                 615                 620

Phe Gly Tyr Gly Leu Gln Cys Phe Ala Arg Tyr Pro Asp His Met Lys
625                 630                 635                 640

Gln His Asp Phe Phe Lys Ser Ala Met Pro Glu Gly Tyr Val Gln Glu
            645                 650                 655

Arg Thr Ile Phe Phe Lys Asp Asp Gly Asn Tyr Lys Thr Arg Ala Glu
            660                 665                 670

Val Lys Phe Glu Gly Asp Thr Leu Val Asn Arg Ile Glu Leu Lys Gly
        675                 680                 685

Ile Asp Phe Lys Glu Asp Gly Asn Ile Leu Gly His Lys Leu Glu Tyr
        690                 695                 700

Asn Tyr Asn Ser His Asn Val Tyr Ile Met Ala Asp Lys Gln Lys Asn
705                 710                 715                 720

Gly Ile Lys Val Asn Phe Lys Ile Arg His Asn Ile Glu Asp Gly Ser
                725                 730                 735

Val Gln Leu Ala Asp His Tyr Gln Gln Asn Thr Pro Ile Gly Asp Gly
            740                 745                 750

Pro Val Leu Leu Pro Asp Asn His Tyr Leu Ser Tyr Gln Ser Ala Leu
        755                 760                 765

Ser Lys Asp Pro Asn Glu Lys Arg Asp His Met Val Leu Leu Glu Phe
770                 775                 780

Val Thr Ala Ala Gly Ile Thr Leu Gly Met Asp Glu Leu Tyr Lys
785                 790                 795

<210> SEQ ID NO 14
<211> LENGTH: 764
<212> TYPE: PRT
<213> ORGANISM: Artificial Sequence
<220> FEATURE:
<223> OTHER INFORMATION: Amino acid sequence of FLIP-E 10u (expressed as
      6xHis fusion in pRSET FLIP-E 10u)

<400> SEQUENCE: 14

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
        100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
    130                 135                 140

-continued

```
Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Gly Thr Gly Gly Ala Ala Gly Ser Thr Leu Asp Lys Ile Ala Lys Asn
                245                 250                 255

Gly Val Ile Val Val Gly His Arg Glu Ser Ser Val Pro Phe Ser Tyr
            260                 265                 270

Tyr Asp Asn Gln Gln Lys Val Gly Tyr Ser Gln Asp Tyr Ser Asn
        275                 280                 285

Ala Ile Val Glu Ala Val Lys Lys Leu Asn Lys Pro Asp Leu Gln
    290                 295                 300

Val Lys Leu Ile Pro Ile Thr Ser Gln Asn Arg Ile Pro Leu Leu Gln
305                 310                 315                 320

Asn Gly Thr Phe Asp Phe Glu Cys Gly Ser Thr Thr Asn Asn Val Glu
                325                 330                 335

Arg Gln Lys Gln Ala Ala Phe Ser Asp Thr Ile Phe Val Val Gly Thr
            340                 345                 350

Arg Leu Leu Thr Lys Lys Gly Gly Asp Ile Lys Asp Phe Ala Asn Leu
        355                 360                 365

Lys Asp Lys Ala Val Val Val Thr Ser Gly Thr Thr Ser Glu Val Leu
    370                 375                 380

Leu Asn Lys Leu Asn Glu Glu Gln Lys Met Asn Met Arg Ile Ile Ser
385                 390                 395                 400

Ala Lys Asp His Gly Asp Ser Phe Arg Thr Leu Glu Ser Gly Arg Ala
                405                 410                 415

Val Ala Phe Met Met Asp Asp Arg Leu Leu Ala Gly Glu Arg Ala Lys
            420                 425                 430

Ala Lys Lys Pro Asp Asn Trp Glu Ile Val Gly Lys Pro Gln Ser Gln
        435                 440                 445

Glu Ala Tyr Gly Cys Met Leu Arg Lys Asp Asp Pro Gln Phe Lys Lys
    450                 455                 460

Leu Met Asp Asp Thr Ile Ala Gln Val Gln Thr Ser Gly Glu Ala Glu
465                 470                 475                 480

Lys Trp Phe Asp Lys Trp Phe Lys Asn Pro Ile Pro Pro Lys Asn Leu
                485                 490                 495

Asn Met Asn Phe Glu Leu Ser Asp Glu Met Lys Ala Leu Phe Lys Glu
            500                 505                 510

Pro Asn Asp Lys Ala Leu Asn Gly Ala Gly Thr Gly Gly Met Val Ser
        515                 520                 525

Lys Gly Glu Glu Leu Phe Thr Gly Val Val Pro Ile Leu Val Glu Leu
    530                 535                 540

Asp Gly Asp Val Asn Gly His Lys Phe Ser Val Ser Gly Glu Gly Glu
545                 550                 555                 560

Gly Asp Ala Thr Tyr Gly Lys Leu Thr Leu Lys Phe Ile Cys Thr Thr
                565                 570                 575
```

```
Gly Lys Leu Pro Val Pro Trp Pro Thr Leu Val Thr Thr Phe Gly Tyr
            580                 585                 590
Gly Leu Gln Cys Phe Ala Arg Tyr Pro Asp His Met Lys Gln His Asp
        595                 600                 605
Phe Phe Lys Ser Ala Met Pro Glu Gly Tyr Val Gln Glu Arg Thr Ile
    610                 615                 620
Phe Phe Lys Asp Asp Gly Asn Tyr Lys Thr Arg Ala Glu Val Lys Phe
625                 630                 635                 640
Glu Gly Asp Thr Leu Val Asn Arg Ile Glu Leu Lys Gly Ile Asp Phe
                645                 650                 655
Lys Glu Asp Gly Asn Ile Leu Gly His Lys Leu Glu Tyr Asn Tyr Asn
            660                 665                 670
Ser His Asn Val Tyr Ile Met Ala Asp Lys Gln Lys Asn Gly Ile Lys
        675                 680                 685
Val Asn Phe Lys Ile Arg His Asn Ile Glu Asp Gly Ser Val Gln Leu
    690                 695                 700
Ala Asp His Tyr Gln Gln Asn Thr Pro Ile Gly Asp Gly Pro Val Leu
705                 710                 715                 720
Leu Pro Asp Asn His Tyr Leu Ser Tyr Gln Ser Ala Leu Ser Lys Asp
                725                 730                 735
Pro Asn Glu Lys Arg Asp His Met Val Leu Leu Glu Phe Val Thr Ala
            740                 745                 750
Ala Gly Ile Thr Leu Gly Met Asp Glu Leu Tyr Lys
        755                 760

<210> SEQ ID NO 15
<211> LENGTH: 2496
<212> TYPE: DNA
<213> ORGANISM: Artificial Sequence
<220> FEATURE:
<223> OTHER INFORMATION: FLIP-mglBF16A-Y12S-CFP-D13R-YFP Vector
<220> FEATURE:
<221> NAME/KEY: CDS
<222> LOCATION: (1)..(2496)

<400> SEQUENCE: 15 atg cgg ggt tct cat cat cat cat cat cat ggt atg gct agc atg act      48
Met Arg Gly Ser His His His His His His Gly Met Ala Ser Met Thr
1               5                   10                  15 ggt gga cag caa atg ggt cgg gat ctg tac gac gat gac gat aag gat      96
Gly Gly Gln Gln Met Gly Arg Asp Leu Tyr Asp Asp Asp Asp Lys Asp
            20                  25                  30 ccg ggc cgc gct gat act cgc att ggt gta aca atc tat aag tcg gct     144
Pro Gly Arg Ala Asp Thr Arg Ile Gly Val Thr Ile Tyr Lys Ser Ala
        35                  40                  45 ggt atg gtg agc aag ggc gag gag ctg ttc acc ggg gtg gtg ccc atc     192
Gly Met Val Ser Lys Gly Glu Glu Leu Phe Thr Gly Val Val Pro Ile
    50                  55                  60 ctg gtc gag ctg gac ggc gac gta aac ggc cac aag ttc agc gtg tcc     240
Leu Val Glu Leu Asp Gly Asp Val Asn Gly His Lys Phe Ser Val Ser
65                  70                  75                  80 ggc gag ggc gag ggc gat gcc acc tac ggc aag ctg acc ctg aag ttc     288
Gly Glu Gly Glu Gly Asp Ala Thr Tyr Gly Lys Leu Thr Leu Lys Phe
                85                  90                  95 atc tgc acc acc ggc aag ctg ccc gtg ccc tgg ccc acc ctc gtg acc     336
Ile Cys Thr Thr Gly Lys Leu Pro Val Pro Trp Pro Thr Leu Val Thr
            100                 105                 110 acc ctg acc tgg ggc gtg cag tgc ttc agc cgc tac ccc gac cac atg     384
Thr Leu Thr Trp Gly Val Gln Cys Phe Ser Arg Tyr Pro Asp His Met
```

```
              115                 120                 125
aag cag cac gac ttc ttc aag tcc gcc atg ccc gaa ggc tac gtc cag    432
Lys Gln His Asp Phe Phe Lys Ser Ala Met Pro Glu Gly Tyr Val Gln
    130                 135                 140 gag cgc acc atc ttc ttc aag gac gac ggc aac tac aag acc cgc gcc    480
Glu Arg Thr Ile Phe Phe Lys Asp Asp Gly Asn Tyr Lys Thr Arg Ala
145                 150                 155                 160 gag gtg aag ttc gag ggc gac acc ctg gtg aac cgc atc gag ctg aag    528
Glu Val Lys Phe Glu Gly Asp Thr Leu Val Asn Arg Ile Glu Leu Lys
                165                 170                 175 ggc atc gac ttc aag gag gac ggc aac atc ctg ggg cac aag ctg gag    576
Gly Ile Asp Phe Lys Glu Asp Gly Asn Ile Leu Gly His Lys Leu Glu
            180                 185                 190 tac aac tac atc agc cac aac gtc tat atc acc gcc gac aag cag aag    624
Tyr Asn Tyr Ile Ser His Asn Val Tyr Ile Thr Ala Asp Lys Gln Lys
        195                 200                 205 aac ggc atc aag gcc aac ttc aag atc cgc cac aac atc gag gac ggc    672
Asn Gly Ile Lys Ala Asn Phe Lys Ile Arg His Asn Ile Glu Asp Gly
    210                 215                 220 agc gtg cag ctc gcc gac cac tac cag cag aac acc ccc atc ggc gac    720
Ser Val Gln Leu Ala Asp His Tyr Gln Gln Asn Thr Pro Ile Gly Asp
225                 230                 235                 240 ggc ccc gtg ctg ctg ccc gac aac cac tac ctg agc acc cag tcc gcc    768
Gly Pro Val Leu Leu Pro Asp Asn His Tyr Leu Ser Thr Gln Ser Ala
                245                 250                 255 ctg agc aaa gac ccc aac gag aag cgc gat cac atg gtc ctg ctg gag    816
Leu Ser Lys Asp Pro Asn Glu Lys Arg Asp His Met Val Leu Leu Glu
            260                 265                 270 ttc gtg acc gcc gcc ggg atc act ctc ggc atg gac gag ctg tac ggt    864
Phe Val Thr Ala Ala Gly Ile Thr Leu Gly Met Asp Glu Leu Tyr Gly
        275                 280                 285 agc cga gat aac gcg atg tct gta gtg cgc aag gct att gag caa gat    912
Ser Arg Asp Asn Ala Met Ser Val Val Arg Lys Ala Ile Glu Gln Asp
    290                 295                 300 gcg aaa gcc gcg cca gat gtt cag ctg ctg atg aat gat tct cag aat    960
Ala Lys Ala Ala Pro Asp Val Gln Leu Leu Met Asn Asp Ser Gln Asn
305                 310                 315                 320 gac cag tcc aag cag aac gat cag atc gac gta ttg ctg gcg aaa ggg   1008
Asp Gln Ser Lys Gln Asn Asp Gln Ile Asp Val Leu Leu Ala Lys Gly
                325                 330                 335 gtg aag gca ctg gca atc aac ctg gtt gac ccg gca gct gcg ggt acg   1056
Val Lys Ala Leu Ala Ile Asn Leu Val Asp Pro Ala Ala Ala Gly Thr
            340                 345                 350 gtg att gag aaa gcg cgt ggg caa aac gtg ccg gtg gtt ttc ttc aac   1104
Val Ile Glu Lys Ala Arg Gly Gln Asn Val Pro Val Val Phe Phe Asn
        355                 360                 365 aaa gaa ccg tct cgt aag gcg ctg gat agc tac gac aaa gcc tac tac   1152
Lys Glu Pro Ser Arg Lys Ala Leu Asp Ser Tyr Asp Lys Ala Tyr Tyr
    370                 375                 380 gtt ggc act gac tcc aaa gag tcc ggc att att caa ggc gat ttg att   1200
Val Gly Thr Asp Ser Lys Glu Ser Gly Ile Ile Gln Gly Asp Leu Ile
385                 390                 395                 400 gct aaa cac tgg gcg gcg aat cag ggt tgg gat ctg aac aaa gac ggt   1248
Ala Lys His Trp Ala Ala Asn Gln Gly Trp Asp Leu Asn Lys Asp Gly
                405                 410                 415 cag att cag ttc gta ctg ctg aaa ggt gaa ccg ggc cat ccg gat gca   1296
Gln Ile Gln Phe Val Leu Leu Lys Gly Glu Pro Gly His Pro Asp Ala
            420                 425                 430 gaa gca cgt acc act tac gtg att aaa gaa ttg aac gat aaa ggc atc   1344
Glu Ala Arg Thr Thr Tyr Val Ile Lys Glu Leu Asn Asp Lys Gly Ile
```

-continued

```
                  435                 440                 445
aaa act gaa cag tta cag tta gat acc gca atg tgg gac acc gct cag    1392
Lys Thr Glu Gln Leu Gln Leu Asp Thr Ala Met Trp Asp Thr Ala Gln
    450                 455                 460 gcg aaa gat aag atg gac gcc tgg ctg tct ggc ccg aac gcc aac aaa    1440
Ala Lys Asp Lys Met Asp Ala Trp Leu Ser Gly Pro Asn Ala Asn Lys
465                 470                 475                 480 atc gaa gtg gtt atc gcc aac aac gat gcg atg gca atg ggc gcg gtt    1488
Ile Glu Val Val Ile Ala Asn Asn Asp Ala Met Ala Met Gly Ala Val
                485                 490                 495 gaa gcg ctg aaa gca cac aac aag tcc agc att ccg gtg ttt ggc gtc    1536
Glu Ala Leu Lys Ala His Asn Lys Ser Ser Ile Pro Val Phe Gly Val
            500                 505                 510 gat gcg ctg cca gaa gcg ctg gcg ctg gtg aaa tcc ggt gca ctg gcg    1584
Asp Ala Leu Pro Glu Ala Leu Ala Leu Val Lys Ser Gly Ala Leu Ala
        515                 520                 525 ggc acc gta ctg aac gat gct aac aac cag gcg aaa gcg acc ttt gat    1632
Gly Thr Val Leu Asn Asp Ala Asn Asn Gln Ala Lys Ala Thr Phe Asp
    530                 535                 540 ctg gcg aaa aac ctg gcc gat ggt aaa ggt gcg gct gat ggc acc aac    1680
Leu Ala Lys Asn Leu Ala Asp Gly Lys Gly Ala Ala Asp Gly Thr Asn
545                 550                 555                 560 tgg aaa atc gac aac aaa gtg gtc cgc gta cct tat gtt ggc gta gat    1728
Trp Lys Ile Asp Asn Lys Val Val Arg Val Pro Tyr Val Gly Val Asp
                565                 570                 575 aaa gac aac ctg gct gaa ttc agc aag aaa ggc gcc ggt acc ggt gga    1776
Lys Asp Asn Leu Ala Glu Phe Ser Lys Lys Gly Ala Gly Thr Gly Gly
            580                 585                 590 atg gtg agc aag ggc gag gag ctg ttc acc ggg gtg gtg ccc atc ctg    1824
Met Val Ser Lys Gly Glu Glu Leu Phe Thr Gly Val Val Pro Ile Leu
        595                 600                 605 gtc gag ctg gac ggc gac gta aac ggc cac aag ttc agc gtg tcc ggc    1872
Val Glu Leu Asp Gly Asp Val Asn Gly His Lys Phe Ser Val Ser Gly
    610                 615                 620 gag ggc gag ggc gat gcc acc tac ggc aag ctg acc ctg aag ttc atc    1920
Glu Gly Glu Gly Asp Ala Thr Tyr Gly Lys Leu Thr Leu Lys Phe Ile
625                 630                 635                 640 tgc acc acc ggc aag ctg ccc gtg ccc tgg ccc acc ctc gtg acc acc    1968
Cys Thr Thr Gly Lys Leu Pro Val Pro Trp Pro Thr Leu Val Thr Thr
                645                 650                 655 ttc ggc tac ggc ctg cag tgc ttc gcc cgc tac ccc gac cac atg aag    2016
Phe Gly Tyr Gly Leu Gln Cys Phe Ala Arg Tyr Pro Asp His Met Lys
            660                 665                 670 cag cac gac ttc ttc aag tcc gcc atg ccc gaa ggc tac gtc cag gag    2064
Gln His Asp Phe Phe Lys Ser Ala Met Pro Glu Gly Tyr Val Gln Glu
        675                 680                 685 cgc acc atc ttc ttc aag gac gac ggc aac tac aag acc cgc gcc gag    2112
Arg Thr Ile Phe Phe Lys Asp Asp Gly Asn Tyr Lys Thr Arg Ala Glu
    690                 695                 700 gtg aag ttc gag ggc gac acc ctg gtg aac cgc atc gag ctg aag ggc    2160
Val Lys Phe Glu Gly Asp Thr Leu Val Asn Arg Ile Glu Leu Lys Gly
705                 710                 715                 720 atc gac ttc aag gag gac ggc aac atc ctg ggg cac aag ctg gag tac    2208
Ile Asp Phe Lys Glu Asp Gly Asn Ile Leu Gly His Lys Leu Glu Tyr
                725                 730                 735 aac tac aac agc cac aac gtc tat atc atg gcc gac aag cag aag aac    2256
Asn Tyr Asn Ser His Asn Val Tyr Ile Met Ala Asp Lys Gln Lys Asn
            740                 745                 750 ggc atc aag gtg aac ttc aag atc cgc cac aac atc gag gac ggc agc    2304
Gly Ile Lys Val Asn Phe Lys Ile Arg His Asn Ile Glu Asp Gly Ser
```

```
                    755                 760                 765
gtg cag ctc gcc gac cac tac cag cag aac acc ccc atc ggc gac ggc     2352
Val Gln Leu Ala Asp His Tyr Gln Gln Asn Thr Pro Ile Gly Asp Gly
770                 775                 780 ccc gtg ctg ctg ccc gac aac cac tac ctg agc tac cag tcc gcc ctg     2400
Pro Val Leu Leu Pro Asp Asn His Tyr Leu Ser Tyr Gln Ser Ala Leu
785                 790                 795                 800 agc aaa gac ccc aac gag aag cgc gat cac atg gtc ctg ctg gag ttc     2448
Ser Lys Asp Pro Asn Glu Lys Arg Asp His Met Val Leu Leu Glu Phe
                805                 810                 815 gtg acc gcc gcc ggg atc act ctc ggc atg gac gag ctg tac aag taa     2496
Val Thr Ala Ala Gly Ile Thr Leu Gly Met Asp Glu Leu Tyr Lys
820                 825                 830
```

<210> SEQ ID NO 16
<211> LENGTH: 831
<212> TYPE: PRT
<213> ORGANISM: Artificial Sequence
<220> FEATURE:
<223> OTHER INFORMATION: FLIP-mglBF16A-Y12S-CFP-D13R-YFP Vector

<400> SEQUENCE: 16

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
                20                  25                  30

Pro Gly Arg Ala Asp Thr Arg Ile Gly Val Thr Ile Tyr Lys Ser Ala
            35                  40                  45

Gly Met Val Ser Lys Gly Glu Glu Leu Phe Thr Gly Val Val Pro Ile
        50                  55                  60

Leu Val Glu Leu Asp Gly Asp Val Asn Gly His Lys Phe Ser Val Ser
65                  70                  75                  80

Gly Glu Gly Glu Gly Asp Ala Thr Tyr Gly Lys Leu Thr Leu Lys Phe
                85                  90                  95

Ile Cys Thr Thr Gly Lys Leu Pro Val Pro Trp Pro Thr Leu Val Thr
            100                 105                 110

Thr Leu Thr Trp Gly Val Gln Cys Phe Ser Arg Tyr Pro Asp His Met
        115                 120                 125

Lys Gln His Asp Phe Phe Lys Ser Ala Met Pro Glu Gly Tyr Val Gln
    130                 135                 140

Glu Arg Thr Ile Phe Phe Lys Asp Asp Gly Asn Tyr Lys Thr Arg Ala
145                 150                 155                 160

Glu Val Lys Phe Glu Gly Asp Thr Leu Val Asn Arg Ile Glu Leu Lys
                165                 170                 175

Gly Ile Asp Phe Lys Glu Asp Gly Asn Ile Leu Gly His Lys Leu Glu
            180                 185                 190

Tyr Asn Tyr Ile Ser His Asn Val Tyr Ile Thr Ala Asp Lys Gln Lys
        195                 200                 205

Asn Gly Ile Lys Ala Asn Phe Lys Ile Arg His Asn Ile Glu Asp Gly
    210                 215                 220

Ser Val Gln Leu Ala Asp His Tyr Gln Gln Asn Thr Pro Ile Gly Asp
225                 230                 235                 240

Gly Pro Val Leu Leu Pro Asp Asn His Tyr Leu Ser Thr Gln Ser Ala
                245                 250                 255

Leu Ser Lys Asp Pro Asn Glu Lys Arg Asp His Met Val Leu Leu Glu
            260                 265                 270

Phe Val Thr Ala Ala Gly Ile Thr Leu Gly Met Asp Glu Leu Tyr Gly
```

```
                275                 280                 285
Ser Arg Asp Asn Ala Met Ser Val Val Arg Lys Ala Ile Glu Gln Asp
290                 295                 300
Ala Lys Ala Ala Pro Asp Val Gln Leu Leu Met Asn Asp Ser Gln Asn
305                 310                 315                 320
Asp Gln Ser Lys Gln Asn Asp Gln Ile Asp Val Leu Leu Ala Lys Gly
                325                 330                 335
Val Lys Ala Leu Ala Ile Asn Leu Val Asp Pro Ala Ala Gly Thr
        340                 345                 350
Val Ile Glu Lys Ala Arg Gly Gln Asn Val Pro Val Val Phe Phe Asn
        355                 360                 365
Lys Glu Pro Ser Arg Lys Ala Leu Asp Ser Tyr Asp Lys Ala Tyr Tyr
370                 375                 380
Val Gly Thr Asp Ser Lys Glu Ser Gly Ile Ile Gln Gly Asp Leu Ile
385                 390                 395                 400
Ala Lys His Trp Ala Ala Asn Gln Gly Trp Asp Leu Asn Lys Asp Gly
                405                 410                 415
Gln Ile Gln Phe Val Leu Leu Lys Gly Glu Pro Gly His Pro Asp Ala
                420                 425                 430
Glu Ala Arg Thr Thr Tyr Val Ile Lys Glu Leu Asn Asp Lys Gly Ile
        435                 440                 445
Lys Thr Glu Gln Leu Gln Leu Asp Thr Ala Met Trp Asp Thr Ala Gln
450                 455                 460
Ala Lys Asp Lys Met Asp Ala Trp Leu Ser Gly Pro Asn Ala Asn Lys
465                 470                 475                 480
Ile Glu Val Val Ile Ala Asn Asn Asp Ala Met Ala Met Gly Ala Val
                485                 490                 495
Glu Ala Leu Lys Ala His Asn Lys Ser Ser Ile Pro Val Phe Gly Val
                500                 505                 510
Asp Ala Leu Pro Glu Ala Leu Ala Leu Val Lys Ser Gly Ala Leu Ala
                515                 520                 525
Gly Thr Val Leu Asn Asp Ala Asn Asn Gln Ala Lys Ala Thr Phe Asp
530                 535                 540
Leu Ala Lys Asn Leu Ala Asp Gly Lys Gly Ala Ala Asp Gly Thr Asn
545                 550                 555                 560
Trp Lys Ile Asp Asn Lys Val Val Arg Val Pro Tyr Val Gly Val Asp
                565                 570                 575
Lys Asp Asn Leu Ala Glu Phe Ser Lys Lys Gly Ala Gly Thr Gly Gly
                580                 585                 590
Met Val Ser Lys Gly Glu Glu Leu Phe Thr Gly Val Val Pro Ile Leu
                595                 600                 605
Val Glu Leu Asp Gly Asp Val Asn Gly His Lys Phe Ser Val Ser Gly
        610                 615                 620
Glu Gly Glu Gly Asp Ala Thr Tyr Gly Lys Leu Thr Leu Lys Phe Ile
625                 630                 635                 640
Cys Thr Thr Gly Lys Leu Pro Val Pro Trp Pro Thr Leu Val Thr Thr
                645                 650                 655
Phe Gly Tyr Gly Leu Gln Cys Phe Ala Arg Tyr Pro Asp His Met Lys
                660                 665                 670
Gln His Asp Phe Phe Lys Ser Ala Met Pro Glu Gly Tyr Val Gln Glu
        675                 680                 685
Arg Thr Ile Phe Phe Lys Asp Asp Gly Asn Tyr Lys Thr Arg Ala Glu
690                 695                 700
```

```
Val Lys Phe Glu Gly Asp Thr Leu Val Asn Arg Ile Glu Leu Lys Gly
705                 710                 715                 720

Ile Asp Phe Lys Glu Asp Gly Asn Ile Leu Gly His Lys Leu Glu Tyr
                725                 730                 735

Asn Tyr Asn Ser His Asn Val Tyr Ile Met Ala Asp Lys Gln Lys Asn
            740                 745                 750

Gly Ile Lys Val Asn Phe Lys Ile Arg His Asn Ile Glu Asp Gly Ser
        755                 760                 765

Val Gln Leu Ala Asp His Tyr Gln Gln Asn Thr Pro Ile Gly Asp Gly
    770                 775                 780

Pro Val Leu Leu Pro Asp Asn His Tyr Leu Ser Tyr Gln Ser Ala Leu
785                 790                 795                 800

Ser Lys Asp Pro Asn Glu Lys Arg Asp His Met Val Leu Leu Glu Phe
                805                 810                 815

Val Thr Ala Ala Gly Ile Thr Leu Gly Met Asp Glu Leu Tyr Lys
            820                 825                 830

<210> SEQ ID NO 17
<211> LENGTH: 2496
<212> TYPE: DNA
<213> ORGANISM: Artificial Sequence
<220> FEATURE:
<223> OTHER INFORMATION: FLIP-mglBF16A-G275S-CFP-K276R-YFP Vector
<220> FEATURE:
<221> NAME/KEY: CDS
<222> LOCATION: (1)..(2496)

<400> SEQUENCE: 17 atg cgg ggt tct cat cat cat cat cat cat ggt atg gct agc atg act      48
Met Arg Gly Ser His His His His His His Gly Met Ala Ser Met Thr
1               5                   10                  15 ggt gga cag caa atg ggt cgg gat ctg tac gac gat gac gat aag gat      96
Gly Gly Gln Gln Met Gly Arg Asp Leu Tyr Asp Asp Asp Asp Lys Asp
            20                  25                  30 ccg ggc cgc gct gat act cgc att ggt gta aca atc tat aag tac gac     144
Pro Gly Arg Ala Asp Thr Arg Ile Gly Val Thr Ile Tyr Lys Tyr Asp
        35                  40                  45 gat aac gcg atg tct gta gtg cgc aag gct att gag caa gat gcg aaa     192
Asp Asn Ala Met Ser Val Val Arg Lys Ala Ile Glu Gln Asp Ala Lys
    50                  55                  60 gcc gcg cca gat gtt cag ctg ctg atg aat gat tct cag aat gac cag     240
Ala Ala Pro Asp Val Gln Leu Leu Met Asn Asp Ser Gln Asn Asp Gln
65                  70                  75                  80 tcc aag cag aac gat cag atc gac gta ttg ctg gcg aaa ggg gtg aag     288
Ser Lys Gln Asn Asp Gln Ile Asp Val Leu Leu Ala Lys Gly Val Lys
                85                  90                  95 gca ctg gca atc aac ctg gtt gac ccg gca gct gcg ggt acg gtg att     336
Ala Leu Ala Ile Asn Leu Val Asp Pro Ala Ala Ala Gly Thr Val Ile
            100                 105                 110 gag aaa gcg cgt ggg caa aac gtg ccg gtg gtt ttc ttc aac aaa gaa     384
Glu Lys Ala Arg Gly Gln Asn Val Pro Val Val Phe Phe Asn Lys Glu
        115                 120                 125 ccg tct cgt aag gcg ctg gat agc tac gac aaa gcc tac tac gtt ggc     432
Pro Ser Arg Lys Ala Leu Asp Ser Tyr Asp Lys Ala Tyr Tyr Val Gly
    130                 135                 140 act gac tcc aaa gag tcc ggc att att caa ggc gat ttg att gct aaa     480
Thr Asp Ser Lys Glu Ser Gly Ile Ile Gln Gly Asp Leu Ile Ala Lys
145                 150                 155                 160 cac tgg gcg gcg aat cag ggt tgg gat ctg aac aaa gac ggt cag att     528
His Trp Ala Ala Asn Gln Gly Trp Asp Leu Asn Lys Asp Gly Gln Ile
                165                 170                 175
```

| | | | | | | | | | | | | | | | |
|---|---|---|---|---|---|---|---|---|---|---|---|---|---|---|---|
| cag | ttc | gta | ctg | ctg | aaa | ggt | gaa | ccg | ggc | cat | ccg | gat | gca | gaa | gca |
| Gln | Phe | Val | Leu | Leu | Lys | Gly | Glu | Pro | Gly | His | Pro | Asp | Ala | Glu | Ala |
| | | | 180 | | | | | 185 | | | | | 190 | | |

576

| | | | | | | | | | | | | | | | |
|---|---|---|---|---|---|---|---|---|---|---|---|---|---|---|---|
| cgt | acc | act | tac | gtg | att | aaa | gaa | ttg | aac | gat | aaa | ggc | atc | aaa | act |
| Arg | Thr | Thr | Tyr | Val | Ile | Lys | Glu | Leu | Asn | Asp | Lys | Gly | Ile | Lys | Thr |
| | | 195 | | | | | 200 | | | | | 205 | | | |

624

| | | | | | | | | | | | | | | | |
|---|---|---|---|---|---|---|---|---|---|---|---|---|---|---|---|
| gaa | cag | tta | cag | tta | gat | acc | gca | atg | tgg | gac | acc | gct | cag | gcg | aaa |
| Glu | Gln | Leu | Gln | Leu | Asp | Thr | Ala | Met | Trp | Asp | Thr | Ala | Gln | Ala | Lys |
| 210 | | | | | 215 | | | | | 220 | | | | | |

672

| | | | | | | | | | | | | | | | |
|---|---|---|---|---|---|---|---|---|---|---|---|---|---|---|---|
| gat | aag | atg | gac | gcc | tgg | ctg | tct | ggc | ccg | aac | gcc | aac | aaa | atc | gaa |
| Asp | Lys | Met | Asp | Ala | Trp | Leu | Ser | Gly | Pro | Asn | Ala | Asn | Lys | Ile | Glu |
| 225 | | | | 230 | | | | | 235 | | | | | 240 | |

720

| | | | | | | | | | | | | | | | |
|---|---|---|---|---|---|---|---|---|---|---|---|---|---|---|---|
| gtg | gtt | atc | gcc | aac | aac | gat | gcg | atg | gca | atg | ggc | gcg | gtt | gaa | gcg |
| Val | Val | Ile | Ala | Asn | Asn | Asp | Ala | Met | Ala | Met | Gly | Ala | Val | Glu | Ala |
| | | | | 245 | | | | | 250 | | | | | 255 | |

768

| | | | | | | | | | | | | | | | |
|---|---|---|---|---|---|---|---|---|---|---|---|---|---|---|---|
| ctg | aaa | gca | cac | aac | aag | tcc | agc | att | ccg | gtg | ttt | ggc | gtc | gat | gcg |
| Leu | Lys | Ala | His | Asn | Lys | Ser | Ser | Ile | Pro | Val | Phe | Gly | Val | Asp | Ala |
| | | | | 260 | | | | | 265 | | | | | 270 | |

816

| | | | | | | | | | | | | | | | |
|---|---|---|---|---|---|---|---|---|---|---|---|---|---|---|---|
| ctg | cca | gaa | gcg | ctg | gcg | ctg | gtg | aaa | tcc | ggt | gca | ctg | gcg | ggc | acc |
| Leu | Pro | Glu | Ala | Leu | Ala | Leu | Val | Lys | Ser | Gly | Ala | Leu | Ala | Gly | Thr |
| | 275 | | | | | 280 | | | | | 285 | | | | |

864

| | | | | | | | | | | | | | | | |
|---|---|---|---|---|---|---|---|---|---|---|---|---|---|---|---|
| gta | ctg | aac | gat | gct | aac | aac | cag | gcg | aaa | gcg | acc | ttt | gat | ctg | gcg |
| Val | Leu | Asn | Asp | Ala | Asn | Asn | Gln | Ala | Lys | Ala | Thr | Phe | Asp | Leu | Ala |
| | 290 | | | | | 295 | | | | | 300 | | | | |

912

| | | | | | | | | | | | | | | | |
|---|---|---|---|---|---|---|---|---|---|---|---|---|---|---|---|
| aaa | aac | ctg | gcc | gat | tcg | gct | ggt | atg | gtg | agc | aag | ggc | gag | gag | ctg |
| Lys | Asn | Leu | Ala | Asp | Ser | Ala | Gly | Met | Val | Ser | Lys | Gly | Glu | Glu | Leu |
| 305 | | | | 310 | | | | | 315 | | | | | 320 | |

960

| | | | | | | | | | | | | | | | |
|---|---|---|---|---|---|---|---|---|---|---|---|---|---|---|---|
| ttc | acc | ggg | gtg | gtg | ccc | atc | ctg | gtc | gag | ctg | gac | ggc | gac | gta | aac |
| Phe | Thr | Gly | Val | Val | Pro | Ile | Leu | Val | Glu | Leu | Asp | Gly | Asp | Val | Asn |
| | | | | 325 | | | | | 330 | | | | | 335 | |

1008

| | | | | | | | | | | | | | | | |
|---|---|---|---|---|---|---|---|---|---|---|---|---|---|---|---|
| ggc | cac | aag | ttc | agc | gtg | tcc | ggc | gag | ggc | gag | ggc | gat | gcc | acc | tac |
| Gly | His | Lys | Phe | Ser | Val | Ser | Gly | Glu | Gly | Glu | Gly | Asp | Ala | Thr | Tyr |
| | | | 340 | | | | | 345 | | | | | 350 | | |

1056

| | | | | | | | | | | | | | | | |
|---|---|---|---|---|---|---|---|---|---|---|---|---|---|---|---|
| ggc | aag | ctg | acc | ctg | aag | ttc | atc | tgc | acc | acc | ggc | aag | ctg | ccc | gtg |
| Gly | Lys | Leu | Thr | Leu | Lys | Phe | Ile | Cys | Thr | Thr | Gly | Lys | Leu | Pro | Val |
| | | | 355 | | | | | 360 | | | | | 365 | | |

1104

| | | | | | | | | | | | | | | | |
|---|---|---|---|---|---|---|---|---|---|---|---|---|---|---|---|
| ccc | tgg | ccc | acc | ctc | gtg | acc | acc | ctg | acc | tgg | ggc | gtg | cag | tgc | ttc |
| Pro | Trp | Pro | Thr | Leu | Val | Thr | Thr | Leu | Thr | Trp | Gly | Val | Gln | Cys | Phe |
| | 370 | | | | | 375 | | | | | 380 | | | | |

1152

| | | | | | | | | | | | | | | | |
|---|---|---|---|---|---|---|---|---|---|---|---|---|---|---|---|
| agc | cgc | tac | ccc | gac | cac | atg | aag | cag | cac | gac | ttc | ttc | aag | tcc | gcc |
| Ser | Arg | Tyr | Pro | Asp | His | Met | Lys | Gln | His | Asp | Phe | Phe | Lys | Ser | Ala |
| 385 | | | | | 390 | | | | | 395 | | | | | 400 |

1200

| | | | | | | | | | | | | | | | |
|---|---|---|---|---|---|---|---|---|---|---|---|---|---|---|---|
| atg | ccc | gaa | ggc | tac | gtc | cag | gag | cgc | acc | atc | ttc | ttc | aag | gac | gac |
| Met | Pro | Glu | Gly | Tyr | Val | Gln | Glu | Arg | Thr | Ile | Phe | Phe | Lys | Asp | Asp |
| | | | | 405 | | | | | 410 | | | | | 415 | |

1248

| | | | | | | | | | | | | | | | |
|---|---|---|---|---|---|---|---|---|---|---|---|---|---|---|---|
| ggc | aac | tac | aag | acc | cgc | gcc | gag | gtg | aag | ttc | gag | ggc | gac | acc | ctg |
| Gly | Asn | Tyr | Lys | Thr | Arg | Ala | Glu | Val | Lys | Phe | Glu | Gly | Asp | Thr | Leu |
| | | | 420 | | | | | 425 | | | | | 430 | | |

1296

| | | | | | | | | | | | | | | | |
|---|---|---|---|---|---|---|---|---|---|---|---|---|---|---|---|
| gtg | aac | cgc | atc | gag | ctg | aag | ggc | atc | gac | ttc | aag | gag | gac | ggc | aac |
| Val | Asn | Arg | Ile | Glu | Leu | Lys | Gly | Ile | Asp | Phe | Lys | Glu | Asp | Gly | Asn |
| | | 435 | | | | | 440 | | | | | 445 | | | |

1344

| | | | | | | | | | | | | | | | |
|---|---|---|---|---|---|---|---|---|---|---|---|---|---|---|---|
| atc | ctg | ggg | cac | aag | ctg | gag | tac | aac | tac | atc | agc | cac | aac | gtc | tat |
| Ile | Leu | Gly | His | Lys | Leu | Glu | Tyr | Asn | Tyr | Ile | Ser | His | Asn | Val | Tyr |
| 450 | | | | | 455 | | | | | 460 | | | | | |

1392

| | | | | | | | | | | | | | | | |
|---|---|---|---|---|---|---|---|---|---|---|---|---|---|---|---|
| atc | acc | gcc | gac | aag | cag | aag | aac | ggc | atc | aag | gcc | aac | ttc | aag | atc |
| Ile | Thr | Ala | Asp | Lys | Gln | Lys | Asn | Gly | Ile | Lys | Ala | Asn | Phe | Lys | Ile |
| 465 | | | | | 470 | | | | | 475 | | | | | 480 |

1440

| | | | | | | | | | | | | | | | |
|---|---|---|---|---|---|---|---|---|---|---|---|---|---|---|---|
| cgc | cac | aac | atc | gag | gac | ggc | agc | gtg | cag | ctc | gcc | gac | cac | tac | cag |
| Arg | His | Asn | Ile | Glu | Asp | Gly | Ser | Val | Gln | Leu | Ala | Asp | His | Tyr | Gln |
| | | | | 485 | | | | | 490 | | | | | 495 | |

1488

| | |
|---|---|
| cag aac acc ccc atc ggc gac ggc ccc gtg ctg ctg ccc gac aac cac<br>Gln Asn Thr Pro Ile Gly Asp Gly Pro Val Leu Leu Pro Asp Asn His<br>500 505 510 | 1536 |
| tac ctg agc acc cag tcc gcc ctg agc aaa gac ccc aac gag aag cgc<br>Tyr Leu Ser Thr Gln Ser Ala Leu Ser Lys Asp Pro Asn Glu Lys Arg<br>515 520 525 | 1584 |
| gat cac atg gtc ctg ctg gag ttc gtg acc gcc gcc ggg atc act ctc<br>Asp His Met Val Leu Leu Glu Phe Val Thr Ala Ala Gly Ile Thr Leu<br>530 535 540 | 1632 |
| ggc atg gac gag ctg tac ggt agc cga ggt gcg gct gat ggc acc aac<br>Gly Met Asp Glu Leu Tyr Gly Ser Arg Gly Ala Ala Asp Gly Thr Asn<br>545 550 555 560 | 1680 |
| tgg aaa atc gac aac aaa gtg gtc cgc gta cct tat gtt ggc gta gat<br>Trp Lys Ile Asp Asn Lys Val Val Arg Val Pro Tyr Val Gly Val Asp<br>565 570 575 | 1728 |
| aaa gac aac ctg gct gaa ttc agc aag aaa ggc gcc ggt acc ggt gga<br>Lys Asp Asn Leu Ala Glu Phe Ser Lys Lys Gly Ala Gly Thr Gly Gly<br>580 585 590 | 1776 |
| atg gtg agc aag ggc gag gag ctg ttc acc ggg gtg gtg ccc atc ctg<br>Met Val Ser Lys Gly Glu Glu Leu Phe Thr Gly Val Val Pro Ile Leu<br>595 600 605 | 1824 |
| gtc gag ctg gac ggc gac gta aac ggc cac aag ttc agc gtg tcc ggc<br>Val Glu Leu Asp Gly Asp Val Asn Gly His Lys Phe Ser Val Ser Gly<br>610 615 620 | 1872 |
| gag ggc gag ggc gat gcc acc tac ggc aag ctg acc ctg aag ttc atc<br>Glu Gly Glu Gly Asp Ala Thr Tyr Gly Lys Leu Thr Leu Lys Phe Ile<br>625 630 635 640 | 1920 |
| tgc acc acc ggc aag ctg ccc gtg ccc tgg ccc acc ctc gtg acc acc<br>Cys Thr Thr Gly Lys Leu Pro Val Pro Trp Pro Thr Leu Val Thr Thr<br>645 650 655 | 1968 |
| ttc ggc tac ggc ctg cag tgc ttc gcc cgc tac ccc gac cac atg aag<br>Phe Gly Tyr Gly Leu Gln Cys Phe Ala Arg Tyr Pro Asp His Met Lys<br>660 665 670 | 2016 |
| cag cac gac ttc ttc aag tcc gcc atg ccc gaa ggc tac gtc cag gag<br>Gln His Asp Phe Phe Lys Ser Ala Met Pro Glu Gly Tyr Val Gln Glu<br>675 680 685 | 2064 |
| cgc acc atc ttc ttc aag gac gac ggc aac tac aag acc cgc gcc gag<br>Arg Thr Ile Phe Phe Lys Asp Asp Gly Asn Tyr Lys Thr Arg Ala Glu<br>690 695 700 | 2112 |
| gtg aag ttc gag ggc gac acc ctg gtg aac cgc atc gag ctg aag ggc<br>Val Lys Phe Glu Gly Asp Thr Leu Val Asn Arg Ile Glu Leu Lys Gly<br>705 710 715 720 | 2160 |
| atc gac ttc aag gag gac ggc aac atc ctg ggg cac aag ctg gag tac<br>Ile Asp Phe Lys Glu Asp Gly Asn Ile Leu Gly His Lys Leu Glu Tyr<br>725 730 735 | 2208 |
| aac tac aac agc cac aac gtc tat atc atg gcc gac aag cag aag aac<br>Asn Tyr Asn Ser His Asn Val Tyr Ile Met Ala Asp Lys Gln Lys Asn<br>740 745 750 | 2256 |
| ggc atc aag gtg aac ttc aag atc cgc cac aac atc gag gac ggc agc<br>Gly Ile Lys Val Asn Phe Lys Ile Arg His Asn Ile Glu Asp Gly Ser<br>755 760 765 | 2304 |
| gtg cag ctc gcc gac cac tac cag cag aac acc ccc atc ggc gac ggc<br>Val Gln Leu Ala Asp His Tyr Gln Gln Asn Thr Pro Ile Gly Asp Gly<br>770 775 780 | 2352 |
| ccc gtg ctg ctg ccc gac aac cac tac ctg agc tac cag tcc gcc ctg<br>Pro Val Leu Leu Pro Asp Asn His Tyr Leu Ser Tyr Gln Ser Ala Leu<br>785 790 795 800 | 2400 |
| agc aaa gac ccc aac gag aag cgc gat cac atg gtc ctg ctg gag ttc<br>Ser Lys Asp Pro Asn Glu Lys Arg Asp His Met Val Leu Leu Glu Phe<br>805 810 815 | 2448 |

```
gtg acc gcc gcc ggg atc act ctc ggc atg gac gag ctg tac aag taa    2496
Val Thr Ala Ala Gly Ile Thr Leu Gly Met Asp Glu Leu Tyr Lys
            820                 825                 830
```

<210> SEQ ID NO 18
<211> LENGTH: 831
<212> TYPE: PRT
<213> ORGANISM: Artificial Sequence
<220> FEATURE:
<223> OTHER INFORMATION: FLIP-mglBF16A-G275S-CFP-K276R-YFP Vector

<400> SEQUENCE: 18

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Ala Asp Thr Arg Ile Gly Val Thr Ile Tyr Lys Tyr Asp
            35                  40                  45

Asp Asn Ala Met Ser Val Val Arg Lys Ala Ile Glu Gln Asp Ala Lys
    50                  55                  60

Ala Ala Pro Asp Val Gln Leu Leu Met Asn Asp Ser Gln Asn Asp Gln
65                  70                  75                  80

Ser Lys Gln Asn Asp Gln Ile Asp Val Leu Leu Ala Lys Gly Val Lys
                85                  90                  95

Ala Leu Ala Ile Asn Leu Val Asp Pro Ala Ala Ala Gly Thr Val Ile
            100                 105                 110

Glu Lys Ala Arg Gly Gln Asn Val Pro Val Val Phe Phe Asn Lys Glu
        115                 120                 125

Pro Ser Arg Lys Ala Leu Asp Ser Tyr Asp Lys Ala Tyr Tyr Val Gly
    130                 135                 140

Thr Asp Ser Lys Glu Ser Gly Ile Ile Gln Gly Asp Leu Ile Ala Lys
145                 150                 155                 160

His Trp Ala Ala Asn Gln Gly Trp Asp Leu Asn Lys Asp Gly Gln Ile
                165                 170                 175

Gln Phe Val Leu Leu Lys Gly Glu Pro Gly His Pro Asp Ala Glu Ala
            180                 185                 190

Arg Thr Thr Tyr Val Ile Lys Glu Leu Asn Asp Lys Gly Ile Lys Thr
        195                 200                 205

Glu Gln Leu Gln Leu Asp Thr Ala Met Trp Asp Thr Ala Gln Ala Lys
    210                 215                 220

Asp Lys Met Asp Ala Trp Leu Ser Gly Pro Asn Ala Asn Lys Ile Glu
225                 230                 235                 240

Val Val Ile Ala Asn Asn Asp Ala Met Ala Met Gly Ala Val Glu Ala
                245                 250                 255

Leu Lys Ala His Asn Lys Ser Ser Ile Pro Val Phe Gly Val Asp Ala
            260                 265                 270

Leu Pro Glu Ala Leu Ala Leu Val Lys Ser Gly Ala Leu Ala Gly Thr
        275                 280                 285

Val Leu Asn Asp Ala Asn Asn Gln Ala Lys Ala Thr Phe Asp Leu Ala
    290                 295                 300

Lys Asn Leu Ala Asp Ser Ala Gly Met Val Ser Lys Gly Glu Glu Leu
305                 310                 315                 320

Phe Thr Gly Val Val Pro Ile Leu Val Glu Leu Asp Gly Asp Val Asn
                325                 330                 335

Gly His Lys Phe Ser Val Ser Gly Glu Gly Glu Gly Asp Ala Thr Tyr
            340                 345                 350
```

```
Gly Lys Leu Thr Leu Lys Phe Ile Cys Thr Thr Gly Lys Leu Pro Val
            355                 360                 365
Pro Trp Pro Thr Leu Val Thr Thr Leu Thr Trp Gly Val Gln Cys Phe
        370                 375                 380
Ser Arg Tyr Pro Asp His Met Lys Gln His Asp Phe Phe Lys Ser Ala
385                 390                 395                 400
Met Pro Glu Gly Tyr Val Gln Glu Arg Thr Ile Phe Phe Lys Asp Asp
                405                 410                 415
Gly Asn Tyr Lys Thr Arg Ala Glu Val Lys Phe Glu Gly Asp Thr Leu
            420                 425                 430
Val Asn Arg Ile Glu Leu Lys Gly Ile Asp Phe Lys Glu Asp Gly Asn
        435                 440                 445
Ile Leu Gly His Lys Leu Glu Tyr Asn Tyr Ile Ser His Asn Val Tyr
    450                 455                 460
Ile Thr Ala Asp Lys Gln Lys Asn Gly Ile Lys Ala Asn Phe Lys Ile
465                 470                 475                 480
Arg His Asn Ile Glu Asp Gly Ser Val Gln Leu Ala Asp His Tyr Gln
                485                 490                 495
Gln Asn Thr Pro Ile Gly Asp Gly Pro Val Leu Leu Pro Asp Asn His
            500                 505                 510
Tyr Leu Ser Thr Gln Ser Ala Leu Ser Lys Asp Pro Asn Glu Lys Arg
        515                 520                 525
Asp His Met Val Leu Leu Glu Phe Val Thr Ala Ala Gly Ile Thr Leu
    530                 535                 540
Gly Met Asp Glu Leu Tyr Gly Ser Arg Gly Ala Ala Asp Gly Thr Asn
545                 550                 555                 560
Trp Lys Ile Asp Asn Lys Val Val Arg Val Pro Tyr Val Gly Val Asp
                565                 570                 575
Lys Asp Asn Leu Ala Glu Phe Ser Lys Lys Gly Ala Gly Thr Gly Gly
            580                 585                 590
Met Val Ser Lys Gly Glu Glu Leu Phe Thr Gly Val Val Pro Ile Leu
        595                 600                 605
Val Glu Leu Asp Gly Asp Val Asn Gly His Lys Phe Ser Val Ser Gly
    610                 615                 620
Glu Gly Glu Gly Asp Ala Thr Tyr Gly Lys Leu Thr Leu Lys Phe Ile
625                 630                 635                 640
Cys Thr Thr Gly Lys Leu Pro Val Pro Trp Pro Thr Leu Val Thr Thr
                645                 650                 655
Phe Gly Tyr Gly Leu Gln Cys Phe Ala Arg Tyr Pro Asp His Met Lys
            660                 665                 670
Gln His Asp Phe Phe Lys Ser Ala Met Pro Glu Gly Tyr Val Gln Glu
        675                 680                 685
Arg Thr Ile Phe Phe Lys Asp Asp Gly Asn Tyr Lys Thr Arg Ala Glu
    690                 695                 700
Val Lys Phe Glu Gly Asp Thr Leu Val Asn Arg Ile Glu Leu Lys Gly
705                 710                 715                 720
Ile Asp Phe Lys Glu Asp Gly Asn Ile Leu Gly His Lys Leu Glu Tyr
                725                 730                 735
Asn Tyr Asn Ser His Asn Val Tyr Ile Met Ala Asp Lys Gln Lys Asn
            740                 745                 750
Gly Ile Lys Val Asn Phe Lys Ile Arg His Asn Ile Glu Asp Gly Ser
        755                 760                 765
Val Gln Leu Ala Asp His Tyr Gln Gln Asn Thr Pro Ile Gly Asp Gly
```

```
              770                 775                 780
Pro Val Leu Leu Pro Asp Asn His Tyr Leu Ser Tyr Gln Ser Ala Leu
785                 790                 795                 800

Ser Lys Asp Pro Asn Glu Lys Arg Asp His Met Val Leu Leu Glu Phe
                805                 810                 815

Val Thr Ala Ala Gly Ile Thr Leu Gly Met Asp Glu Leu Tyr Lys
            820                 825                 830

<210> SEQ ID NO 19
<211> LENGTH: 2496
<212> TYPE: DNA
<213> ORGANISM: Artificial Sequence
<220> FEATURE:
<223> OTHER INFORMATION: FLIP-YFP-mglBF16A-Y12S-CFP-D13R Vector
<220> FEATURE:
<221> NAME/KEY: CDS
<222> LOCATION: (1)..(2496)

<400> SEQUENCE: 19 atg cgg ggt tct cat cat cat cat cat cat ggt atg gct agc atg act        48
Met Arg Gly Ser His His His His His His Gly Met Ala Ser Met Thr
1               5                   10                  15 ggt gga cag caa atg ggt cgg gat ctg tac gac gat gac gat aag gat        96
Gly Gly Gln Gln Met Gly Arg Asp Leu Tyr Asp Asp Asp Asp Lys Asp
            20                  25                  30 ccg ggc cgc atg gtg agc aag ggc gag gag ctg ttc acc ggg gtg gtg       144
Pro Gly Arg Met Val Ser Lys Gly Glu Glu Leu Phe Thr Gly Val Val
        35                  40                  45 ccc atc ctg gtc gag ctg gac ggc gac gta aac ggc cac aag ttc agc       192
Pro Ile Leu Val Glu Leu Asp Gly Asp Val Asn Gly His Lys Phe Ser
    50                  55                  60 gtg tcc ggc gag ggc gag ggc gat gcc acc tac ggc aag ctg acc ctg       240
Val Ser Gly Glu Gly Glu Gly Asp Ala Thr Tyr Gly Lys Leu Thr Leu
65                  70                  75                  80 aag ttc atc tgc acc acc ggc aag ctg ccc gtg ccc tgg ccc acc ctc       288
Lys Phe Ile Cys Thr Thr Gly Lys Leu Pro Val Pro Trp Pro Thr Leu
                85                  90                  95 gtg acc acc ctg acc tgg ggc gtg cag tgc ttc agc cgc tac ccc gac       336
Val Thr Thr Leu Thr Trp Gly Val Gln Cys Phe Ser Arg Tyr Pro Asp
            100                 105                 110 cac atg aag cag cac gac ttc ttc aag tcc gcc atg ccc gaa ggc tac       384
His Met Lys Gln His Asp Phe Phe Lys Ser Ala Met Pro Glu Gly Tyr
        115                 120                 125 gtc cag gag cgc acc atc ttc ttc aag gac gac ggc aac tac aag acc       432
Val Gln Glu Arg Thr Ile Phe Phe Lys Asp Asp Gly Asn Tyr Lys Thr
    130                 135                 140 cgc gcc gag gtg aag ttc gag ggc gac acc ctg gtg aac cgc atc gag       480
Arg Ala Glu Val Lys Phe Glu Gly Asp Thr Leu Val Asn Arg Ile Glu
145                 150                 155                 160 ctg aag ggc atc gac ttc aag gag gac ggc aac atc ctg ggg cac aag       528
Leu Lys Gly Ile Asp Phe Lys Glu Asp Gly Asn Ile Leu Gly His Lys
                165                 170                 175 ctg gag tac aac tac atc agc cac aac gtc tat atc acc gcc gac aag       576
Leu Glu Tyr Asn Tyr Ile Ser His Asn Val Tyr Ile Thr Ala Asp Lys
            180                 185                 190 cag aag aac ggc atc aag gcc aac ttc aag atc cgc cac aac atc gag       624
Gln Lys Asn Gly Ile Lys Ala Asn Phe Lys Ile Arg His Asn Ile Glu
        195                 200                 205 gac ggc agc gtg cag ctc gcc gac cac tac cag cag aac acc ccc atc       672
Asp Gly Ser Val Gln Leu Ala Asp His Tyr Gln Gln Asn Thr Pro Ile
    210                 215                 220
```

```
ggc gac ggc ccc gtg ctg ctg ccc gac aac cac tac ctg agc acc cag      720
Gly Asp Gly Pro Val Leu Leu Pro Asp Asn His Tyr Leu Ser Thr Gln
225                 230                 235                 240 tcc gcc ctg agc aaa gac ccc aac gag aag cgc gat cac atg gtc ctg      768
Ser Ala Leu Ser Lys Asp Pro Asn Glu Lys Arg Asp His Met Val Leu
                245                 250                 255 ctg gag ttc gtg acc gcc gcc ggg atc act ctc ggc atg gac gag ctg      816
Leu Glu Phe Val Thr Ala Ala Gly Ile Thr Leu Gly Met Asp Glu Leu
            260                 265                 270 tac aag ggt ggt acc gga ggc gct gat act cgc att ggt gta aca          864
Tyr Lys Gly Gly Thr Gly Gly Ala Asp Thr Arg Ile Gly Val Thr
        275                 280                 285 atc tat aag tcg gct ggt atg gtg agc aag ggc gag gag ctg ttc acc      912
Ile Tyr Lys Ser Ala Gly Met Val Ser Lys Gly Glu Glu Leu Phe Thr
    290                 295                 300 ggg gtg gtg ccc atc ctg gtc gag ctg gac ggc gac gta aac ggc cac      960
Gly Val Val Pro Ile Leu Val Glu Leu Asp Gly Asp Val Asn Gly His
305                 310                 315                 320 aag ttc agc gtg tcc ggc gag ggc gag ggc gat gcc acc tac ggc aag     1008
Lys Phe Ser Val Ser Gly Glu Gly Glu Gly Asp Ala Thr Tyr Gly Lys
                325                 330                 335 ctg acc ctg aag ttc atc tgc acc acc ggc aag ctg ccc gtg ccc tgg     1056
Leu Thr Leu Lys Phe Ile Cys Thr Thr Gly Lys Leu Pro Val Pro Trp
            340                 345                 350 ccc acc ctc gtg acc acc ctg acc tgg ggc gtg cag tgc ttc agc cgc     1104
Pro Thr Leu Val Thr Thr Leu Thr Trp Gly Val Gln Cys Phe Ser Arg
        355                 360                 365 tac ccc gac cac atg aag cag cac gac ttc ttc aag tcc gcc atg ccc     1152
Tyr Pro Asp His Met Lys Gln His Asp Phe Phe Lys Ser Ala Met Pro
    370                 375                 380 gaa ggc tac gtc cag gag cgc acc atc ttc ttc aag gac gac ggc aac     1200
Glu Gly Tyr Val Gln Glu Arg Thr Ile Phe Phe Lys Asp Asp Gly Asn
385                 390                 395                 400 tac aag acc cgc gcc gag gtg aag ttc gag ggc gac acc ctg gtg aac     1248
Tyr Lys Thr Arg Ala Glu Val Lys Phe Glu Gly Asp Thr Leu Val Asn
                405                 410                 415 cgc atc gag ctg aag ggc atc gac ttc aag gag gac ggc aac atc ctg     1296
Arg Ile Glu Leu Lys Gly Ile Asp Phe Lys Glu Asp Gly Asn Ile Leu
            420                 425                 430 ggg cac aag ctg gag tac aac tac atc agc cac aac gtc tat atc acc     1344
Gly His Lys Leu Glu Tyr Asn Tyr Ile Ser His Asn Val Tyr Ile Thr
        435                 440                 445 gcc gac aag cag aag aac ggc atc aag gcc aac ttc aag atc cgc cac     1392
Ala Asp Lys Gln Lys Asn Gly Ile Lys Ala Asn Phe Lys Ile Arg His
    450                 455                 460 aac atc gag gac ggc agc gtg cag ctc gcc gac cac tac cag cag aac     1440
Asn Ile Glu Asp Gly Ser Val Gln Leu Ala Asp His Tyr Gln Gln Asn
465                 470                 475                 480 acc ccc atc ggc gac ggc ccc gtg ctg ctg ccc gac aac cac tac ctg     1488
Thr Pro Ile Gly Asp Gly Pro Val Leu Leu Pro Asp Asn His Tyr Leu
                485                 490                 495 agc acc cag tcc gcc ctg agc aaa gac ccc aac gag aag cgc gat cac     1536
Ser Thr Gln Ser Ala Leu Ser Lys Asp Pro Asn Glu Lys Arg Asp His
            500                 505                 510 atg gtc ctg ctg gag ttc gtg acc gcc gcc ggg atc act ctc ggc atg     1584
Met Val Leu Leu Glu Phe Val Thr Ala Ala Gly Ile Thr Leu Gly Met
        515                 520                 525 gac gag ctg tac ggt agc cga gat aac gcg atg tct gta gtg cgc aag     1632
Asp Glu Leu Tyr Gly Ser Arg Asp Asn Ala Met Ser Val Val Arg Lys
    530                 535                 540
```

```
gct att gag caa gat gcg aaa gcc gcg cca gat gtt cag ctg ctg atg      1680
Ala Ile Glu Gln Asp Ala Lys Ala Ala Pro Asp Val Gln Leu Leu Met
545                 550                 555                 560 aat gat tct cag aat gac cag tcc aag cag aac gat cag atc gac gta      1728
Asn Asp Ser Gln Asn Asp Gln Ser Lys Gln Asn Asp Gln Ile Asp Val
            565                 570                 575 ttg ctg gcg aaa ggg gtg aag gca ctg gca atc aac ctg gtt gac ccg      1776
Leu Leu Ala Lys Gly Val Lys Ala Leu Ala Ile Asn Leu Val Asp Pro
        580                 585                 590 gca gct gcg ggt acg gtg att gag aaa gcg cgt ggg caa aac gtg ccg      1824
Ala Ala Ala Gly Thr Val Ile Glu Lys Ala Arg Gly Gln Asn Val Pro
    595                 600                 605 gtg gtt ttc ttc aac aaa gaa ccg tct cgt aag gcg ctg gat agc tac      1872
Val Val Phe Phe Asn Lys Glu Pro Ser Arg Lys Ala Leu Asp Ser Tyr
610                 615                 620 gac aaa gcc tac tac gtt ggc act gac tcc aaa gag tcc ggc att att      1920
Asp Lys Ala Tyr Tyr Val Gly Thr Asp Ser Lys Glu Ser Gly Ile Ile
625                 630                 635                 640 caa ggc gat ttg att gct aaa cac tgg gcg gcg aat cag ggt tgg gat      1968
Gln Gly Asp Leu Ile Ala Lys His Trp Ala Ala Asn Gln Gly Trp Asp
            645                 650                 655 ctg aac aaa gac ggt cag att cag ttc gta ctg ctg aaa ggt gaa ccg      2016
Leu Asn Lys Asp Gly Gln Ile Gln Phe Val Leu Leu Lys Gly Glu Pro
        660                 665                 670 ggc cat ccg gat gca gaa gca cgt acc act tac gtg att aaa gaa ttg      2064
Gly His Pro Asp Ala Glu Ala Arg Thr Thr Tyr Val Ile Lys Glu Leu
    675                 680                 685 aac gat aaa ggc atc aaa act gaa cag tta cag tta gat acc gca atg      2112
Asn Asp Lys Gly Ile Lys Thr Glu Gln Leu Gln Leu Asp Thr Ala Met
690                 695                 700 tgg gac acc gct cag gcg aaa gat aag atg gac gcc tgg ctg tct ggc      2160
Trp Asp Thr Ala Gln Ala Lys Asp Lys Met Asp Ala Trp Leu Ser Gly
705                 710                 715                 720 ccg aac gcc aac aaa atc gaa gtg gtt atc gcc aac aac gat gcg atg      2208
Pro Asn Ala Asn Lys Ile Glu Val Val Ile Ala Asn Asn Asp Ala Met
            725                 730                 735 gca atg ggc gcg gtt gaa gcg ctg aaa gca cac aac aag tcc agc att      2256
Ala Met Gly Ala Val Glu Ala Leu Lys Ala His Asn Lys Ser Ser Ile
        740                 745                 750 ccg gtg ttt ggc gtc gat gcg ctg cca gaa gcg ctg gcg ctg gtg aaa      2304
Pro Val Phe Gly Val Asp Ala Leu Pro Glu Ala Leu Ala Leu Val Lys
    755                 760                 765 tcc ggt gca ctg gcg ggc acc gta ctg aac gat gct aac aac cag gcg      2352
Ser Gly Ala Leu Ala Gly Thr Val Leu Asn Asp Ala Asn Asn Gln Ala
770                 775                 780 aaa gcg acc ttt gat ctg gcg aaa aac ctg gcc gat ggt aaa ggt gcg      2400
Lys Ala Thr Phe Asp Leu Ala Lys Asn Leu Ala Asp Gly Lys Gly Ala
785                 790                 795                 800 gct gat ggc acc aac tgg aaa atc gac aac aaa gtg gtc cgc gta cct      2448
Ala Asp Gly Thr Asn Trp Lys Ile Asp Asn Lys Val Val Arg Val Pro
            805                 810                 815 tat gtt ggc gta gat aaa gac aac ctg gct gaa ttc agc aag aaa taa      2496
Tyr Val Gly Val Asp Lys Asp Asn Leu Ala Glu Phe Ser Lys Lys
        820                 825                 830

<210> SEQ ID NO 20
<211> LENGTH: 831
<212> TYPE: PRT
<213> ORGANISM: Artificial Sequence
<220> FEATURE:
<223> OTHER INFORMATION: FLIP-YFP-mglBF16A-Y12S-CFP-D13R Vector
```

<400> SEQUENCE: 20

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Met Val Ser Lys Gly Glu Glu Leu Phe Thr Gly Val Val
            35                  40                  45

Pro Ile Leu Val Glu Leu Asp Gly Asp Val Asn Gly His Lys Phe Ser
50                  55                  60

Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Trp Gly Val Gln Cys Phe Ser Arg Tyr Pro Asp
            100                 105                 110

His Met Lys Gln His Asp Phe Phe Lys Ser Ala Met Pro Glu Gly Tyr
        115                 120                 125

Val Gln Glu Arg Thr Ile Phe Phe Lys Asp Asp Gly Asn Tyr Lys Thr
130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Ile Ser His Asn Val Tyr Ile Thr Ala Asp Lys
            180                 185                 190

Gln Lys Asn Gly Ile Lys Ala Asn Phe Lys Ile Arg His Asn Ile Glu
        195                 200                 205

Asp Gly Ser Val Gln Leu Ala Asp His Tyr Gln Gln Asn Thr Pro Ile
210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
            260                 265                 270

Tyr Lys Gly Gly Thr Gly Gly Ala Asp Thr Arg Ile Gly Val Thr
        275                 280                 285

Ile Tyr Lys Ser Ala Gly Met Val Ser Lys Gly Glu Glu Leu Phe Thr
290                 295                 300

Gly Val Val Pro Ile Leu Val Glu Leu Asp Gly Asp Val Asn Gly His
305                 310                 315                 320

Lys Phe Ser Val Ser Gly Glu Gly Glu Gly Asp Ala Thr Tyr Gly Lys
                325                 330                 335

Leu Thr Leu Lys Phe Ile Cys Thr Thr Gly Lys Leu Pro Val Pro Trp
            340                 345                 350

Pro Thr Leu Val Thr Thr Leu Thr Trp Gly Val Gln Cys Phe Ser Arg
        355                 360                 365

Tyr Pro Asp His Met Lys Gln His Asp Phe Phe Lys Ser Ala Met Pro
370                 375                 380

Glu Gly Tyr Val Gln Glu Arg Thr Ile Phe Phe Lys Asp Asp Gly Asn
385                 390                 395                 400

Tyr Lys Thr Arg Ala Glu Val Lys Phe Glu Gly Asp Thr Leu Val Asn
                405                 410                 415

-continued

Arg Ile Glu Leu Lys Gly Ile Asp Phe Lys Glu Asp Gly Asn Ile Leu
                420                 425                 430

Gly His Lys Leu Glu Tyr Asn Tyr Ile Ser His Asn Val Tyr Ile Thr
            435                 440                 445

Ala Asp Lys Gln Lys Asn Gly Ile Lys Ala Asn Phe Lys Ile Arg His
450                 455                 460

Asn Ile Glu Asp Gly Ser Val Gln Leu Ala Asp His Tyr Gln Gln Asn
465                 470                 475                 480

Thr Pro Ile Gly Asp Gly Pro Val Leu Leu Pro Asp Asn His Tyr Leu
                485                 490                 495

Ser Thr Gln Ser Ala Leu Ser Lys Asp Pro Asn Glu Lys Arg Asp His
            500                 505                 510

Met Val Leu Leu Glu Phe Val Thr Ala Ala Gly Ile Thr Leu Gly Met
        515                 520                 525

Asp Glu Leu Tyr Gly Ser Arg Asp Asn Ala Met Ser Val Val Arg Lys
    530                 535                 540

Ala Ile Glu Gln Asp Ala Lys Ala Ala Pro Asp Val Gln Leu Leu Met
545                 550                 555                 560

Asn Asp Ser Gln Asn Asp Gln Ser Lys Gln Asn Asp Gln Ile Asp Val
                565                 570                 575

Leu Leu Ala Lys Gly Val Lys Ala Leu Ala Ile Asn Leu Val Asp Pro
            580                 585                 590

Ala Ala Ala Gly Thr Val Ile Glu Lys Ala Arg Gly Gln Asn Val Pro
        595                 600                 605

Val Val Phe Phe Asn Lys Glu Pro Ser Arg Lys Ala Leu Asp Ser Tyr
    610                 615                 620

Asp Lys Ala Tyr Tyr Val Gly Thr Asp Ser Lys Glu Ser Gly Ile Ile
625                 630                 635                 640

Gln Gly Asp Leu Ile Ala Lys His Trp Ala Ala Asn Gln Gly Trp Asp
                645                 650                 655

Leu Asn Lys Asp Gly Gln Ile Gln Phe Val Leu Leu Lys Gly Glu Pro
            660                 665                 670

Gly His Pro Asp Ala Glu Ala Arg Thr Thr Tyr Val Ile Lys Glu Leu
        675                 680                 685

Asn Asp Lys Gly Ile Lys Thr Glu Gln Leu Gln Leu Asp Thr Ala Met
    690                 695                 700

Trp Asp Thr Ala Gln Ala Lys Asp Lys Met Asp Ala Trp Leu Ser Gly
705                 710                 715                 720

Pro Asn Ala Asn Lys Ile Glu Val Val Ile Ala Asn Asn Asp Ala Met
                725                 730                 735

Ala Met Gly Ala Val Glu Ala Leu Lys Ala His Asn Lys Ser Ser Ile
            740                 745                 750

Pro Val Phe Gly Val Asp Ala Leu Pro Glu Ala Leu Ala Leu Val Lys
        755                 760                 765

Ser Gly Ala Leu Ala Gly Thr Val Leu Asn Asp Ala Asn Asn Gln Ala
    770                 775                 780

Lys Ala Thr Phe Asp Leu Ala Lys Asn Leu Ala Asp Gly Lys Gly Ala
785                 790                 795                 800

Ala Asp Gly Thr Asn Trp Lys Ile Asp Asn Lys Val Val Arg Val Pro
                805                 810                 815

Tyr Val Gly Val Asp Lys Asp Asn Leu Ala Glu Phe Ser Lys Lys
            820                 825                 830

<210> SEQ ID NO 21

```
<211> LENGTH: 2496
<212> TYPE: DNA
<213> ORGANISM: Artificial Sequence
<220> FEATURE:
<223> OTHER INFORMATION: FLIP-YFP-mglBF16A-P32S-CFP-D33R Vector
<220> FEATURE:
<221> NAME/KEY: CDS
<222> LOCATION: (1)..(2496)

<400> SEQUENCE: 21
```

| | | | | | | | | | | | | | | | | |
|---|---|---|---|---|---|---|---|---|---|---|---|---|---|---|---|---|
| atg | cgg | ggt | tct | cat | cat | cat | cat | cat | cat | ggt | atg | gct | agc | atg | act | 48 |
| Met | Arg | Gly | Ser | His | His | His | His | His | His | Gly | Met | Ala | Ser | Met | Thr | |
| 1 | | | | 5 | | | | | 10 | | | | | 15 | | |
| ggt | gga | cag | caa | atg | ggt | cgg | gat | ctg | tac | gac | gat | gac | gat | aag | gat | 96 |
| Gly | Gly | Gln | Gln | Met | Gly | Arg | Asp | Leu | Tyr | Asp | Asp | Asp | Asp | Lys | Asp | |
| | | 20 | | | | | 25 | | | | | 30 | | | | |
| ccg | ggc | cgc | atg | gtg | agc | aag | ggc | gag | gag | ctg | ttc | acc | ggg | gtg | gtg | 144 |
| Pro | Gly | Arg | Met | Val | Ser | Lys | Gly | Glu | Glu | Leu | Phe | Thr | Gly | Val | Val | |
| | 35 | | | | | 40 | | | | | 45 | | | | | |
| ccc | atc | ctg | gtc | gag | ctg | gac | ggc | gac | gta | aac | ggc | cac | aag | ttc | agc | 192 |
| Pro | Ile | Leu | Val | Glu | Leu | Asp | Gly | Asp | Val | Asn | Gly | His | Lys | Phe | Ser | |
| 50 | | | | | 55 | | | | | 60 | | | | | | |
| gtg | tcc | ggc | gag | ggc | gag | ggc | gat | gcc | acc | tac | ggc | aag | ctg | acc | ctg | 240 |
| Val | Ser | Gly | Glu | Gly | Glu | Gly | Asp | Ala | Thr | Tyr | Gly | Lys | Leu | Thr | Leu | |
| 65 | | | | 70 | | | | | 75 | | | | | 80 | | |
| aag | ttc | atc | tgc | acc | acc | ggc | aag | ctg | ccc | gtg | ccc | tgg | ccc | acc | ctc | 288 |
| Lys | Phe | Ile | Cys | Thr | Thr | Gly | Lys | Leu | Pro | Val | Pro | Trp | Pro | Thr | Leu | |
| | | | 85 | | | | | 90 | | | | | 95 | | | |
| gtg | acc | acc | ctg | acc | tgg | ggc | gtg | cag | tgc | ttc | agc | cgc | tac | ccc | gac | 336 |
| Val | Thr | Thr | Leu | Thr | Trp | Gly | Val | Gln | Cys | Phe | Ser | Arg | Tyr | Pro | Asp | |
| | | 100 | | | | | 105 | | | | | 110 | | | | |
| cac | atg | aag | cag | cac | gac | ttc | ttc | aag | tcc | gcc | atg | ccc | gaa | ggc | tac | 384 |
| His | Met | Lys | Gln | His | Asp | Phe | Phe | Lys | Ser | Ala | Met | Pro | Glu | Gly | Tyr | |
| | 115 | | | | | 120 | | | | | 125 | | | | | |
| gtc | cag | gag | cgc | acc | atc | ttc | ttc | aag | gac | gac | ggc | aac | tac | aag | acc | 432 |
| Val | Gln | Glu | Arg | Thr | Ile | Phe | Phe | Lys | Asp | Asp | Gly | Asn | Tyr | Lys | Thr | |
| 130 | | | | | 135 | | | | | 140 | | | | | | |
| cgc | gcc | gag | gtg | aag | ttc | gag | ggc | gac | acc | ctg | gtg | aac | cgc | atc | gag | 480 |
| Arg | Ala | Glu | Val | Lys | Phe | Glu | Gly | Asp | Thr | Leu | Val | Asn | Arg | Ile | Glu | |
| 145 | | | | | 150 | | | | | 155 | | | | | 160 | |
| ctg | aag | ggc | atc | gac | ttc | aag | gag | gac | ggc | aac | atc | ctg | ggg | cac | aag | 528 |
| Leu | Lys | Gly | Ile | Asp | Phe | Lys | Glu | Asp | Gly | Asn | Ile | Leu | Gly | His | Lys | |
| | | | 165 | | | | | 170 | | | | | 175 | | | |
| ctg | gag | tac | aac | tac | atc | agc | cac | aac | gtc | tat | atc | acc | gcc | gac | aag | 576 |
| Leu | Glu | Tyr | Asn | Tyr | Ile | Ser | His | Asn | Val | Tyr | Ile | Thr | Ala | Asp | Lys | |
| | | 180 | | | | | 185 | | | | | 190 | | | | |
| cag | aag | aac | ggc | atc | aag | gcc | aac | ttc | aag | atc | cgc | cac | aac | atc | gag | 624 |
| Gln | Lys | Asn | Gly | Ile | Lys | Ala | Asn | Phe | Lys | Ile | Arg | His | Asn | Ile | Glu | |
| | 195 | | | | | 200 | | | | | 205 | | | | | |
| gac | ggc | agc | gtg | cag | ctc | gcc | gac | cac | tac | cag | cag | aac | acc | ccc | atc | 672 |
| Asp | Gly | Ser | Val | Gln | Leu | Ala | Asp | His | Tyr | Gln | Gln | Asn | Thr | Pro | Ile | |
| 210 | | | | | 215 | | | | | 220 | | | | | | |
| ggc | gac | ggc | ccc | gtg | ctg | ctg | ccc | gac | aac | cac | tac | ctg | agc | acc | cag | 720 |
| Gly | Asp | Gly | Pro | Val | Leu | Leu | Pro | Asp | Asn | His | Tyr | Leu | Ser | Thr | Gln | |
| 225 | | | | | 230 | | | | | 235 | | | | | 240 | |
| tcc | gcc | ctg | agc | aaa | gac | ccc | aac | gag | aag | cgc | gat | cac | atg | gtc | ctg | 768 |
| Ser | Ala | Leu | Ser | Lys | Asp | Pro | Asn | Glu | Lys | Arg | Asp | His | Met | Val | Leu | |
| | | | 245 | | | | | 250 | | | | | 255 | | | |
| ctg | gag | ttc | gtg | acc | gcc | gcc | ggg | atc | act | ctc | ggc | atg | gac | gag | ctg | 816 |
| Leu | Glu | Phe | Val | Thr | Ala | Ala | Gly | Ile | Thr | Leu | Gly | Met | Asp | Glu | Leu | |
| | | 260 | | | | | 265 | | | | | 270 | | | | |
| tac | aag | ggt | ggt | acc | gga | ggc | gcc | gct | gat | act | cgc | att | ggt | gta | aca | 864 |

-continued

```
              Tyr Lys Gly Gly Thr Gly Gly Ala Ala Asp Thr Arg Ile Gly Val Thr
                      275                 280                 285 atc tat aag tac gac gat aac gcg atg tct gta gtg cgc aag gct att      912
Ile Tyr Lys Tyr Asp Asp Asn Ala Met Ser Val Val Arg Lys Ala Ile
            290                 295                 300 gag caa gat gcg aaa gcc gcg tcg gct ggt atg gtg agc aag ggc gag      960
Glu Gln Asp Ala Lys Ala Ala Ser Ala Gly Met Val Ser Lys Gly Glu
305                 310                 315                 320 gag ctg ttc acc ggg gtg gtg ccc atc ctg gtc gag ctg gac ggc gac     1008
Glu Leu Phe Thr Gly Val Val Pro Ile Leu Val Glu Leu Asp Gly Asp
                325                 330                 335 gta aac ggc cac aag ttc agc gtg tcc ggc gag ggc gag ggc gat gcc     1056
Val Asn Gly His Lys Phe Ser Val Ser Gly Glu Gly Glu Gly Asp Ala
            340                 345                 350 acc tac ggc aag ctg acc ctg aag ttc atc tgc acc acc ggc aag ctg     1104
Thr Tyr Gly Lys Leu Thr Leu Lys Phe Ile Cys Thr Thr Gly Lys Leu
        355                 360                 365 ccc gtg ccc tgg ccc acc ctc gtg acc acc ctg acc tgg ggc gtg cag     1152
Pro Val Pro Trp Pro Thr Leu Val Thr Thr Leu Thr Trp Gly Val Gln
370                 375                 380 tgc ttc agc cgc tac ccc gac cac atg aag cag cac gac ttc ttc aag     1200
Cys Phe Ser Arg Tyr Pro Asp His Met Lys Gln His Asp Phe Phe Lys
385                 390                 395                 400 tcc gcc atg ccc gaa ggc tac gtc cag gag cgc acc atc ttc ttc aag     1248
Ser Ala Met Pro Glu Gly Tyr Val Gln Glu Arg Thr Ile Phe Phe Lys
                405                 410                 415 gac gac ggc aac tac aag acc cgc gcc gag gtg aag ttc gag ggc gac     1296
Asp Asp Gly Asn Tyr Lys Thr Arg Ala Glu Val Lys Phe Glu Gly Asp
            420                 425                 430 acc ctg gtg aac cgc atc gag ctg aag ggc atc gac ttc aag gag gac     1344
Thr Leu Val Asn Arg Ile Glu Leu Lys Gly Ile Asp Phe Lys Glu Asp
        435                 440                 445 ggc aac atc ctg ggg cac aag ctg gag tac aac tac atc agc cac aac     1392
Gly Asn Ile Leu Gly His Lys Leu Glu Tyr Asn Tyr Ile Ser His Asn
450                 455                 460 gtc tat atc acc gcc gac aag cag aag aac ggc atc aag gcc aac ttc     1440
Val Tyr Ile Thr Ala Asp Lys Gln Lys Asn Gly Ile Lys Ala Asn Phe
465                 470                 475                 480 aag atc cgc cac aac atc gag gac ggc agc gtg cag ctc gcc gac cac     1488
Lys Ile Arg His Asn Ile Glu Asp Gly Ser Val Gln Leu Ala Asp His
                485                 490                 495 tac cag cag aac acc ccc atc ggc gac ggc ccc gtg ctg ctg ccc gac     1536
Tyr Gln Gln Asn Thr Pro Ile Gly Asp Gly Pro Val Leu Leu Pro Asp
            500                 505                 510 aac cac tac ctg agc acc cag tcc gcc ctg agc aaa gac ccc aac gag     1584
Asn His Tyr Leu Ser Thr Gln Ser Ala Leu Ser Lys Asp Pro Asn Glu
        515                 520                 525 aag cgc gat cac atg gtc ctg ctg gag ttc gtg acc gcc gcc ggg atc     1632
Lys Arg Asp His Met Val Leu Leu Glu Phe Val Thr Ala Ala Gly Ile
530                 535                 540 act ctc ggc atg gac gag ctg tac ggt agc cga gtt cag ctg ctg atg     1680
Thr Leu Gly Met Asp Glu Leu Tyr Gly Ser Arg Val Gln Leu Leu Met
545                 550                 555                 560 aat gat tct cag aat gac cag tcc aag cag aac gat cag atc gac gta     1728
Asn Asp Ser Gln Asn Asp Gln Ser Lys Gln Asn Asp Gln Ile Asp Val
                565                 570                 575 ttg ctg gcg aaa ggg gtg aag gca ctg gca atc aac ctg gtt gac ccg     1776
Leu Leu Ala Lys Gly Val Lys Ala Leu Ala Ile Asn Leu Val Asp Pro
            580                 585                 590 gca gct gcg ggt acg gtg att gag aaa gcg cgt ggg caa aac gtg ccg     1824
Ala Ala Ala Gly Thr Val Ile Glu Lys Ala Arg Gly Gln Asn Val Pro
```

```
Ala Ala Ala Gly Thr Val Ile Glu Lys Ala Arg Gly Gln Asn Val Pro
        595                 600                 605 gtg gtt ttc ttc aac aaa gaa ccg tct cgt aag gcg ctg gat agc tac   1872
Val Val Phe Phe Asn Lys Glu Pro Ser Arg Lys Ala Leu Asp Ser Tyr
610                 615                 620 gac aaa gcc tac tac gtt ggc act gac tcc aaa gag tcc ggc att att   1920
Asp Lys Ala Tyr Tyr Val Gly Thr Asp Ser Lys Glu Ser Gly Ile Ile
625                 630                 635                 640 caa ggc gat ttg att gct aaa cac tgg gcg gcg aat cag ggt tgg gat   1968
Gln Gly Asp Leu Ile Ala Lys His Trp Ala Ala Asn Gln Gly Trp Asp
                645                 650                 655 ctg aac aaa gac ggt cag att cag ttc gta ctg aaa ggt gaa ccg       2016
Leu Asn Lys Asp Gly Gln Ile Gln Phe Val Leu Lys Gly Glu Pro
            660                 665                 670 ggc cat ccg gat gca gaa gca cgt acc act tac gtg att aaa gaa ttg   2064
Gly His Pro Asp Ala Glu Ala Arg Thr Thr Tyr Val Ile Lys Glu Leu
        675                 680                 685 aac gat aaa ggc atc aaa act gaa cag tta cag tta gat acc gca atg   2112
Asn Asp Lys Gly Ile Lys Thr Glu Gln Leu Gln Leu Asp Thr Ala Met
690                 695                 700 tgg gac acc gct cag gcg aaa gat aag atg gac gcc tgg ctg tct ggc   2160
Trp Asp Thr Ala Gln Ala Lys Asp Lys Met Asp Ala Trp Leu Ser Gly
705                 710                 715                 720 ccg aac gcc aac aaa atc gaa gtg gtt atc gcc aac aac gat gcg atg   2208
Pro Asn Ala Asn Lys Ile Glu Val Val Ile Ala Asn Asn Asp Ala Met
                725                 730                 735 gca atg ggc gcg gtt gaa gcg ctg aaa gca cac aac aag tcc agc att   2256
Ala Met Gly Ala Val Glu Ala Leu Lys Ala His Asn Lys Ser Ser Ile
            740                 745                 750 ccg gtg ttt ggc gtc gat gcg ctg cca gaa gcg ctg gcg ctg gtg aaa   2304
Pro Val Phe Gly Val Asp Ala Leu Pro Glu Ala Leu Ala Leu Val Lys
        755                 760                 765 tcc ggt gca ctg gcg ggc acc gta ctg aac gat gct aac aac cag gcg   2352
Ser Gly Ala Leu Ala Gly Thr Val Leu Asn Asp Ala Asn Asn Gln Ala
770                 775                 780 aaa gcg acc ttt gat ctg gcg aaa aac ctg gcc gat ggt aaa ggt gcg   2400
Lys Ala Thr Phe Asp Leu Ala Lys Asn Leu Ala Asp Gly Lys Gly Ala
785                 790                 795                 800 gct gat ggc acc aac tgg aaa atc gac aac aaa gtg gtc cgc gta cct   2448
Ala Asp Gly Thr Asn Trp Lys Ile Asp Asn Lys Val Val Arg Val Pro
                805                 810                 815 tat gtt ggc gta gat aaa gac aac ctg gct gaa ttc agc aag aaa taa  2496
Tyr Val Gly Val Asp Lys Asp Asn Leu Ala Glu Phe Ser Lys Lys
            820                 825                 830

<210> SEQ ID NO 22
<211> LENGTH: 831
<212> TYPE: PRT
<213> ORGANISM: Artificial Sequence
<220> FEATURE:
<223> OTHER INFORMATION: FLIP-YFP-mglBF16A-P32S-CFP-D33R Vector

<400> SEQUENCE: 22

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Met Val Ser Lys Gly Glu Glu Leu Phe Thr Gly Val Val
        35                  40                  45

Pro Ile Leu Val Glu Leu Asp Gly Asp Val Asn Gly His Lys Phe Ser
    50                  55                  60
```

```
Val Ser Gly Glu Gly Glu Gly Asp Ala Thr Tyr Gly Lys Leu Thr Leu
 65                  70                  75                  80

Lys Phe Ile Cys Thr Thr Gly Lys Leu Pro Val Pro Trp Pro Thr Leu
                 85                  90                  95

Val Thr Thr Leu Thr Trp Gly Val Gln Cys Phe Ser Arg Tyr Pro Asp
            100                 105                 110

His Met Lys Gln His Asp Phe Phe Lys Ser Ala Met Pro Glu Gly Tyr
        115                 120                 125

Val Gln Glu Arg Thr Ile Phe Phe Lys Asp Asp Gly Asn Tyr Lys Thr
130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Ile Ser His Asn Val Tyr Ile Thr Ala Asp Lys
            180                 185                 190

Gln Lys Asn Gly Ile Lys Ala Asn Phe Lys Ile Arg His Asn Ile Glu
        195                 200                 205

Asp Gly Ser Val Gln Leu Ala Asp His Tyr Gln Gln Asn Thr Pro Ile
210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
            260                 265                 270

Tyr Lys Gly Gly Thr Gly Gly Ala Ala Asp Thr Arg Ile Gly Val Thr
        275                 280                 285

Ile Tyr Lys Tyr Asp Asp Asn Ala Met Ser Val Val Arg Lys Ala Ile
290                 295                 300

Glu Gln Asp Ala Lys Ala Ala Ser Ala Gly Met Val Ser Lys Gly Glu
305                 310                 315                 320

Glu Leu Phe Thr Gly Val Val Pro Ile Leu Val Glu Leu Asp Gly Asp
                325                 330                 335

Val Asn Gly His Lys Phe Ser Val Ser Gly Glu Gly Glu Gly Asp Ala
            340                 345                 350

Thr Tyr Gly Lys Leu Thr Leu Lys Phe Ile Cys Thr Thr Gly Lys Leu
        355                 360                 365

Pro Val Pro Trp Pro Thr Leu Val Thr Thr Leu Thr Trp Gly Val Gln
370                 375                 380

Cys Phe Ser Arg Tyr Pro Asp His Met Lys Gln His Asp Phe Phe Lys
385                 390                 395                 400

Ser Ala Met Pro Glu Gly Tyr Val Gln Glu Arg Thr Ile Phe Phe Lys
                405                 410                 415

Asp Asp Gly Asn Tyr Lys Thr Arg Ala Glu Val Lys Phe Glu Gly Asp
            420                 425                 430

Thr Leu Val Asn Arg Ile Glu Leu Lys Gly Ile Asp Phe Lys Glu Asp
        435                 440                 445

Gly Asn Ile Leu Gly His Lys Leu Glu Tyr Asn Tyr Ile Ser His Asn
450                 455                 460

Val Tyr Ile Thr Ala Asp Lys Gln Lys Asn Gly Ile Lys Ala Asn Phe
465                 470                 475                 480

Lys Ile Arg His Asn Ile Glu Asp Gly Ser Val Gln Leu Ala Asp His
```

-continued

Tyr Gln Gln Asn Thr Pro Ile Gly Asp Gly Pro Val Leu Leu Pro Asp
            485                 490                 495
                500                 505                 510

Asn His Tyr Leu Ser Thr Gln Ser Ala Leu Ser Lys Asp Pro Asn Glu
            515                 520                 525

Lys Arg Asp His Met Val Leu Leu Glu Phe Val Thr Ala Ala Gly Ile
            530                 535                 540

Thr Leu Gly Met Asp Glu Leu Tyr Gly Ser Arg Val Gln Leu Leu Met
545                 550                 555                 560

Asn Asp Ser Gln Asn Asp Gln Ser Lys Gln Asn Asp Gln Ile Asp Val
            565                 570                 575

Leu Leu Ala Lys Gly Val Lys Ala Leu Ala Ile Asn Leu Val Asp Pro
            580                 585                 590

Ala Ala Ala Gly Thr Val Ile Glu Lys Ala Arg Gly Gln Asn Val Pro
            595                 600                 605

Val Val Phe Phe Asn Lys Glu Pro Ser Arg Lys Ala Leu Asp Ser Tyr
            610                 615                 620

Asp Lys Ala Tyr Tyr Val Gly Thr Asp Ser Lys Glu Ser Gly Ile Ile
625                 630                 635                 640

Gln Gly Asp Leu Ile Ala Lys His Trp Ala Ala Asn Gln Gly Trp Asp
            645                 650                 655

Leu Asn Lys Asp Gly Gln Ile Gln Phe Val Leu Leu Lys Gly Glu Pro
            660                 665                 670

Gly His Pro Asp Ala Glu Ala Arg Thr Thr Tyr Val Ile Lys Glu Leu
            675                 680                 685

Asn Asp Lys Gly Ile Lys Thr Glu Gln Leu Gln Leu Asp Thr Ala Met
            690                 695                 700

Trp Asp Thr Ala Gln Ala Lys Asp Lys Met Asp Ala Trp Leu Ser Gly
705                 710                 715                 720

Pro Asn Ala Asn Lys Ile Glu Val Val Ile Ala Asn Asn Asp Ala Met
            725                 730                 735

Ala Met Gly Ala Val Glu Ala Leu Lys Ala His Asn Lys Ser Ser Ile
            740                 745                 750

Pro Val Phe Gly Val Asp Ala Leu Pro Glu Ala Leu Ala Leu Val Lys
            755                 760                 765

Ser Gly Ala Leu Ala Gly Thr Val Leu Asn Asp Ala Asn Asn Gln Ala
            770                 775                 780

Lys Ala Thr Phe Asp Leu Ala Lys Asn Leu Ala Asp Gly Lys Gly Ala
785                 790                 795                 800

Ala Asp Gly Thr Asn Trp Lys Ile Asp Asn Lys Val Val Arg Val Pro
            805                 810                 815

Tyr Val Gly Val Asp Lys Asp Asn Leu Ala Glu Phe Ser Lys Lys
            820                 825                 830

<210> SEQ ID NO 23
<211> LENGTH: 2496
<212> TYPE: DNA
<213> ORGANISM: Artificial Sequence
<220> FEATURE:
<223> OTHER INFORMATION: FLIP-YFP-mglBF16A-G275S-CFP-K276R Vector
<220> FEATURE:
<221> NAME/KEY: CDS
<222> LOCATION: (1)..(2496)

<400> SEQUENCE: 23 atg cgg ggt tct cat cat cat cat cat cat ggt atg gct agc atg act         48
Met Arg Gly Ser His His His His His His Gly Met Ala Ser Met Thr -continued

```
1               5                   10                  15 ggt gga cag caa atg ggt cgg gat ctg tac gac gat gac gat aag gat       96
Gly Gly Gln Gln Met Gly Arg Asp Leu Tyr Asp Asp Asp Asp Lys Asp
                    20                  25                  30 ccg ggc cgc atg gtg agc aag ggc gag gag ctg ttc acc ggg gtg gtg      144
Pro Gly Arg Met Val Ser Lys Gly Glu Glu Leu Phe Thr Gly Val Val
                35                  40                  45 ccc atc ctg gtc gag ctg gac ggc gac gta aac ggc cac aag ttc agc      192
Pro Ile Leu Val Glu Leu Asp Gly Asp Val Asn Gly His Lys Phe Ser
 50                  55                  60 gtg tcc ggc gag ggc gag ggc gat gcc acc tac ggc aag ctg acc ctg      240
Val Ser Gly Glu Gly Glu Gly Asp Ala Thr Tyr Gly Lys Leu Thr Leu
 65                  70                  75                  80 aag ttc atc tgc acc acc ggc aag ctg ccc gtg ccc tgg ccc acc ctc      288
Lys Phe Ile Cys Thr Thr Gly Lys Leu Pro Val Pro Trp Pro Thr Leu
                    85                  90                  95 gtg acc acc ctg acc tgg ggc gtg cag tgc ttc agc cgc tac ccc gac      336
Val Thr Thr Leu Thr Trp Gly Val Gln Cys Phe Ser Arg Tyr Pro Asp
                    100                 105                 110 cac atg aag cag cac gac ttc ttc aag tcc gcc atg ccc gaa ggc tac      384
His Met Lys Gln His Asp Phe Phe Lys Ser Ala Met Pro Glu Gly Tyr
                    115                 120                 125 gtc cag gag cgc acc atc ttc ttc aag gac gac ggc aac tac aag acc      432
Val Gln Glu Arg Thr Ile Phe Phe Lys Asp Asp Gly Asn Tyr Lys Thr
                130                 135                 140 cgc gcc gag gtg aag ttc gag ggc gac acc ctg gtg aac cgc atc gag      480
Arg Ala Glu Val Lys Phe Glu Gly Asp Thr Leu Val Asn Arg Ile Glu
145                 150                 155                 160 ctg aag ggc atc gac ttc aag gag gac ggc aac atc ctg ggg cac aag      528
Leu Lys Gly Ile Asp Phe Lys Glu Asp Gly Asn Ile Leu Gly His Lys
                    165                 170                 175 ctg gag tac aac tac atc agc cac aac gtc tat atc acc gcc gac aag      576
Leu Glu Tyr Asn Tyr Ile Ser His Asn Val Tyr Ile Thr Ala Asp Lys
                180                 185                 190 cag aag aac ggc atc aag gcc aac ttc aag atc cgc cac aac atc gag      624
Gln Lys Asn Gly Ile Lys Ala Asn Phe Lys Ile Arg His Asn Ile Glu
                    195                 200                 205 gac ggc agc gtg cag ctc gcc gac cac tac cag cag aac acc ccc atc      672
Asp Gly Ser Val Gln Leu Ala Asp His Tyr Gln Gln Asn Thr Pro Ile
    210                 215                 220 ggc gac ggc ccc gtg ctg ctg ccc gac aac cac tac ctg agc acc cag      720
Gly Asp Gly Pro Val Leu Leu Pro Asp Asn His Tyr Leu Ser Thr Gln
225                 230                 235                 240 tcc gcc ctg agc aaa gac ccc aac gag aag cgc gat cac atg gtc ctg      768
Ser Ala Leu Ser Lys Asp Pro Asn Glu Lys Arg Asp His Met Val Leu
                    245                 250                 255 ctg gag ttc gtg acc gcc gcc ggg atc act ctc ggc atg gac gag ctg      816
Leu Glu Phe Val Thr Ala Ala Gly Ile Thr Leu Gly Met Asp Glu Leu
                260                 265                 270 tac aag ggt ggt acc gga ggc gcc gct gat act cgc att ggt gta aca      864
Tyr Lys Gly Gly Thr Gly Gly Ala Ala Asp Thr Arg Ile Gly Val Thr
                    275                 280                 285 atc tat aag tac gac gat aac gcg atg tct gta gtg cgc aag gct att      912
Ile Tyr Lys Tyr Asp Asp Asn Ala Met Ser Val Val Arg Lys Ala Ile
                290                 295                 300 gag caa gat gcg aaa gcc gcg cca gat gtt cag ctg ctg atg aat gat      960
Glu Gln Asp Ala Lys Ala Ala Pro Asp Val Gln Leu Leu Met Asn Asp
305                 310                 315                 320 tct cag aat gac cag tcc aag cag aac gat cag atc gac gta ttg ctg     1008
Ser Gln Asn Asp Gln Ser Lys Gln Asn Asp Gln Ile Asp Val Leu Leu
```

```
                    325                 330                 335
gcg aaa ggg gtg aag gca ctg gca atc aac ctg gtt gac ccg gca gct     1056
Ala Lys Gly Val Lys Ala Leu Ala Ile Asn Leu Val Asp Pro Ala Ala
            340                 345                 350 gcg ggt acg gtt att gag aaa gcg cgt ggg caa aac gtg ccg gtg gtt     1104
Ala Gly Thr Val Ile Glu Lys Ala Arg Gly Gln Asn Val Pro Val Val
        355                 360                 365 ttc ttc aac aaa gaa ccg tct cgt aag gcg ctg gat agc tac gac aaa     1152
Phe Phe Asn Lys Glu Pro Ser Arg Lys Ala Leu Asp Ser Tyr Asp Lys
370                 375                 380 gcc tac tac gtt ggc act gac tcc aaa gag tcc ggc att att caa ggc     1200
Ala Tyr Tyr Val Gly Thr Asp Ser Lys Glu Ser Gly Ile Ile Gln Gly
385                 390                 395                 400 gat ttg att gct aaa cac tgg gcg gcg aat cag ggt tgg gat ctg aac     1248
Asp Leu Ile Ala Lys His Trp Ala Ala Asn Gln Gly Trp Asp Leu Asn
                405                 410                 415 aaa gac ggt cag att cag ttc gta ctg ctg aaa ggt gaa ccg ggc cat     1296
Lys Asp Gly Gln Ile Gln Phe Val Leu Leu Lys Gly Glu Pro Gly His
            420                 425                 430 ccg gat gca gaa gca cgt acc act tac gtg att aaa gaa ttg aac gat     1344
Pro Asp Ala Glu Ala Arg Thr Thr Tyr Val Ile Lys Glu Leu Asn Asp
        435                 440                 445 aaa ggc atc aaa act gaa cag tta cag tta gat acc gca atg tgg gac     1392
Lys Gly Ile Lys Thr Glu Gln Leu Gln Leu Asp Thr Ala Met Trp Asp
450                 455                 460 acc gct cag gcg aaa gat aag atg gac gcc tgg ctg tct ggc ccg aac     1440
Thr Ala Gln Ala Lys Asp Lys Met Asp Ala Trp Leu Ser Gly Pro Asn
465                 470                 475                 480 gcc aac aaa atc gaa gtg gtt atc gcc aac aac gat gcg atg gca atg     1488
Ala Asn Lys Ile Glu Val Val Ile Ala Asn Asn Asp Ala Met Ala Met
                485                 490                 495 ggc gcg gtt gaa gcg ctg aaa gca cac aac aag tcc agc att ccg gtg     1536
Gly Ala Val Glu Ala Leu Lys Ala His Asn Lys Ser Ser Ile Pro Val
            500                 505                 510 ttt ggc gtc gat gcg ctg cca gaa gcg ctg gcg ctg gtg aaa tcc ggt     1584
Phe Gly Val Asp Ala Leu Pro Glu Ala Leu Ala Leu Val Lys Ser Gly
        515                 520                 525 gca ctg gcg ggc acc gta ctg aac gat gct aac aac cag gcg aaa gcg     1632
Ala Leu Ala Gly Thr Val Leu Asn Asp Ala Asn Asn Gln Ala Lys Ala
530                 535                 540 acc ttt gat ctg gcg aaa aac ctg gcc gat tcg gct ggt atg gtg agc     1680
Thr Phe Asp Leu Ala Lys Asn Leu Ala Asp Ser Ala Gly Met Val Ser
545                 550                 555                 560 aag ggc gag gag ctg ttc acc ggg gtg gtg ccc atc ctg gtc gag ctg     1728
Lys Gly Glu Glu Leu Phe Thr Gly Val Val Pro Ile Leu Val Glu Leu
                565                 570                 575 gac ggc gac gta aac ggc cac aag ttc agc gtg tcc ggc gag ggc gag     1776
Asp Gly Asp Val Asn Gly His Lys Phe Ser Val Ser Gly Glu Gly Glu
            580                 585                 590 ggc gat gcc acc tac ggc aag ctg acc ctg aag ttc atc tgc acc acc     1824
Gly Asp Ala Thr Tyr Gly Lys Leu Thr Leu Lys Phe Ile Cys Thr Thr
        595                 600                 605 ggc aag ctg ccc gtg ccc tgg ccc acc ctc gtg acc acc ctg acc tgg     1872
Gly Lys Leu Pro Val Pro Trp Pro Thr Leu Val Thr Thr Leu Thr Trp
610                 615                 620 ggc gtg cag tgc ttc agc cgc tac ccc gac cac atg aag cag cac gac     1920
Gly Val Gln Cys Phe Ser Arg Tyr Pro Asp His Met Lys Gln His Asp
625                 630                 635                 640 ttc ttc aag tcc gcc atg ccc gaa ggc tac gtc cag gag cgc acc atc     1968
Phe Phe Lys Ser Ala Met Pro Glu Gly Tyr Val Gln Glu Arg Thr Ile
```

```
                        645                     650                     655
ttc ttc aag gac gac ggc aac tac aag acc cgc gcc gag gtg aag ttc     2016
Phe Phe Lys Asp Asp Gly Asn Tyr Lys Thr Arg Ala Glu Val Lys Phe
            660                     665                     670 gag ggc gac acc ctg gtg aac cgc atc gag ctg aag ggc atc gac ttc     2064
Glu Gly Asp Thr Leu Val Asn Arg Ile Glu Leu Lys Gly Ile Asp Phe
            675                     680                     685 aag gag gac ggc aac atc ctg ggg cac aag ctg gag tac aac tac atc     2112
Lys Glu Asp Gly Asn Ile Leu Gly His Lys Leu Glu Tyr Asn Tyr Ile
            690                     695                     700 agc cac aac gtc tat atc acc gcc gac aag cag aag aac ggc atc aag     2160
Ser His Asn Val Tyr Ile Thr Ala Asp Lys Gln Lys Asn Gly Ile Lys
705                     710                     715                 720 gcc aac ttc aag atc cgc cac aac atc gag gac ggc agc gtg cag ctc     2208
Ala Asn Phe Lys Ile Arg His Asn Ile Glu Asp Gly Ser Val Gln Leu
            725                     730                     735 gcc gac cac tac cag cag aac acc ccc atc ggc gac ggc ccc gtg ctg     2256
Ala Asp His Tyr Gln Gln Asn Thr Pro Ile Gly Asp Gly Pro Val Leu
            740                     745                     750 ctg ccc gac aac cac tac ctg agc acc cag tcc gcc ctg agc aaa gac     2304
Leu Pro Asp Asn His Tyr Leu Ser Thr Gln Ser Ala Leu Ser Lys Asp
            755                     760                     765 ccc aac gag aag cgc gat cac atg gtc ctg ctg gag ttc gtg acc gcc     2352
Pro Asn Glu Lys Arg Asp His Met Val Leu Leu Glu Phe Val Thr Ala
            770                     775                     780 gcc ggg atc act ctc ggc atg gac gag ctg tac ggt agc cga ggt gcg     2400
Ala Gly Ile Thr Leu Gly Met Asp Glu Leu Tyr Gly Ser Arg Gly Ala
785                     790                     795                 800 gct gat ggc acc aac tgg aaa atc gac aac aaa gtg tcc cgc gta cct     2448
Ala Asp Gly Thr Asn Trp Lys Ile Asp Asn Lys Val Val Arg Val Pro
            805                     810                     815 tat gtt ggc gta gat aaa gac aac ctg gct gaa ttc agc aag aaa taa    2496
Tyr Val Gly Val Asp Lys Asp Asn Leu Ala Glu Phe Ser Lys Lys
            820                     825                     830
```

<210> SEQ ID NO 24
<211> LENGTH: 831
<212> TYPE: PRT
<213> ORGANISM: Artificial Sequence
<220> FEATURE:
<223> OTHER INFORMATION: FLIP-YFP-mglBF16A-G275S-CFP-K276R Vector

<400> SEQUENCE: 24

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Gly Arg Met Val Ser Lys Gly Glu Glu Leu Phe Thr Gly Val Val
            35                  40                  45

Pro Ile Leu Val Glu Leu Asp Gly Asp Val Asn Gly His Lys Phe Ser
        50                  55                  60

Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Trp Gly Val Gln Cys Phe Ser Arg Tyr Pro Asp
            100                 105                 110

His Met Lys Gln His Asp Phe Phe Lys Ser Ala Met Pro Glu Gly Tyr
        115                 120                 125
```

```
Val Gln Glu Arg Thr Ile Phe Phe Lys Asp Asp Gly Asn Tyr Lys Thr
        130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Ile Ser His Asn Val Tyr Ile Thr Ala Asp Lys
                180                 185                 190

Gln Lys Asn Gly Ile Lys Ala Asn Phe Lys Ile Arg His Asn Ile Glu
        195                 200                 205

Asp Gly Ser Val Gln Leu Ala Asp His Tyr Gln Gln Asn Thr Pro Ile
210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
                260                 265                 270

Tyr Lys Gly Gly Thr Gly Gly Ala Ala Asp Thr Arg Ile Gly Val Thr
        275                 280                 285

Ile Tyr Lys Tyr Asp Asp Asn Ala Met Ser Val Val Arg Lys Ala Ile
290                 295                 300

Glu Gln Asp Ala Lys Ala Ala Pro Asp Val Gln Leu Leu Met Asn Asp
305                 310                 315                 320

Ser Gln Asn Asp Gln Ser Lys Gln Asn Asp Gln Ile Asp Val Leu Leu
                325                 330                 335

Ala Lys Gly Val Lys Ala Leu Ala Ile Asn Leu Val Asp Pro Ala Ala
                340                 345                 350

Ala Gly Thr Val Ile Glu Lys Ala Arg Gly Gln Asn Val Pro Val Val
            355                 360                 365

Phe Phe Asn Lys Glu Pro Ser Arg Lys Ala Leu Asp Ser Tyr Asp Lys
        370                 375                 380

Ala Tyr Tyr Val Gly Thr Asp Ser Lys Glu Ser Gly Ile Ile Gln Gly
385                 390                 395                 400

Asp Leu Ile Ala Lys His Trp Ala Ala Asn Gln Gly Trp Asp Leu Asn
                405                 410                 415

Lys Asp Gly Gln Ile Gln Phe Val Leu Leu Lys Gly Glu Pro Gly His
                420                 425                 430

Pro Asp Ala Glu Ala Arg Thr Thr Tyr Val Ile Lys Glu Leu Asn Asp
            435                 440                 445

Lys Gly Ile Lys Thr Glu Gln Leu Gln Leu Asp Thr Ala Met Trp Asp
        450                 455                 460

Thr Ala Gln Ala Lys Asp Lys Met Asp Ala Trp Leu Ser Gly Pro Asn
465                 470                 475                 480

Ala Asn Lys Ile Glu Val Val Ile Ala Asn Asn Asp Ala Met Ala Met
                485                 490                 495

Gly Ala Val Glu Ala Leu Lys Ala His Asn Lys Ser Ser Ile Pro Val
                500                 505                 510

Phe Gly Val Asp Ala Leu Pro Glu Ala Leu Ala Leu Val Lys Ser Gly
            515                 520                 525

Ala Leu Ala Gly Thr Val Leu Asn Asp Ala Asn Asn Gln Ala Lys Ala
        530                 535                 540

Thr Phe Asp Leu Ala Lys Asn Leu Ala Asp Ser Ala Gly Met Val Ser
545                 550                 555                 560
```

```
Lys Gly Glu Glu Leu Phe Thr Gly Val Val Pro Ile Leu Val Glu Leu
                565                 570                 575

Asp Gly Asp Val Asn Gly His Lys Phe Ser Val Ser Gly Glu Gly Glu
            580                 585                 590

Gly Asp Ala Thr Tyr Gly Lys Leu Thr Leu Lys Phe Ile Cys Thr Thr
        595                 600                 605

Gly Lys Leu Pro Val Pro Trp Pro Thr Leu Val Thr Thr Leu Thr Trp
    610                 615                 620

Gly Val Gln Cys Phe Ser Arg Tyr Pro Asp His Met Lys Gln His Asp
625                 630                 635                 640

Phe Phe Lys Ser Ala Met Pro Glu Gly Tyr Val Gln Glu Arg Thr Ile
                645                 650                 655

Phe Phe Lys Asp Asp Gly Asn Tyr Lys Thr Arg Ala Glu Val Lys Phe
            660                 665                 670

Glu Gly Asp Thr Leu Val Asn Arg Ile Glu Leu Lys Gly Ile Asp Phe
        675                 680                 685

Lys Glu Asp Gly Asn Ile Leu Gly His Lys Leu Glu Tyr Asn Tyr Ile
    690                 695                 700

Ser His Asn Val Tyr Ile Thr Ala Asp Lys Gln Lys Asn Gly Ile Lys
705                 710                 715                 720

Ala Asn Phe Lys Ile Arg His Asn Ile Glu Asp Gly Ser Val Gln Leu
                725                 730                 735

Ala Asp His Tyr Gln Gln Asn Thr Pro Ile Gly Asp Gly Pro Val Leu
            740                 745                 750

Leu Pro Asp Asn His Tyr Leu Ser Thr Gln Ser Ala Leu Ser Lys Asp
        755                 760                 765

Pro Asn Glu Lys Arg Asp His Met Val Leu Leu Glu Phe Val Thr Ala
    770                 775                 780

Ala Gly Ile Thr Leu Gly Met Asp Glu Leu Tyr Gly Ser Arg Gly Ala
785                 790                 795                 800

Ala Asp Gly Thr Asn Trp Lys Ile Asp Asn Lys Val Val Arg Val Pro
                805                 810                 815

Tyr Val Gly Val Asp Lys Asp Asn Leu Ala Glu Phe Ser Lys Lys
            820                 825                 830

<210> SEQ ID NO 25
<211> LENGTH: 2496
<212> TYPE: DNA
<213> ORGANISM: Artificial Sequence
<220> FEATURE:
<223> OTHER INFORMATION: FLIP-YFP-mglBF16A-T282S-CFP-N283R Vector
<220> FEATURE:
<221> NAME/KEY: CDS
<222> LOCATION: (1)..(2496)

<400> SEQUENCE: 25 atg cgg ggt tct cat cat cat cat cat cat ggt atg gct agc atg act    48
Met Arg Gly Ser His His His His His His Gly Met Ala Ser Met Thr
1               5                   10                  15 ggt gga cag caa atg ggt cgg gat ctg tac gac gat gac gat aag gat    96
Gly Gly Gln Gln Met Gly Arg Asp Leu Tyr Asp Asp Asp Asp Lys Asp
            20                  25                  30 ccg ggc cgc atg gtg agc aag ggc gag gag ctg ttc acc ggg gtg gtg   144
Pro Gly Arg Met Val Ser Lys Gly Glu Glu Leu Phe Thr Gly Val Val
        35                  40                  45 ccc atc ctg gtc gag ctg gac ggc gac gta aac ggc cac aag ttc agc   192
Pro Ile Leu Val Glu Leu Asp Gly Asp Val Asn Gly His Lys Phe Ser
    50                  55                  60
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gtg | tcc | ggc | gag | ggc | gag | ggc | gat | gcc | acc | tac | ggc | aag | ctg | acc | ctg | 240  |
| Val | Ser | Gly | Glu | Gly | Glu | Gly | Asp | Ala | Thr | Tyr | Gly | Lys | Leu | Thr | Leu |      |
| 65  |     |     |     | 70  |     |     |     |     | 75  |     |     |     |     | 80  |     |      |
| aag | ttc | atc | tgc | acc | acc | ggc | aag | ctg | ccc | gtg | ccc | tgg | ccc | acc | ctc | 288  |
| Lys | Phe | Ile | Cys | Thr | Thr | Gly | Lys | Leu | Pro | Val | Pro | Trp | Pro | Thr | Leu |      |
|     |     |     |     | 85  |     |     |     |     | 90  |     |     |     |     | 95  |     |      |
| gtg | acc | acc | ctg | acc | tgg | ggc | gtg | cag | tgc | ttc | agc | cgc | tac | ccc | gac | 336  |
| Val | Thr | Thr | Leu | Thr | Trp | Gly | Val | Gln | Cys | Phe | Ser | Arg | Tyr | Pro | Asp |      |
|     |     | 100 |     |     |     |     | 105 |     |     |     |     | 110 |     |     |     |      |
| cac | atg | aag | cag | cac | gac | ttc | ttc | aag | tcc | gcc | atg | ccc | gaa | ggc | tac | 384  |
| His | Met | Lys | Gln | His | Asp | Phe | Phe | Lys | Ser | Ala | Met | Pro | Glu | Gly | Tyr |      |
|     |     |     | 115 |     |     |     |     | 120 |     |     |     |     | 125 |     |     |      |
| gtc | cag | gag | cgc | acc | atc | ttc | ttc | aag | gac | gac | ggc | aac | tac | aag | acc | 432  |
| Val | Gln | Glu | Arg | Thr | Ile | Phe | Phe | Lys | Asp | Asp | Gly | Asn | Tyr | Lys | Thr |      |
|     | 130 |     |     |     |     | 135 |     |     |     |     | 140 |     |     |     |     |      |
| cgc | gcc | gag | gtg | aag | ttc | gag | ggc | gac | acc | ctg | gtg | aac | cgc | atc | gag | 480  |
| Arg | Ala | Glu | Val | Lys | Phe | Glu | Gly | Asp | Thr | Leu | Val | Asn | Arg | Ile | Glu |      |
| 145 |     |     |     |     | 150 |     |     |     |     | 155 |     |     |     |     | 160 |      |
| ctg | aag | ggc | atc | gac | ttc | aag | gag | gac | ggc | aac | atc | ctg | ggg | cac | aag | 528  |
| Leu | Lys | Gly | Ile | Asp | Phe | Lys | Glu | Asp | Gly | Asn | Ile | Leu | Gly | His | Lys |      |
|     |     |     |     | 165 |     |     |     |     | 170 |     |     |     |     | 175 |     |      |
| ctg | gag | tac | aac | tac | atc | agc | cac | aac | gtc | tat | atc | acc | gcc | gac | aag | 576  |
| Leu | Glu | Tyr | Asn | Tyr | Ile | Ser | His | Asn | Val | Tyr | Ile | Thr | Ala | Asp | Lys |      |
|     |     |     | 180 |     |     |     |     | 185 |     |     |     |     | 190 |     |     |      |
| cag | aag | aac | ggc | atc | aag | gcc | aac | ttc | aag | atc | cgc | cac | aac | atc | gag | 624  |
| Gln | Lys | Asn | Gly | Ile | Lys | Ala | Asn | Phe | Lys | Ile | Arg | His | Asn | Ile | Glu |      |
|     |     | 195 |     |     |     |     | 200 |     |     |     |     | 205 |     |     |     |      |
| gac | ggc | agc | gtg | cag | ctc | gcc | gac | cac | tac | cag | cag | aac | acc | ccc | atc | 672  |
| Asp | Gly | Ser | Val | Gln | Leu | Ala | Asp | His | Tyr | Gln | Gln | Asn | Thr | Pro | Ile |      |
|     | 210 |     |     |     |     | 215 |     |     |     |     | 220 |     |     |     |     |      |
| ggc | gac | ggc | ccc | gtg | ctg | ctg | ccc | gac | aac | cac | tac | ctg | agc | acc | cag | 720  |
| Gly | Asp | Gly | Pro | Val | Leu | Leu | Pro | Asp | Asn | His | Tyr | Leu | Ser | Thr | Gln |      |
| 225 |     |     |     |     | 230 |     |     |     |     | 235 |     |     |     |     | 240 |      |
| tcc | gcc | ctg | agc | aaa | gac | ccc | aac | gag | aag | cgc | gat | cac | atg | gtc | ctg | 768  |
| Ser | Ala | Leu | Ser | Lys | Asp | Pro | Asn | Glu | Lys | Arg | Asp | His | Met | Val | Leu |      |
|     |     |     |     | 245 |     |     |     |     | 250 |     |     |     |     | 255 |     |      |
| ctg | gag | ttc | gtg | acc | gcc | gcc | ggg | atc | act | ctc | ggc | atg | gac | gag | ctg | 816  |
| Leu | Glu | Phe | Val | Thr | Ala | Ala | Gly | Ile | Thr | Leu | Gly | Met | Asp | Glu | Leu |      |
|     |     |     | 260 |     |     |     |     | 265 |     |     |     |     | 270 |     |     |      |
| tac | aag | ggt | ggt | acc | gga | ggc | gcc | gct | gat | act | cgc | att | ggt | gta | aca | 864  |
| Tyr | Lys | Gly | Gly | Thr | Gly | Gly | Ala | Ala | Asp | Thr | Arg | Ile | Gly | Val | Thr |      |
|     |     | 275 |     |     |     |     | 280 |     |     |     |     | 285 |     |     |     |      |
| atc | tat | aag | tac | gac | gat | aac | gcg | atg | tct | gta | gtg | cgc | aag | gct | att | 912  |
| Ile | Tyr | Lys | Tyr | Asp | Asp | Asn | Ala | Met | Ser | Val | Val | Arg | Lys | Ala | Ile |      |
|     | 290 |     |     |     |     | 295 |     |     |     |     | 300 |     |     |     |     |      |
| gag | caa | gat | gcg | aaa | gcc | gcg | cca | gat | gtt | cag | ctg | ctg | atg | aat | gat | 960  |
| Glu | Gln | Asp | Ala | Lys | Ala | Ala | Pro | Asp | Val | Gln | Leu | Leu | Met | Asn | Asp |      |
| 305 |     |     |     | 310 |     |     |     |     | 315 |     |     |     |     | 320 |     |      |
| tct | cag | aat | gac | cag | tcc | aag | cag | aac | gat | cag | atc | gac | gta | ttg | ctg | 1008 |
| Ser | Gln | Asn | Asp | Gln | Ser | Lys | Gln | Asn | Asp | Gln | Ile | Asp | Val | Leu | Leu |      |
|     |     |     |     | 325 |     |     |     |     | 330 |     |     |     |     | 335 |     |      |
| gcg | aaa | ggg | gtg | aag | gca | ctg | gca | atc | aac | ctg | gtt | gac | ccg | gca | gct | 1056 |
| Ala | Lys | Gly | Val | Lys | Ala | Leu | Ala | Ile | Asn | Leu | Val | Asp | Pro | Ala | Ala |      |
|     |     |     | 340 |     |     |     |     | 345 |     |     |     |     | 350 |     |     |      |
| gcg | ggt | acg | gtg | att | gag | aaa | gcg | cgt | ggg | caa | aac | gtg | ccg | gtg | gtt | 1104 |
| Ala | Gly | Thr | Val | Ile | Glu | Lys | Ala | Arg | Gly | Gln | Asn | Val | Pro | Val | Val |      |
|     |     | 355 |     |     |     |     | 360 |     |     |     |     | 365 |     |     |     |      |
| ttc | ttc | aac | aaa | gaa | ccg | tct | cgt | aag | gcg | ctg | gat | agc | tac | gac | aaa | 1152 |
| Phe | Phe | Asn | Lys | Glu | Pro | Ser | Arg | Lys | Ala | Leu | Asp | Ser | Tyr | Asp | Lys |      |
|     | 370 |     |     |     |     | 375 |     |     |     |     | 380 |     |     |     |     |      |

-continued

| | |
|---|---|
| gcc tac tac gtt ggc act gac tcc aaa gag tcc ggc att att caa ggc<br>Ala Tyr Tyr Val Gly Thr Asp Ser Lys Glu Ser Gly Ile Ile Gln Gly<br>385                    390                    395                    400 | 1200 |
| gat ttg att gct aaa cac tgg gcg gcg aat cag ggt tgg gat ctg aac<br>Asp Leu Ile Ala Lys His Trp Ala Ala Asn Gln Gly Trp Asp Leu Asn<br>                    405                    410                    415 | 1248 |
| aaa gac ggt cag att cag ttc gta ctg ctg aaa ggt gaa ccg ggc cat<br>Lys Asp Gly Gln Ile Gln Phe Val Leu Leu Lys Gly Glu Pro Gly His<br>            420                    425                    430 | 1296 |
| ccg gat gca gaa gca cgt acc act tac gtg att aaa gaa ttg aac gat<br>Pro Asp Ala Glu Ala Arg Thr Thr Tyr Val Ile Lys Glu Leu Asn Asp<br>435                    440                    445 | 1344 |
| aaa ggc atc aaa act gaa cag tta cag tta gat acc gca atg tgg gac<br>Lys Gly Ile Lys Thr Glu Gln Leu Gln Leu Asp Thr Ala Met Trp Asp<br>450                    455                    460 | 1392 |
| acc gct cag gcg aaa gat aag atg gac gcc tgg ctg tct ggc ccg aac<br>Thr Ala Gln Ala Lys Asp Lys Met Asp Ala Trp Leu Ser Gly Pro Asn<br>465                    470                    475                    480 | 1440 |
| gcc aac aaa atc gaa gtg gtt atc gcc aac aac gat gcg atg gca atg<br>Ala Asn Lys Ile Glu Val Val Ile Ala Asn Asn Asp Ala Met Ala Met<br>                    485                    490                    495 | 1488 |
| ggc gcg gtt gaa gcg ctg aaa gca cac aac aag tcc agc att ccg gtg<br>Gly Ala Val Glu Ala Leu Lys Ala His Asn Lys Ser Ser Ile Pro Val<br>            500                    505                    510 | 1536 |
| ttt ggc gtc gat gcg ctg cca gaa gcg ctg gcg ctg gtg aaa tcc ggt<br>Phe Gly Val Asp Ala Leu Pro Glu Ala Leu Ala Leu Val Lys Ser Gly<br>515                    520                    525 | 1584 |
| gca ctg gcg ggc acc gta ctg aac gat gct aac aac cag gcg aaa gcg<br>Ala Leu Ala Gly Thr Val Leu Asn Asp Ala Asn Asn Gln Ala Lys Ala<br>530                    535                    540 | 1632 |
| acc ttt gat ctg gcg aaa aac ctg gcc gat ggt aaa ggt gcg gct gat<br>Thr Phe Asp Leu Ala Lys Asn Leu Ala Asp Gly Lys Gly Ala Ala Asp<br>545                    550                    555                    560 | 1680 |
| ggc tcg gct ggt atg gtg agc aag ggc gag gag ctg ttc acc ggg gtg<br>Gly Ser Ala Gly Met Val Ser Lys Gly Glu Glu Leu Phe Thr Gly Val<br>                    565                    570                    575 | 1728 |
| gtg ccc atc ctg gtc gag ctg gac ggc gac gta aac ggc cac aag ttc<br>Val Pro Ile Leu Val Glu Leu Asp Gly Asp Val Asn Gly His Lys Phe<br>            580                    585                    590 | 1776 |
| agc gtg tcc ggc gag ggc gag ggc gat gcc acc tac ggc aag ctg acc<br>Ser Val Ser Gly Glu Gly Glu Gly Asp Ala Thr Tyr Gly Lys Leu Thr<br>595                    600                    605 | 1824 |
| ctg aag ttc atc tgc acc acc ggc aag ctg ccc gtg ccc tgg ccc acc<br>Leu Lys Phe Ile Cys Thr Thr Gly Lys Leu Pro Val Pro Trp Pro Thr<br>610                    615                    620 | 1872 |
| ctc gtg acc acc ctg acc tgg ggc gtg cag tgc ttc agc cgc tac ccc<br>Leu Val Thr Thr Leu Thr Trp Gly Val Gln Cys Phe Ser Arg Tyr Pro<br>625                    630                    635                    640 | 1920 |
| gac cac atg aag cag cac gac ttc ttc aag tcc gcc atg ccc gaa ggc<br>Asp His Met Lys Gln His Asp Phe Phe Lys Ser Ala Met Pro Glu Gly<br>                    645                    650                    655 | 1968 |
| tac gtc cag gag cgc acc atc ttc ttc aag gac gac ggc aac tac aag<br>Tyr Val Gln Glu Arg Thr Ile Phe Phe Lys Asp Asp Gly Asn Tyr Lys<br>            660                    665                    670 | 2016 |
| acc cgc gcc gag gtg aag ttc gag ggc gac acc ctg gtg aac cgc atc<br>Thr Arg Ala Glu Val Lys Phe Glu Gly Asp Thr Leu Val Asn Arg Ile<br>675                    680                    685 | 2064 |
| gag ctg aag ggc atc gac ttc aag gag gac ggc aac atc ctg ggg cac<br>Glu Leu Lys Gly Ile Asp Phe Lys Glu Asp Gly Asn Ile Leu Gly His<br>690                    695                    700 | 2112 |

```
aag ctg gag tac aac tac atc agc cac aac gtc tat atc acc gcc gac     2160
Lys Leu Glu Tyr Asn Tyr Ile Ser His Asn Val Tyr Ile Thr Ala Asp
705             710                 715                 720 aag cag aag aac ggc atc aag gcc aac ttc aag atc cgc cac aac atc     2208
Lys Gln Lys Asn Gly Ile Lys Ala Asn Phe Lys Ile Arg His Asn Ile
            725                 730                 735 gag gac ggc agc gtg cag ctc gcc gac cac tac cag cag aac acc ccc     2256
Glu Asp Gly Ser Val Gln Leu Ala Asp His Tyr Gln Gln Asn Thr Pro
        740                 745                 750 atc ggc gac ggc ccc gtg ctg ctg ccc gac aac cac tac ctg agc acc     2304
Ile Gly Asp Gly Pro Val Leu Leu Pro Asp Asn His Tyr Leu Ser Thr
    755                 760                 765 cag tcc gcc ctg agc aaa gac ccc aac gag aag cgc gat cac atg gtc     2352
Gln Ser Ala Leu Ser Lys Asp Pro Asn Glu Lys Arg Asp His Met Val
770                 775                 780 ctg ctg gag ttc gtg acc gcc gcc ggg atc act ctc ggc atg gac gag     2400
Leu Leu Glu Phe Val Thr Ala Ala Gly Ile Thr Leu Gly Met Asp Glu
785             790                 795                 800 ctg tac ggt agc cga tgg aaa atc gac aac aaa gtg gtc cgc gta cct     2448
Leu Tyr Gly Ser Arg Trp Lys Ile Asp Asn Lys Val Val Arg Val Pro
            805                 810                 815 tat gtt ggc gta gat aaa gac aac ctg gct gaa ttc agc aag aaa taa     2496
Tyr Val Gly Val Asp Lys Asp Asn Leu Ala Glu Phe Ser Lys Lys
        820                 825                 830

<210> SEQ ID NO 26
<211> LENGTH: 831
<212> TYPE: PRT
<213> ORGANISM: Artificial Sequence
<220> FEATURE:
<223> OTHER INFORMATION: FLIP-YFP-mglBF16A-T282S-CFP-N283R Vector

<400> SEQUENCE: 26

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Gly Arg Met Val Ser Lys Gly Glu Glu Leu Phe Thr Gly Val Val
        35                  40                  45

Pro Ile Leu Val Glu Leu Asp Gly Asp Val Asn Gly His Lys Phe Ser
    50                  55                  60

Val Ser Gly Glu Gly Glu Gly Asp Ala Thr Tyr Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Trp Gly Val Gln Cys Phe Ser Arg Tyr Pro Asp
            100                 105                 110

His Met Lys Gln His Asp Phe Phe Lys Ser Ala Met Pro Glu Gly Tyr
        115                 120                 125

Val Gln Glu Arg Thr Ile Phe Phe Lys Asp Asp Gly Asn Tyr Lys Thr
    130                 135                 140

Arg Ala Glu Val Lys Phe Glu Gly Asp Thr Leu Val Asn Arg Ile Glu
145                 150                 155                 160

Leu Lys Gly Ile Asp Phe Lys Glu Asp Gly Asn Ile Leu Gly His Lys
                165                 170                 175

Leu Glu Tyr Asn Tyr Ile Ser His Asn Val Tyr Ile Thr Ala Asp Lys
            180                 185                 190

Gln Lys Asn Gly Ile Lys Ala Asn Phe Lys Ile Arg His Asn Ile Glu
```

```
             195                 200                 205
Asp Gly Ser Val Gln Leu Ala Asp His Tyr Gln Asn Thr Pro Ile
210                 215                 220

Gly Asp Gly Pro Val Leu Leu Pro Asp Asn His Tyr Leu Ser Thr Gln
225                 230                 235                 240

Ser Ala Leu Ser Lys Asp Pro Asn Glu Lys Arg Asp His Met Val Leu
                245                 250                 255

Leu Glu Phe Val Thr Ala Ala Gly Ile Thr Leu Gly Met Asp Glu Leu
            260                 265                 270

Tyr Lys Gly Gly Thr Gly Gly Ala Ala Asp Thr Arg Ile Gly Val Thr
        275                 280                 285

Ile Tyr Lys Tyr Asp Asp Asn Ala Met Ser Val Val Arg Lys Ala Ile
    290                 295                 300

Glu Gln Asp Ala Lys Ala Ala Pro Asp Val Gln Leu Leu Met Asn Asp
305                 310                 315                 320

Ser Gln Asn Asp Gln Ser Lys Gln Asn Asp Gln Ile Asp Val Leu Leu
                325                 330                 335

Ala Lys Gly Val Lys Ala Leu Ala Ile Asn Leu Val Asp Pro Ala Ala
            340                 345                 350

Ala Gly Thr Val Ile Glu Lys Ala Arg Gly Gln Asn Val Pro Val Val
        355                 360                 365

Phe Phe Asn Lys Glu Pro Ser Arg Lys Ala Leu Asp Ser Tyr Asp Lys
    370                 375                 380

Ala Tyr Tyr Val Gly Thr Asp Ser Lys Glu Ser Gly Ile Ile Gln Gly
385                 390                 395                 400

Asp Leu Ile Ala Lys His Trp Ala Ala Asn Gln Gly Trp Asp Leu Asn
                405                 410                 415

Lys Asp Gly Gln Ile Gln Phe Val Leu Leu Lys Gly Glu Pro Gly His
            420                 425                 430

Pro Asp Ala Glu Ala Arg Thr Thr Tyr Val Ile Lys Glu Leu Asn Asp
        435                 440                 445

Lys Gly Ile Lys Thr Glu Gln Leu Gln Leu Asp Thr Ala Met Trp Asp
    450                 455                 460

Thr Ala Gln Ala Lys Asp Lys Met Asp Ala Trp Leu Ser Gly Pro Asn
465                 470                 475                 480

Ala Asn Lys Ile Glu Val Val Ile Ala Asn Asn Asp Ala Met Ala Met
                485                 490                 495

Gly Ala Val Glu Ala Leu Lys His Asn Lys Ser Ser Ile Pro Val
            500                 505                 510

Phe Gly Val Asp Ala Leu Pro Glu Ala Leu Ala Leu Val Lys Ser Gly
        515                 520                 525

Ala Leu Ala Gly Thr Val Leu Asn Asp Ala Asn Asn Gln Ala Lys Ala
    530                 535                 540

Thr Phe Asp Leu Ala Lys Asn Leu Ala Asp Gly Lys Gly Ala Ala Asp
545                 550                 555                 560

Gly Ser Ala Gly Met Val Ser Lys Gly Glu Glu Leu Phe Thr Gly Val
                565                 570                 575

Val Pro Ile Leu Val Glu Leu Asp Gly Asp Val Asn Gly His Lys Phe
            580                 585                 590

Ser Val Ser Gly Glu Gly Glu Gly Asp Ala Thr Tyr Gly Lys Leu Thr
        595                 600                 605

Leu Lys Phe Ile Cys Thr Thr Gly Lys Leu Pro Val Pro Trp Pro Thr
    610                 615                 620
```

```
Leu Val Thr Thr Leu Thr Trp Gly Val Gln Cys Phe Ser Arg Tyr Pro
625                 630                 635                 640

Asp His Met Lys Gln His Asp Phe Phe Lys Ser Ala Met Pro Glu Gly
                645                 650                 655

Tyr Val Gln Glu Arg Thr Ile Phe Phe Lys Asp Asp Gly Asn Tyr Lys
            660                 665                 670

Thr Arg Ala Glu Val Lys Phe Glu Gly Asp Thr Leu Val Asn Arg Ile
        675                 680                 685

Glu Leu Lys Gly Ile Asp Phe Lys Glu Asp Gly Asn Ile Leu Gly His
690                 695                 700

Lys Leu Glu Tyr Asn Tyr Ile Ser His Asn Val Tyr Ile Thr Ala Asp
705                 710                 715                 720

Lys Gln Lys Asn Gly Ile Lys Ala Asn Phe Lys Ile Arg His Asn Ile
                725                 730                 735

Glu Asp Gly Ser Val Gln Leu Ala Asp His Tyr Gln Gln Asn Thr Pro
            740                 745                 750

Ile Gly Asp Gly Pro Val Leu Leu Pro Asp Asn His Tyr Leu Ser Thr
        755                 760                 765

Gln Ser Ala Leu Ser Lys Asp Pro Asn Glu Lys Arg Asp His Met Val
770                 775                 780

Leu Leu Glu Phe Val Thr Ala Ala Gly Ile Thr Leu Gly Met Asp Glu
785                 790                 795                 800

Leu Tyr Gly Ser Arg Trp Lys Ile Asp Asn Lys Val Val Arg Val Pro
                805                 810                 815

Tyr Val Gly Val Asp Lys Asp Asn Leu Ala Glu Phe Ser Lys Lys
            820                 825                 830

<210> SEQ ID NO 27
<211> LENGTH: 909
<212> TYPE: DNA
<213> ORGANISM: Escherichia coli K12
<220> FEATURE:
<221> NAME/KEY: CDS
<222> LOCATION: (1)..(909)

<400> SEQUENCE: 27 atg caa tta cgt aaa cct gcc aca gca atc ctc gcc ctg gcg ctt tcc      48
Met Gln Leu Arg Lys Pro Ala Thr Ala Ile Leu Ala Leu Ala Leu Ser
1               5                   10                  15 gca gga ctg gca cag gca gat gac gcc gcc ccg gca gcg ggc agt act      96
Ala Gly Leu Ala Gln Ala Asp Asp Ala Ala Pro Ala Ala Gly Ser Thr
            20                  25                  30 ctg gac aaa atc gcc aaa aac ggt gtg att gtc gtc ggt cac cgt gaa     144
Leu Asp Lys Ile Ala Lys Asn Gly Val Ile Val Val Gly His Arg Glu
        35                  40                  45 tct tca gtg cct ttc tct tat tac gac aat cag caa aaa gtg gtg ggt     192
Ser Ser Val Pro Phe Ser Tyr Tyr Asp Asn Gln Gln Lys Val Val Gly
    50                  55                  60 tac tcg cag gat tac tcc aac gcc att gtt gaa gca gtg aaa aag aaa     240
Tyr Ser Gln Asp Tyr Ser Asn Ala Ile Val Glu Ala Val Lys Lys Lys
65                  70                  75                  80 ctc aac aaa ccg gac ttg cag gta aaa ctg att ccg att acc tca caa     288
Leu Asn Lys Pro Asp Leu Gln Val Lys Leu Ile Pro Ile Thr Ser Gln
                85                  90                  95 aac cgt att cca ctg ctg caa aac ggc act ttc gat ttt gaa tgt ggt     336
Asn Arg Ile Pro Leu Leu Gln Asn Gly Thr Phe Asp Phe Glu Cys Gly
            100                 105                 110 tct acc acc aac aac gtc gaa cgc caa aaa cag gcg gct ttc tct gac     384
Ser Thr Thr Asn Asn Val Glu Arg Gln Lys Gln Ala Ala Phe Ser Asp
```

```
                   115                 120                 125
act att ttc gtg gtc ggt acg cgc ctg ttg acc aaa aag ggt ggc gat    432
Thr Ile Phe Val Val Gly Thr Arg Leu Leu Thr Lys Lys Gly Gly Asp
    130                 135                 140 atc aaa gat ttt gcc aac ctg aaa gac aaa gcc gta gtc gtc act tcc    480
Ile Lys Asp Phe Ala Asn Leu Lys Asp Lys Ala Val Val Val Thr Ser
145                 150                 155                 160 ggc act acc tct gaa gtt ttg ctc aac aaa ctg aat gaa gag caa aaa    528
Gly Thr Thr Ser Glu Val Leu Leu Asn Lys Leu Asn Glu Glu Gln Lys
                165                 170                 175 atg aat atg cgc atc atc agc gcc aaa gat cac ggt gac tct ttc cgc    576
Met Asn Met Arg Ile Ile Ser Ala Lys Asp His Gly Asp Ser Phe Arg
            180                 185                 190 acc ctg gaa agc ggt cgt gcc gtt gcc ttt atg atg gat gac gct ctg    624
Thr Leu Glu Ser Gly Arg Ala Val Ala Phe Met Met Asp Asp Ala Leu
        195                 200                 205 ctg gcc ggt gaa cgt gcg aaa gcg aag aaa cca gac aac tgg gaa atc    672
Leu Ala Gly Glu Arg Ala Lys Ala Lys Lys Pro Asp Asn Trp Glu Ile
    210                 215                 220 gtc ggc aag ccg cag tct cag gag gcc tac ggt tgt atg ttg cgt aaa    720
Val Gly Lys Pro Gln Ser Gln Glu Ala Tyr Gly Cys Met Leu Arg Lys
225                 230                 235                 240 gat gat ccg cag ttc aaa aag ctg atg gat gac acc atc gct cag gtg    768
Asp Asp Pro Gln Phe Lys Lys Leu Met Asp Asp Thr Ile Ala Gln Val
                245                 250                 255 cag acc tcc ggt gaa gcg gaa aaa tgg ttt gat aag tgg ttc aaa aat    816
Gln Thr Ser Gly Glu Ala Glu Lys Trp Phe Asp Lys Trp Phe Lys Asn
            260                 265                 270 cca att ccg ccg aaa aac ctg aac atg aat ttc gaa ctg tca gac gaa    864
Pro Ile Pro Pro Lys Asn Leu Asn Met Asn Phe Glu Leu Ser Asp Glu
        275                 280                 285 atg aaa gca ctg ttc aaa gaa ccg aat gac aag gca ctg aac taa        909
Met Lys Ala Leu Phe Lys Glu Pro Asn Asp Lys Ala Leu Asn
    290                 295                 300

<210> SEQ ID NO 28
<211> LENGTH: 302
<212> TYPE: PRT
<213> ORGANISM: Escherichia coli K12

<400> SEQUENCE: 28

Met Gln Leu Arg Lys Pro Ala Thr Ala Ile Leu Ala Leu Ala Leu Ser
1               5                   10                  15

Ala Gly Leu Ala Gln Ala Asp Asp Ala Ala Pro Ala Ala Gly Ser Thr
            20                  25                  30

Leu Asp Lys Ile Ala Lys Asn Gly Val Ile Val Val Gly His Arg Glu
        35                  40                  45

Ser Ser Val Pro Phe Ser Tyr Tyr Asp Asn Gln Gln Lys Val Val Gly
    50                  55                  60

Tyr Ser Gln Asp Tyr Ser Asn Ala Ile Val Glu Ala Val Lys Lys Lys
65                  70                  75                  80

Leu Asn Lys Pro Asp Leu Gln Val Lys Leu Ile Pro Ile Thr Ser Gln
                85                  90                  95

Asn Arg Ile Pro Leu Leu Gln Asn Gly Thr Phe Asp Phe Glu Cys Gly
            100                 105                 110

Ser Thr Thr Asn Asn Val Glu Arg Gln Lys Gln Ala Ala Phe Ser Asp
        115                 120                 125

Thr Ile Phe Val Val Gly Thr Arg Leu Leu Thr Lys Lys Gly Gly Asp
    130                 135                 140
```

```
Ile Lys Asp Phe Ala Asn Leu Lys Asp Lys Ala Val Val Thr Ser
145                 150                 155                 160

Gly Thr Thr Ser Glu Val Leu Leu Asn Lys Leu Asn Glu Glu Gln Lys
                165                 170                 175

Met Asn Met Arg Ile Ile Ser Ala Lys Asp His Gly Asp Ser Phe Arg
                180                 185                 190

Thr Leu Glu Ser Gly Arg Ala Val Ala Phe Met Met Asp Asp Ala Leu
                195                 200                 205

Leu Ala Gly Glu Arg Ala Lys Ala Lys Pro Asp Asn Trp Glu Ile
210                 215                 220

Val Gly Lys Pro Gln Ser Gln Glu Ala Tyr Gly Cys Met Leu Arg Lys
225                 230                 235                 240

Asp Asp Pro Gln Phe Lys Lys Leu Met Asp Asp Thr Ile Ala Gln Val
                245                 250                 255

Gln Thr Ser Gly Glu Ala Glu Lys Trp Phe Asp Lys Trp Phe Lys Asn
                260                 265                 270

Pro Ile Pro Pro Lys Asn Leu Asn Met Asn Phe Glu Leu Ser Asp Glu
                275                 280                 285

Met Lys Ala Leu Phe Lys Glu Pro Asn Asp Lys Ala Leu Asn
290                 295                 300
```

<210> SEQ ID NO 29

<400> SEQUENCE: 29

000

<210> SEQ ID NO 30
<211> LENGTH: 6
<212> TYPE: PRT
<213> ORGANISM: Artificial Sequence
<220> FEATURE:
<223> OTHER INFORMATION: linker sequence

<400> SEQUENCE: 30

```
Gly Asn Asn Ser Ala Gly
1               5
```

<210> SEQ ID NO 31
<211> LENGTH: 6
<212> TYPE: PRT
<213> ORGANISM: Artificial Sequence
<220> FEATURE:
<223> OTHER INFORMATION: linker sequence

<400> SEQUENCE: 31

```
Gly Ser Ala Asp Asp Gly
1               5
```

<210> SEQ ID NO 32
<211> LENGTH: 6
<212> TYPE: PRT
<213> ORGANISM: Artificial Sequence
<220> FEATURE:
<223> OTHER INFORMATION: linker sequence

<400> SEQUENCE: 32

```
Gly Gly Thr Gly Gly Ala
1               5
```

-continued

```
<210> SEQ ID NO 33
<211> LENGTH: 18
<212> TYPE: DNA
<213> ORGANISM: Artificial Sequence
<220> FEATURE:
<223> OTHER INFORMATION: linker sequence

<400> SEQUENCE: 33
ggtggtaccg gaggcgcc                                                 18

<210> SEQ ID NO 34
<211> LENGTH: 15
<212> TYPE: DNA
<213> ORGANISM: Artificial Sequence
<220> FEATURE:
<223> OTHER INFORMATION: partial sequence from pRSETB N58V-ECFP232-Q59N

<400> SEQUENCE: 34
agcgctggta tggtg                                                    15

<210> SEQ ID NO 35
<211> LENGTH: 15
<212> TYPE: DNA
<213> ORGANISM: Artificial Sequence
<220> FEATURE:
<223> OTHER INFORMATION: partial sequence from pRSETB N58V-ECFP232-Q59N

<400> SEQUENCE: 35
actctcggta gcgct                                                    15

<210> SEQ ID NO 36
<211> LENGTH: 4
<212> TYPE: PRT
<213> ORGANISM: Artificial Sequence
<220> FEATURE:
<223> OTHER INFORMATION: partial sequence from pRSETB N58V-ECFP232-Q59N

<400> SEQUENCE: 36

Ala Gly Met Val
1

<210> SEQ ID NO 37
<211> LENGTH: 4
<212> TYPE: PRT
<213> ORGANISM: Artificial Sequence
<220> FEATURE:
<223> OTHER INFORMATION: partial sequence from pRSETB N58V-ECFP232-Q59N

<400> SEQUENCE: 37

Thr Leu Gly Ser
1

<210> SEQ ID NO 38
<211> LENGTH: 30
<212> TYPE: DNA
<213> ORGANISM: Artificial Sequence
<220> FEATURE:
<223> OTHER INFORMATION: partial sequence from pRSETB A216-cpVenus-K217

<400> SEQUENCE: 38
aaagcgggca acaacagcgc tggtgacggc                                    30

<210> SEQ ID NO 39
<211> LENGTH: 30
<212> TYPE: DNA
<213> ORGANISM: Artificial Sequence
<220> FEATURE:
<223> OTHER INFORMATION: partial sequence from pRSETB A216-cpVenus-K217
```

```
<400> SEQUENCE: 39
atcgagggta gcgctgacga cggaaagaaa                                          30

<210> SEQ ID NO 40
<211> LENGTH: 10
<212> TYPE: PRT
<213> ORGANISM: Artificial Sequence
<220> FEATURE:
<223> OTHER INFORMATION: partial sequence from pRSETB A216-cpVenus-K217

<400> SEQUENCE: 40

Lys Ala Gly Asn Asn Ser Ala Gly Asn Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: partial sequence from pRSETB A216-cpVenus-K217

<400> SEQUENCE: 41

Ile Glu Gly Ser Ala Asp Asp Gly Lys Lys
1               5                   10

<210> SEQ ID NO 42
<211> LENGTH: 45
<212> TYPE: DNA
<213> ORGANISM: Artificial Sequence
<220> FEATURE:
<223> OTHER INFORMATION: partial sequence from FLII275 Pglu plasmid

<400> SEQUENCE: 42
actctcggca tggacgagct gtacaagggt ggtaccggag gcgcc                         45

<210> SEQ ID NO 43
<211> LENGTH: 33
<212> TYPE: DNA
<213> ORGANISM: Artificial Sequence
<220> FEATURE:
<223> OTHER INFORMATION: partial sequence from FLII2 Pglu plasmid

<400> SEQUENCE: 43
actctcggca tggacgagct gtacggtagc cga                                      33

<210> SEQ ID NO 44
<211> LENGTH: 51
<212> TYPE: DNA
<213> ORGANISM: Artificial Sequence
<220> FEATURE:
<223> OTHER INFORMATION: partial sequence from FLII2 Pglu plasmid

<400> SEQUENCE: 44
gaattcagca agaaaggcgc cggtaccggt ggaatggtga gcaagggcga g                  51

<210> SEQ ID NO 45
<211> LENGTH: 39
<212> TYPE: DNA
<213> ORGANISM: Artificial Sequence
<220> FEATURE:
<223> OTHER INFORMATION: partial sequence from FLII2 Pglu plasmid

<400> SEQUENCE: 45
gaattcagca agaaaggtac catggtgagc aagggcgag                                39
```

```
<210> SEQ ID NO 46
<211> LENGTH: 33
<212> TYPE: DNA
<213> ORGANISM: Artificial Sequence
<220> FEATURE:
<223> OTHER INFORMATION: partial sequence from FLII2 Pglu plasmid

<400> SEQUENCE: 46
gaattcagca agaaaatggt gagcaagggc gag                              33

<210> SEQ ID NO 47
<211> LENGTH: 48
<212> TYPE: DNA
<213> ORGANISM: Artificial Sequence
<220> FEATURE:
<223> OTHER INFORMATION: partial sequence from FLII2 Pglu plasmid

<400> SEQUENCE: 47
ttcagcaaga aaggcgccgg taccggtgga atggtgagca agggcgag              48

<210> SEQ ID NO 48
<211> LENGTH: 45
<212> TYPE: DNA
<213> ORGANISM: Artificial Sequence
<220> FEATURE:
<223> OTHER INFORMATION: partial sequence from FLII2 Pglu plasmid

<400> SEQUENCE: 48
agcaagaaag gcgccggtac cggtggaatg gtgagcaagg gcgag                 45

<210> SEQ ID NO 49
<211> LENGTH: 42
<212> TYPE: DNA
<213> ORGANISM: Artificial Sequence
<220> FEATURE:
<223> OTHER INFORMATION: partial sequence from FLII2 Pglu plasmid

<400> SEQUENCE: 49
aagaaaggcg ccggtaccgg tggaatggtg agcaagggcg ag                    42

<210> SEQ ID NO 50
<211> LENGTH: 39
<212> TYPE: DNA
<213> ORGANISM: Artificial Sequence
<220> FEATURE:
<223> OTHER INFORMATION: partial sequence from FLII2 Pglu plasmid

<400> SEQUENCE: 50
aaaggcgccg gtaccggtgg aatggtgagc aagggcgag                        39

<210> SEQ ID NO 51
<211> LENGTH: 36
<212> TYPE: DNA
<213> ORGANISM: Artificial Sequence
<220> FEATURE:
<223> OTHER INFORMATION: partial sequence from FLII2 Pglu plasmid

<400> SEQUENCE: 51
ggcgccggta ccggtggaat ggtgagcaag ggcgag                           36

<210> SEQ ID NO 52
<211> LENGTH: 33
<212> TYPE: DNA
<213> ORGANISM: Artificial Sequence
```

```
<220> FEATURE:
<223> OTHER INFORMATION: partial sequence from FLII2 Pglu plasmid

<400> SEQUENCE: 52
gccggtaccg gtggaatggt gagcaagggc gag                                    33

<210> SEQ ID NO 53
<211> LENGTH: 30
<212> TYPE: DNA
<213> ORGANISM: Artificial Sequence
<220> FEATURE:
<223> OTHER INFORMATION: partial sequence from FLII2 Pglu plasmid

<400> SEQUENCE: 53
ggtaccggtg aatggtgagc aagggcgag                                         30

<210> SEQ ID NO 54
<211> LENGTH: 27
<212> TYPE: DNA
<213> ORGANISM: Artificial Sequence
<220> FEATURE:
<223> OTHER INFORMATION: partial sequence from FLII2 Pglu plasmid

<400> SEQUENCE: 54
accggtggaa tggtgagcaa gggcgag                                           27

<210> SEQ ID NO 55
<211> LENGTH: 24
<212> TYPE: DNA
<213> ORGANISM: Artificial Sequence
<220> FEATURE:
<223> OTHER INFORMATION: partial sequence from FLII2 Pglu plasmid

<400> SEQUENCE: 55
ggtggaatgg tgagcaaggg cgag                                              24

<210> SEQ ID NO 56
<211> LENGTH: 21
<212> TYPE: DNA
<213> ORGANISM: Artificial Sequence
<220> FEATURE:
<223> OTHER INFORMATION: partial sequence from FLII2 Pglu plasmid

<400> SEQUENCE: 56
ggaatggtga gcaagggcga g                                                 21

<210> SEQ ID NO 57
<211> LENGTH: 18
<212> TYPE: DNA
<213> ORGANISM: Artificial Sequence
<220> FEATURE:
<223> OTHER INFORMATION: partial sequence from FLII2 Pglu plasmid

<400> SEQUENCE: 57
atggtgagca agggcgag                                                     18

<210> SEQ ID NO 58
<211> LENGTH: 15
<212> TYPE: DNA
<213> ORGANISM: Artificial Sequence
<220> FEATURE:
<223> OTHER INFORMATION: partial sequence from FLII2 Pglu plasmid

<400> SEQUENCE: 58
gtgagcaagg gcgag                                                        15
```

```
<210> SEQ ID NO 59
<211> LENGTH: 12
<212> TYPE: DNA
<213> ORGANISM: Artificial Sequence
<220> FEATURE:
<223> OTHER INFORMATION: partial sequence from FLII2 Pglu plasmid

<400> SEQUENCE: 59
agcaagggcg ag                                                          12
```